(12) United States Patent
Marchand et al.

(10) Patent No.: US 12,251,120 B2
(45) Date of Patent: *Mar. 18, 2025

(54) DEVICES AND METHODS FOR TREATING VASCULAR OCCLUSION

(71) Applicant: Inari Medical, Inc., Irvine, CA (US)

(72) Inventors: Phil Marchand, Lake Forest, CA (US); Benjamin E. Merritt, San Clemente, CA (US); John C. Thress, Capistrano Beach, CA (US); Jacob F. Louw, Carlsbad, CA (US); Paul Lubock, Monarch Beach, CA (US); Brian J. Cox, Laguna Nigel, CA (US)

(73) Assignee: Inari Medical, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/311,805

(22) Filed: May 3, 2023

(65) Prior Publication Data

US 2023/0329734 A1    Oct. 19, 2023

Related U.S. Application Data

(63) Continuation of application No. 17/154,806, filed on Jan. 21, 2021, now Pat. No. 11,806,033, which is a
(Continued)

(51) Int. Cl.
    *A61B 17/221*    (2006.01)
    *A61B 17/3207*    (2006.01)
    (Continued)

(52) U.S. Cl.
    CPC .... *A61B 17/221* (2013.01); *A61B 17/320725* (2013.01); *A61F 2/013* (2013.01);
    (Continued)

(58) Field of Classification Search
    CPC .............. A61B 17/221; A61B 17/3415; A61B 17/320725; A61B 2017/2212; A61B 2017/2215; A61B 2017/22094
    See application file for complete search history.

(56) References Cited

U.S. PATENT DOCUMENTS

| 1,101,890 A | 6/1914 | Tunstead |
| 2,502,639 A | 2/1948 | Blake |

(Continued)

FOREIGN PATENT DOCUMENTS

| AU | 2015210338 | 8/2015 |
| CN | 102186427 | 9/2011 |

(Continued)

OTHER PUBLICATIONS

US 12,114,876 B2, 10/2024, Quick et al. (withdrawn)
(Continued)

*Primary Examiner* — Tuan V Nguyen
(74) *Attorney, Agent, or Firm* — Perkins Coie LLP

(57) ABSTRACT

Systems and methods for removal of thrombus from a blood vessel in a body of a patient are disclosed herein. The method can include: providing a thrombus extraction device including a proximal self-expanding member formed of a fenestrated structure, a substantially cylindrical portion formed of a net-like filament mesh structure having a proximal end coupled to a distal end of the fenestrated structure; advancing a catheter constraining the thrombus extraction device through a vascular thrombus, deploying the thrombus extraction device by stacking a portion of the net-like filament mesh structure outside of the catheter by distally advancing the self-expanding member until the self-expanding member is beyond a distal end of the catheter; retracting the self-expanding member to unstack the portion of the net-like filament mesh structure and to capture
(Continued)

the portion of the thrombus; and withdrawing the thrombus extraction device from the body.

20 Claims, 33 Drawing Sheets

Related U.S. Application Data continuation of application No. 16/160,920, filed on Oct. 15, 2018, now Pat. No. 10,912,577, which is a continuation of application No. 15/498,320, filed on Apr. 26, 2017, now Pat. No. 10,098,651.

(60) Provisional application No. 62/444,705, filed on Jan. 10, 2017.

(51) Int. Cl.
*A61F 2/01* (2006.01)
*A61B 17/22* (2006.01)

(52) U.S. Cl.
CPC ............. *A61B 2017/22094* (2013.01); *A61B 2017/2212* (2013.01); *A61B 2017/2215* (2013.01); *A61F 2/011* (2020.05); *A61F 2002/016* (2013.01)

(56) References Cited

U.S. PATENT DOCUMENTS

| | | |
|---|---|---|
| 2,707,954 A | 5/1955 | J. L., Sr. |
| 2,784,717 A | 3/1957 | Thompson |
| 2,846,179 A | 8/1958 | Monckton |
| 2,955,592 A | 10/1960 | Maclean |
| 3,088,363 A | 5/1963 | Sparks |
| 3,197,173 A | 7/1965 | Taubenheim |
| 3,383,131 A | 5/1968 | Rosfelder |
| 3,416,531 A | 12/1968 | Edwards |
| 3,435,826 A | 4/1969 | Fogarty |
| 3,438,607 A | 4/1969 | Williams et al. |
| 3,515,137 A | 6/1970 | Santomieri |
| 3,661,144 A | 5/1972 | Jensen et al. |
| 3,675,657 A | 7/1972 | Gauthier |
| 3,785,380 A | 1/1974 | Brumfield |
| 3,860,006 A | 1/1975 | Patel |
| 3,863,624 A | 2/1975 | Gram |
| 3,892,161 A | 7/1975 | Sokol |
| 3,923,065 A | 12/1975 | Nozick et al. |
| 4,030,503 A | 6/1977 | Clark, III |
| 4,034,642 A | 7/1977 | Iannucci et al. |
| 4,036,232 A | 7/1977 | Genese |
| 4,187,849 A | 2/1980 | Stim |
| 4,222,380 A | 9/1980 | Terayama |
| 4,243,040 A | 1/1981 | Beecher |
| 4,287,808 A | 9/1981 | Leonard et al. |
| 4,324,262 A | 4/1982 | Hall |
| 4,393,872 A | 7/1983 | Reznik et al. |
| 4,401,107 A | 8/1983 | Harber et al. |
| 4,469,100 A | 9/1984 | Hardwick |
| 4,523,738 A | 6/1985 | Raftis et al. |
| 4,551,862 A | 11/1985 | Haber |
| 4,604,094 A | 8/1986 | Shook |
| 4,611,594 A | 9/1986 | Grayhack et al. |
| 4,634,421 A | 1/1987 | Hegemann |
| 4,643,184 A | 2/1987 | Mobin-Uddin |
| 4,646,736 A | 3/1987 | Auth et al. |
| 4,650,466 A | 3/1987 | Luther |
| 4,693,257 A | 9/1987 | Markham |
| 4,705,518 A | 11/1987 | Baker et al. |
| 4,776,337 A | 10/1988 | Palmaz |
| 4,790,812 A | 12/1988 | Hawkins, Jr. et al. |
| 4,826,483 A | 5/1989 | Molnar, IV |
| 4,863,440 A | 9/1989 | Chin et al. |
| 4,870,953 A | 10/1989 | DonMichael et al. |
| 4,880,408 A | 11/1989 | Cumes et al. |
| 4,883,458 A | 11/1989 | Shiber |
| 4,886,062 A | 12/1989 | Wiktor |
| 4,890,611 A | 1/1990 | Monfort et al. |
| 4,898,575 A | 2/1990 | Fischell et al. |
| 4,946,440 A | 8/1990 | Hall |
| 4,960,259 A | 10/1990 | Sunnanvader et al. |
| 4,978,341 A | 12/1990 | Niederhauser |
| 4,981,478 A | 1/1991 | Evard et al. |
| 5,030,201 A | 7/1991 | Palestrant |
| 5,053,008 A | 10/1991 | Bajaj |
| 5,059,178 A | 10/1991 | Ya |
| 5,100,423 A | 3/1992 | Fearnot |
| 5,127,626 A | 7/1992 | Hilal et al. |
| 5,129,910 A | 7/1992 | Phan et al. |
| 5,135,484 A | 8/1992 | Wright |
| 5,154,724 A | 10/1992 | Andrews |
| 5,158,533 A | 10/1992 | Strauss et al. |
| 5,158,564 A | 10/1992 | Schnepp-Pesch et al. |
| 5,192,274 A | 3/1993 | Bierman |
| 5,192,286 A | 3/1993 | Phan et al. |
| 5,192,290 A | 3/1993 | Hilal |
| 5,197,485 A | 3/1993 | Grooters |
| 5,234,403 A | 8/1993 | Yoda et al. |
| 5,242,461 A | 9/1993 | Kortenbach et al. |
| 5,244,619 A | 9/1993 | Burnham |
| 5,246,011 A | 9/1993 | Caillouette |
| 5,323,514 A | 6/1994 | Masuda et al. |
| 5,329,923 A | 7/1994 | Lundquist |
| 5,360,417 A | 11/1994 | Gravener et al. |
| 5,364,345 A | 11/1994 | Lowery et al. |
| 5,376,071 A | 12/1994 | Henderson |
| 5,376,101 A | 12/1994 | Green et al. |
| 5,383,887 A | 1/1995 | Nadal |
| 5,389,100 A | 2/1995 | Bacich et al. |
| 5,391,152 A | 2/1995 | Patterson et al. |
| 5,419,774 A | 5/1995 | Willard et al. |
| 5,421,824 A | 6/1995 | Clement et al. |
| 5,429,610 A | 7/1995 | Vaillancourt |
| 5,443,443 A | 8/1995 | Shiber |
| 5,456,667 A | 10/1995 | Ham et al. |
| 5,476,450 A | 12/1995 | Ruggio |
| 5,484,418 A | 1/1996 | Quiachon et al. |
| 5,490,859 A | 2/1996 | Mische et al. |
| 5,496,365 A | 3/1996 | Sgro |
| 5,527,326 A | 6/1996 | Hermann et al. |
| 5,549,626 A | 8/1996 | Miller et al. |
| 5,591,137 A | 1/1997 | Stevens |
| 5,639,276 A | 6/1997 | Weinstock et al. |
| 5,653,684 A | 8/1997 | Laptewicz et al. |
| 5,662,703 A | 9/1997 | Yurek et al. |
| 5,746,758 A | 5/1998 | Nordgren et al. |
| 5,749,858 A | 5/1998 | Cramer |
| 5,769,816 A | 6/1998 | Barbut et al. |
| 5,782,817 A | 7/1998 | Franzel et al. |
| 5,800,457 A | 9/1998 | Gelbfish |
| 5,827,229 A | 10/1998 | Auth et al. |
| 5,846,251 A | 12/1998 | Hart |
| 5,860,938 A | 1/1999 | Lafontaine et al. |
| 5,873,866 A | 2/1999 | Kondo et al. |
| 5,873,882 A | 2/1999 | Straub et al. |
| 5,867,385 A | 3/1999 | Ikari et al. |
| 5,876,414 A | 3/1999 | Straub |
| 5,895,406 A | 4/1999 | Gray et al. |
| 5,908,435 A | 6/1999 | Samuels |
| 5,911,710 A | 6/1999 | Barry et al. |
| 5,911,728 A | 6/1999 | Sepetka et al. |
| 5,911,733 A | 6/1999 | Parodi |
| 5,911,754 A | 6/1999 | Kanesaka et al. |
| 5,941,869 A | 8/1999 | Patterson et al. |
| 5,947,985 A | 9/1999 | Imram |
| 5,951,539 A | 9/1999 | Nita et al. |
| 5,954,737 A | 9/1999 | Lee |
| 5,971,938 A | 10/1999 | Hart et al. |
| 5,971,958 A | 10/1999 | Zhang |
| 5,972,019 A | 10/1999 | Engelson et al. |
| 5,974,938 A | 11/1999 | Lloyd |
| 5,989,233 A | 11/1999 | Yoon |
| 5,993,483 A | 11/1999 | Gianotti |
| 6,017,335 A | 1/2000 | Burnham |

(56) References Cited

U.S. PATENT DOCUMENTS

| | | |
|---|---|---|
| 6,030,397 A | 2/2000 | Moneti et al. |
| 6,059,745 A | 5/2000 | Gelbfish |
| 6,059,814 A | 5/2000 | Ladd |
| 6,066,158 A | 5/2000 | Engelson et al. |
| 6,068,645 A | 5/2000 | Tu |
| 6,126,635 A | 10/2000 | Simpson et al. |
| 6,142,987 A | 11/2000 | Tsugita |
| 6,146,396 A | 11/2000 | Konya et al. |
| 6,146,403 A | 11/2000 | St. Germain |
| 6,152,144 A | 11/2000 | Lesh et al. |
| 6,152,909 A | 11/2000 | Bagaoisan et al. |
| 6,152,946 A | 11/2000 | Broome et al. |
| 6,156,055 A | 12/2000 | Ravenscroft |
| 6,159,230 A | 12/2000 | Samuels |
| 6,165,196 A | 12/2000 | Stack et al. |
| 6,168,579 B1 | 1/2001 | Tsugita |
| 6,179,859 B1 | 1/2001 | Bates et al. |
| 6,221,006 B1 | 4/2001 | Dubrul et al. |
| 6,228,060 B1 | 5/2001 | Howell |
| 6,238,412 B1 | 5/2001 | Dubrul et al. |
| 6,245,078 B1 | 6/2001 | Ouchi |
| 6,245,089 B1 | 6/2001 | Daniel et al. |
| 6,254,571 B1 | 7/2001 | Hart |
| 6,258,115 B1 | 7/2001 | Dubrul |
| 6,264,663 B1 | 7/2001 | Cano |
| 6,306,163 B1 | 10/2001 | Fitz |
| 6,322,572 B1 | 11/2001 | Lee |
| 6,350,271 B1 | 2/2002 | Kurz et al. |
| 6,361,545 B1 | 3/2002 | Macoviak et al. |
| 6,364,895 B1 | 4/2002 | Greenhalgh |
| 6,368,339 B1 | 4/2002 | Amplatz |
| 6,383,205 B1 | 5/2002 | Samson et al. |
| 6,402,771 B1 | 6/2002 | Palmer et al. |
| 6,413,235 B1 | 7/2002 | Parodi |
| 6,423,032 B2 | 7/2002 | Parodi |
| 6,432,122 B1 | 8/2002 | Gilson et al. |
| 6,436,085 B1 | 8/2002 | Lauer |
| 6,451,036 B1 | 9/2002 | Heitzmann et al. |
| 6,458,103 B1 | 10/2002 | Albert et al. |
| 6,475,236 B1 | 11/2002 | Roubin et al. |
| 6,485,502 B2 | 11/2002 | Don Michael |
| 6,508,782 B1 | 1/2003 | Evans et al. |
| 6,511,492 B1 | 1/2003 | Rosenbluth et al. |
| 6,514,273 B1 | 2/2003 | Voss et al. |
| 6,530,923 B1 | 3/2003 | Dubrul et al. |
| 6,530,935 B2 | 3/2003 | Wensel et al. |
| 6,540,722 B1 | 4/2003 | Boyle et al. |
| 6,544,276 B1 | 4/2003 | Azizi |
| 6,544,278 B1 | 4/2003 | Vrba et al. |
| 6,544,279 B1 | 4/2003 | Hopkins et al. |
| 6,551,342 B1 | 4/2003 | Shen et al. |
| 6,564,828 B1 | 5/2003 | Ishida |
| 6,569,181 B1 | 5/2003 | Burns |
| 6,575,995 B1 | 6/2003 | Huter et al. |
| 6,589,263 B1 | 7/2003 | Hopkins et al. |
| 6,589,264 B1 | 7/2003 | Barbut et al. |
| 6,596,011 B2 | 7/2003 | Johnson et al. |
| 6,602,271 B2 | 8/2003 | Adams et al. |
| 6,605,074 B2 | 8/2003 | Zadno-azizi et al. |
| 6,605,102 B1 | 8/2003 | Mazzocchi et al. |
| 6,610,077 B1 | 8/2003 | Hancock et al. |
| 6,620,148 B1 | 9/2003 | Tsugita |
| 6,620,179 B2 | 9/2003 | Brook et al. |
| 6,620,182 B1 | 9/2003 | Khosravi et al. |
| 6,623,460 B1 | 9/2003 | Heck |
| 6,635,068 B1 | 10/2003 | Dubrul et al. |
| 6,645,222 B1 | 11/2003 | Parodi et al. |
| 6,660,013 B2 | 12/2003 | Rabiner et al. |
| 6,660,014 B2 | 12/2003 | Demarais et al. |
| 6,663,650 B2 | 12/2003 | Sepetka et al. |
| 6,692,504 B2 | 2/2004 | Kurz et al. |
| 6,699,260 B2 | 3/2004 | Dubrul et al. |
| 6,702,830 B1 | 3/2004 | Demarais et al. |
| 6,719,717 B1 | 4/2004 | Johnson et al. |
| 6,755,847 B2 | 6/2004 | Eskuri |
| 6,767,353 B1 | 7/2004 | Shiber |
| 6,790,204 B2 | 9/2004 | Zadno-azizi et al. |
| 6,800,080 B1 | 10/2004 | Bates |
| 6,818,006 B2 | 11/2004 | Douk et al. |
| 6,824,545 B2 | 11/2004 | Sepetka et al. |
| 6,824,550 B1 | 11/2004 | Noriega et al. |
| 6,824,553 B1 | 11/2004 | Gene et al. |
| 6,830,561 B2 | 12/2004 | Jansen et al. |
| 6,846,029 B1 | 1/2005 | Ragner et al. |
| 6,902,540 B2 | 6/2005 | Dorros et al. |
| 6,908,455 B2 | 6/2005 | Hajianpour |
| 6,939,361 B1 | 9/2005 | Kleshinski |
| 6,942,682 B2 | 9/2005 | Vrba et al. |
| 6,945,977 B2 | 9/2005 | Demarais et al. |
| 6,960,189 B2 | 11/2005 | Bates et al. |
| 6,960,222 B2 | 11/2005 | Vo et al. |
| 7,004,931 B2 | 2/2006 | Hogendijk |
| 7,004,954 B1 | 2/2006 | Voss et al. |
| 7,036,707 B2 | 5/2006 | Aota et al. |
| 7,041,084 B2 | 5/2006 | Fotjik |
| 7,052,500 B2 | 5/2006 | Bashiri et al. |
| 7,056,328 B2 | 6/2006 | Arnott |
| 7,063,707 B2 | 6/2006 | Bose et al. |
| 7,069,835 B2 | 7/2006 | Nishri et al. |
| 7,094,249 B1 | 8/2006 | Thomas et al. |
| 7,122,034 B2 | 10/2006 | Belhe et al. |
| 7,128,073 B1 | 10/2006 | van der Burg et al. |
| 7,152,605 B2 | 12/2006 | Khairkhahan et al. |
| 7,179,273 B1 | 2/2007 | Palmer et al. |
| 7,223,253 B2 | 5/2007 | Hogendijk |
| 7,232,432 B2 | 6/2007 | Fulton, III et al. |
| 7,244,243 B2 | 7/2007 | Lary |
| 7,285,126 B2 | 10/2007 | Sepetka et al. |
| 7,300,458 B2 | 11/2007 | Henkes et al. |
| 7,306,618 B2 | 12/2007 | Demond et al. |
| 7,320,698 B2 | 1/2008 | Eskuri |
| 7,323,002 B2 | 1/2008 | Johnson et al. |
| 7,331,980 B2 | 2/2008 | Dubrul et al. |
| 7,481,805 B2 | 1/2009 | Magnusson |
| 7,534,234 B2 | 5/2009 | Fotjik |
| 7,578,830 B2 | 8/2009 | Kusleika et al. |
| 7,621,870 B2 | 11/2009 | Berrada et al. |
| 7,674,247 B2 | 3/2010 | Fotjik |
| 7,678,131 B2 | 3/2010 | Muller |
| 7,691,121 B2 | 4/2010 | Rosenbluth et al. |
| 7,695,458 B2 | 4/2010 | Belley et al. |
| 7,713,282 B2 | 5/2010 | Frazier et al. |
| 7,722,641 B2 | 5/2010 | van der Burg et al. |
| 7,763,010 B2 | 7/2010 | Evans et al. |
| 7,766,934 B2 | 8/2010 | Pal et al. |
| 7,775,501 B2 | 8/2010 | Kees |
| 7,780,696 B2 | 8/2010 | Daniel et al. |
| 7,815,608 B2 | 10/2010 | Schafersman et al. |
| 7,837,630 B2 | 11/2010 | Nieoson et al. |
| 7,905,877 B1 | 3/2011 | Oscar et al. |
| 7,905,896 B2 | 3/2011 | Straub |
| 7,938,809 B2 | 5/2011 | Lampropoulos et al. |
| 7,938,820 B2 | 5/2011 | Webster et al. |
| 7,967,790 B2 | 6/2011 | Whiting et al. |
| 7,976,511 B2 | 7/2011 | Fotjik |
| 7,993,302 B2 | 8/2011 | Hebert et al. |
| 7,993,363 B2 | 8/2011 | Demond et al. |
| 8,021,351 B2 | 9/2011 | Boldenow et al. |
| 8,043,313 B2 | 10/2011 | Krolik et al. |
| 8,052,640 B2 | 11/2011 | Fiorella et al. |
| 8,057,496 B2 | 11/2011 | Fischer, Jr. |
| 8,057,497 B1 | 11/2011 | Raju et al. |
| 8,066,757 B2 | 11/2011 | Ferrera et al. |
| 8,070,694 B2 | 12/2011 | Galdonik et al. |
| 8,070,769 B2 | 12/2011 | Broome |
| 8,070,791 B2 | 12/2011 | Ferrera et al. |
| 8,075,510 B2 | 12/2011 | Aklog et al. |
| 8,080,032 B2 | 12/2011 | van der Burg et al. |
| 8,088,140 B2 | 1/2012 | Ferrera et al. |
| 8,092,486 B2 | 1/2012 | Berrada et al. |
| 8,100,935 B2 | 1/2012 | Rosenbluth et al. |
| 8,109,962 B2 | 2/2012 | Pal |
| 8,118,275 B2 | 2/2012 | Mialhe |
| 8,118,829 B2 | 2/2012 | Carrison et al. |

(56) References Cited

U.S. PATENT DOCUMENTS

| | | |
|---|---|---|
| 8,187,465 B2 | 5/2012 | Nierich |
| 8,197,493 B2 | 6/2012 | Ferrera et al. |
| 8,246,641 B2 | 8/2012 | Osborne et al. |
| 8,261,648 B1 | 9/2012 | Marchand et al. |
| 8,267,897 B2 | 9/2012 | Wells |
| 8,298,257 B2 | 10/2012 | Sepetka et al. |
| 8,317,748 B2 | 11/2012 | Fiorella et al. |
| 8,337,450 B2 | 12/2012 | Fotjik |
| RE43,902 E | 1/2013 | Hopkins et al. |
| 8,343,167 B2 | 1/2013 | Henson |
| 8,357,178 B2 | 1/2013 | Grandfield et al. |
| 8,361,104 B2 | 1/2013 | Jones et al. |
| 8,409,215 B2 | 4/2013 | Sepetka et al. |
| 8,439,858 B2 | 5/2013 | Huang et al. |
| 8,480,708 B2 | 7/2013 | Kassab et al. |
| 8,486,105 B2 | 7/2013 | Demond et al. |
| 8,491,539 B2 | 7/2013 | Fotjik |
| 8,512,352 B2 | 8/2013 | Martin |
| 8,523,897 B2 | 9/2013 | van der Burg et al. |
| 8,529,596 B2 | 9/2013 | Grandfield et al. |
| 8,535,283 B2 | 9/2013 | Heaton et al. |
| 8,535,334 B2 | 9/2013 | Martin |
| 8,535,343 B2 | 9/2013 | van der Burg et al. |
| 8,545,526 B2 | 10/2013 | Martin et al. |
| 8,568,432 B2 | 10/2013 | Straub |
| 8,568,465 B2 | 10/2013 | Freudenthal et al. |
| 8,574,262 B2 | 11/2013 | Ferrera et al. |
| 8,579,915 B2 | 11/2013 | French et al. |
| 8,585,713 B2 | 11/2013 | Ferrera et al. |
| 8,608,754 B2 | 12/2013 | Wensel et al. |
| 8,613,717 B2 | 12/2013 | Aklog et al. |
| 8,632,584 B2 | 1/2014 | Henkes et al. |
| 8,647,367 B2 | 2/2014 | Kassab et al. |
| 8,657,867 B2 | 2/2014 | Dorn et al. |
| 8,696,622 B2 | 4/2014 | Fiorella et al. |
| 8,715,314 B1 | 5/2014 | Janardhan et al. |
| 8,721,714 B2 | 5/2014 | Kelley |
| 8,753,322 B2 | 6/2014 | Hu et al. |
| 8,764,730 B2 | 7/2014 | Taber |
| 8,771,289 B2 | 7/2014 | Mohiuddin et al. |
| 8,777,893 B2 | 7/2014 | Malewicz |
| 8,784,441 B2 | 7/2014 | Rosenbluth et al. |
| 8,784,442 B2 | 7/2014 | Jones et al. |
| 8,784,469 B2 | 7/2014 | Kassab |
| 8,795,305 B2 | 8/2014 | Martin et al. |
| 8,795,317 B2 | 8/2014 | Grandfield et al. |
| 8,795,345 B2 | 8/2014 | Grandfield et al. |
| 8,801,748 B2 | 8/2014 | Martin |
| 8,808,259 B2 | 8/2014 | Walton et al. |
| 8,814,927 B2 | 8/2014 | Shin et al. |
| 8,820,207 B2 | 9/2014 | Marchand et al. |
| 8,826,791 B2 | 9/2014 | Thompson et al. |
| 8,828,044 B2 | 9/2014 | Aggerholm et al. |
| 8,833,224 B2 | 9/2014 | Thompson et al. |
| 8,834,519 B2 | 9/2014 | van der Burg et al. |
| 8,845,621 B2 | 9/2014 | Fotjik |
| 8,852,226 B2 | 10/2014 | Gilson et al. |
| 8,939,991 B2 | 1/2015 | Krolik et al. |
| 8,945,143 B2 | 2/2015 | Ferrera et al. |
| 8,945,172 B2 | 2/2015 | Ferrera et al. |
| 8,956,384 B2 | 2/2015 | Berrada et al. |
| 8,992,504 B2 | 3/2015 | Castella et al. |
| 9,005,172 B2 | 4/2015 | Chung |
| 9,011,551 B2 | 4/2015 | Oral et al. |
| 9,028,401 B1 | 5/2015 | Bacich et al. |
| 9,044,575 B2 | 6/2015 | Beasley et al. |
| 9,072,537 B2 | 7/2015 | Grandfield et al. |
| 9,078,682 B2 | 7/2015 | Lenker et al. |
| 9,101,382 B2 | 8/2015 | Krolik et al. |
| 9,125,683 B2 | 9/2015 | Farhangnia et al. |
| 9,126,016 B2 | 9/2015 | Fulton |
| 9,126,020 B2 | 9/2015 | Farhangnia et al. |
| 9,149,609 B2 | 10/2015 | Ansel et al. |
| 9,155,552 B2 | 10/2015 | Ulm, III |
| 9,161,766 B2 | 10/2015 | Slee et al. |
| 9,168,043 B2 | 10/2015 | van der Burg et al. |
| 9,173,668 B2 | 11/2015 | Ulm, III |
| 9,186,487 B2 | 11/2015 | Dubrul et al. |
| D744,639 S | 12/2015 | Aklog et al. |
| 9,204,887 B2 | 12/2015 | Cully et al. |
| 9,216,277 B2 | 12/2015 | Myers |
| 9,241,669 B2 | 1/2016 | Pugh et al. |
| 9,358,037 B2 | 1/2016 | Farhangnia et al. |
| 9,254,352 B2 | 2/2016 | Kumar et al. |
| 9,259,237 B2 | 2/2016 | Quick et al. |
| 9,265,512 B2 | 2/2016 | Carrison et al. |
| 9,283,066 B2 | 3/2016 | Hopkins et al. |
| 9,301,769 B2 | 4/2016 | Brady et al. |
| 9,351,747 B2 | 5/2016 | Kugler et al. |
| 9,402,938 B2 | 8/2016 | Aklog et al. |
| 9,439,664 B2 | 9/2016 | Sos |
| 9,439,751 B2 | 9/2016 | White et al. |
| 9,456,834 B2 | 10/2016 | Folk |
| 9,463,035 B1 | 10/2016 | Greenhalgh et al. |
| 9,463,036 B2 | 10/2016 | Brady et al. |
| 9,492,635 B2 | 11/2016 | Beasley et al. |
| 9,526,864 B2 | 12/2016 | Quick |
| 9,526,865 B2 | 12/2016 | Quick |
| 9,532,792 B2 | 1/2017 | Galdonik et al. |
| 9,545,464 B2 | 1/2017 | Roche et al. |
| 9,566,073 B2 | 2/2017 | Kassab et al. |
| 9,566,179 B2 | 2/2017 | Andreas et al. |
| 9,566,424 B2 | 2/2017 | Pessin |
| 9,579,116 B1 | 2/2017 | Nguyen et al. |
| 9,581,942 B1 | 2/2017 | Shippert |
| 9,616,213 B2 | 4/2017 | Furnish et al. |
| 9,636,206 B2 | 5/2017 | Nguyen et al. |
| 9,643,035 B2 | 5/2017 | Mastenbroek |
| 9,662,129 B2 | 5/2017 | Galdonik et al. |
| 9,700,332 B2 | 7/2017 | Marchand et al. |
| 9,717,488 B2 | 8/2017 | Kassab et al. |
| 9,717,514 B2 | 8/2017 | Martin et al. |
| 9,717,519 B2 | 8/2017 | Rosenbluth et al. |
| 9,744,024 B2 | 8/2017 | Nguyen et al. |
| 9,757,137 B2 | 9/2017 | Krolik et al. |
| 9,827,084 B2 | 11/2017 | Bonnette et al. |
| 9,827,364 B2 | 11/2017 | Peticca et al. |
| 9,844,386 B2 | 12/2017 | Nguyen et al. |
| 9,844,387 B2 | 12/2017 | Marchand et al. |
| 9,844,643 B2 | 12/2017 | Beasley et al. |
| 9,848,975 B2 | 12/2017 | Hauser |
| 9,849,014 B2 | 12/2017 | Kusleika |
| 9,884,387 B2 | 2/2018 | Plha |
| 9,937,321 B2 | 4/2018 | Welch et al. |
| 9,962,178 B2 | 5/2018 | Greenhalgh et al. |
| 9,980,813 B2 | 5/2018 | Eller |
| 9,999,493 B2 | 6/2018 | Nguyen et al. |
| 10,004,531 B2 | 6/2018 | Rosenbluth et al. |
| 10,010,335 B2 | 7/2018 | Greenhalgh et al. |
| 10,016,206 B1 | 7/2018 | Yang |
| 10,016,266 B2 | 7/2018 | Hauser |
| 10,028,759 B2 | 7/2018 | Wallace et al. |
| 10,045,790 B2 | 8/2018 | Cox et al. |
| 10,058,339 B2 | 8/2018 | Galdonik et al. |
| 10,098,651 B2 | 10/2018 | Marchand et al. |
| 10,130,385 B2 | 11/2018 | Farhangnia et al. |
| 10,130,795 B2 | 11/2018 | Parhangnia et al. |
| 10,179,224 B2 | 1/2019 | Yang et al. |
| 10,183,147 B2 | 1/2019 | Yang et al. |
| 10,183,159 B2 | 1/2019 | Nobles et al. |
| 10,188,829 B2 | 1/2019 | Beasley et al. |
| 10,195,320 B2 | 2/2019 | Fisher et al. |
| 10,226,263 B2 | 3/2019 | Look et al. |
| 10,238,406 B2 | 3/2019 | Cox et al. |
| 10,271,864 B2 | 4/2019 | Greenhalgh et al. |
| 10,327,883 B2 | 6/2019 | Yachia |
| 10,335,186 B2 | 7/2019 | Rosenbluth et al. |
| 10,342,571 B2 | 7/2019 | Marchand et al. |
| 10,349,960 B2 | 7/2019 | Quick |
| 10,383,644 B2 | 8/2019 | Molaei et al. |
| 10,383,983 B2 | 8/2019 | Aklog et al. |
| 10,384,034 B2 | 8/2019 | Carrison et al. |
| 10,426,510 B2 | 10/2019 | Farhangnia et al. |
| 10,426,644 B2 | 10/2019 | Shrivastava et al. |

(56) References Cited

U.S. PATENT DOCUMENTS

| | | |
|---|---|---|
| 10,441,745 B2 | 10/2019 | Yang et al. |
| 10,456,151 B2 | 10/2019 | Slee et al. |
| 10,456,555 B2 | 10/2019 | Carrison et al. |
| 10,471,234 B2 | 11/2019 | Taber |
| 10,478,535 B2 | 11/2019 | Ogle |
| 10,485,952 B2 | 11/2019 | Carrison et al. |
| 10,492,805 B2 | 12/2019 | Culbert et al. |
| 10,524,811 B2 | 1/2020 | Marchand et al. |
| 10,531,883 B1 | 1/2020 | Deville et al. |
| 10,537,710 B2 | 1/2020 | Jalgaonkar et al. |
| 10,561,440 B2 | 2/2020 | Look et al. |
| 10,588,655 B2 | 3/2020 | Rosenbluth et al. |
| 10,648,268 B2 | 5/2020 | Jaffrey et al. |
| 10,661,053 B2 | 5/2020 | Yang et al. |
| 10,695,159 B2 | 6/2020 | Hauser |
| 10,709,471 B2 | 7/2020 | Rosenbluth et al. |
| 10,729,455 B2 | 8/2020 | Goyal et al. |
| 10,743,907 B2 | 8/2020 | Bruzzi et al. |
| 10,772,636 B2 | 9/2020 | Kassab et al. |
| 10,779,852 B2 | 9/2020 | Bruzzi et al. |
| 10,779,855 B2 | 9/2020 | Garrison |
| 10,799,331 B2 | 10/2020 | Hauser |
| 10,799,671 B2 | 10/2020 | Shimada et al. |
| 10,813,663 B2 | 10/2020 | Bruzzi et al. |
| 10,828,061 B2 | 11/2020 | Bonnette et al. |
| 10,835,711 B2 | 11/2020 | Yang et al. |
| 10,874,421 B2 | 12/2020 | Bruzzi et al. |
| 10,912,577 B2 | 2/2021 | Marchand et al. |
| 10,926,060 B2 | 2/2021 | Stern et al. |
| 10,939,932 B1 | 3/2021 | Yang |
| 10,953,195 B2 | 3/2021 | Jalgaonkar et al. |
| 10,960,114 B2 | 3/2021 | Goisis |
| 10,967,111 B2 | 4/2021 | Tida |
| 10,994,063 B2 | 5/2021 | Fisher et al. |
| 11,000,682 B2 | 5/2021 | Merritt et al. |
| 11,013,523 B2 | 5/2021 | Arad Hadar |
| 11,058,445 B2 | 7/2021 | Cox et al. |
| 11,058,451 B2 | 7/2021 | Marchand et al. |
| 11,065,019 B1 | 7/2021 | Chou et al. |
| 11,065,028 B2 | 7/2021 | Parhangnia et al. |
| 11,147,571 B2 | 10/2021 | Cox et al. |
| 11,147,948 B2 | 10/2021 | Beasley et al. |
| 11,147,949 B2 | 10/2021 | Yang et al. |
| 11,154,314 B2 | 10/2021 | Quick |
| 11,166,703 B2 | 11/2021 | Kassab et al. |
| 11,185,664 B2 | 11/2021 | Carrison et al. |
| 11,197,684 B1 | 12/2021 | Ngo et al. |
| 11,213,356 B2 | 1/2022 | Tanner et al. |
| 11,224,450 B2 | 1/2022 | Chou et al. |
| 11,224,721 B2 | 1/2022 | Carrison et al. |
| 11,253,277 B2 | 2/2022 | Buck et al. |
| 11,259,821 B2 | 3/2022 | Buck et al. |
| 11,266,825 B2 | 3/2022 | Peter et al. |
| 11,278,307 B2 | 3/2022 | Bruzzi et al. |
| 11,305,094 B2 | 4/2022 | Carrison et al. |
| 11,317,939 B2 | 5/2022 | Bruzzi et al. |
| 11,337,714 B2 | 5/2022 | Ferrera et al. |
| 11,383,064 B2 | 7/2022 | Carrison et al. |
| 11,395,903 B2 | 7/2022 | Carrison et al. |
| 11,406,418 B2 | 8/2022 | Bruzzi et al. |
| 11,406,801 B2 | 8/2022 | Fojtik et al. |
| 11,419,621 B2 | 8/2022 | Goyal et al. |
| 11,433,218 B2 | 9/2022 | Quick et al. |
| 11,439,799 B2 | 9/2022 | Buck et al. |
| 11,457,936 B2 | 10/2022 | Buck et al. |
| 11,478,262 B2 | 10/2022 | Ngo et al. |
| 11,529,158 B2 | 12/2022 | Hauser |
| 11,553,935 B2 | 1/2023 | Buck et al. |
| 11,553,942 B2 | 1/2023 | Bonnette et al. |
| 11,554,005 B2 | 1/2023 | Merritt et al. |
| 11,559,382 B2 | 1/2023 | Merritt et al. |
| 11,576,691 B2 | 2/2023 | Chou et al. |
| 11,589,880 B2 | 2/2023 | Aklog et al. |
| 11,596,768 B2 | 3/2023 | Stern et al. |
| 11,607,483 B2 | 3/2023 | Tida |
| 11,633,272 B2 | 4/2023 | Buck et al. |
| 11,638,637 B2 | 5/2023 | Buck et al. |
| 11,642,209 B2 | 5/2023 | Merritt et al. |
| 11,648,028 B2 | 5/2023 | Rosenbluth et al. |
| 11,672,561 B2 | 6/2023 | Look et al. |
| 11,697,011 B2 | 7/2023 | Merritt et al. |
| 11,697,012 B2 | 7/2023 | Merritt et al. |
| 11,744,691 B2 | 9/2023 | Merritt et al. |
| 11,806,033 B2 | 11/2023 | Marchand et al. |
| 11,819,228 B2 | 11/2023 | Buck et al. |
| 11,832,837 B2 | 12/2023 | Hauser |
| 11,832,838 B2 | 12/2023 | Hauser |
| 11,833,023 B2 | 12/2023 | Hauser |
| 11,839,393 B2 | 12/2023 | Hauser |
| 11,844,921 B2 | 12/2023 | Merritt et al. |
| 11,849,963 B2 | 12/2023 | Quick |
| 11,865,291 B2 | 1/2024 | Merritt et al. |
| 11,890,180 B2 | 2/2024 | Merritt et al. |
| 11,918,243 B2 | 3/2024 | Marchand et al. |
| 11,918,244 B2 | 3/2024 | Marchand et al. |
| 11,925,369 B2 | 3/2024 | Hauser |
| 11,937,834 B2 | 3/2024 | Dinh |
| 11,937,838 B2 | 3/2024 | Cox et al. |
| 11,963,861 B2 | 4/2024 | Strauss et al. |
| 11,969,178 B2 | 4/2024 | Hauser |
| 11,969,331 B2 | 4/2024 | Merritt et al. |
| 11,969,332 B2 | 4/2024 | Merritt et al. |
| 11,969,333 B2 | 4/2024 | Merritt et al. |
| 11,974,909 B2 | 5/2024 | Merritt et al. |
| 11,974,910 B2 | 5/2024 | Merritt et al. |
| 11,980,537 B2 | 5/2024 | Merritt et al. |
| 11,986,382 B2 | 5/2024 | Merritt et al. |
| 11,998,436 B2 | 6/2024 | Merritt et al. |
| 12,016,580 B2 | 6/2024 | Quick et al. |
| 12,023,057 B2 | 7/2024 | Hauser |
| 12,102,343 B2 | 10/2024 | Quick |
| 2001/0004699 A1 | 6/2001 | Gittings et al. |
| 2001/0031981 A1 | 10/2001 | Evans et al. |
| 2001/0041881 A1 | 11/2001 | Sarge et al. |
| 2001/0041909 A1 | 11/2001 | Tsugita et al. |
| 2001/0049486 A1 | 12/2001 | Evans et al. |
| 2001/0051810 A1 | 12/2001 | Dubrul et al. |
| 2002/0022858 A1 | 2/2002 | Demond et al. |
| 2002/0022859 A1 | 2/2002 | Hogendijk |
| 2002/0026211 A1 | 2/2002 | Khosravi et al. |
| 2002/0032455 A1 | 3/2002 | Boock et al. |
| 2002/0049452 A1 | 4/2002 | Kurz et al. |
| 2002/0095161 A1 | 7/2002 | Dhindsa |
| 2002/0095171 A1 | 7/2002 | Belef |
| 2002/0111648 A1 | 8/2002 | Kusleika et al. |
| 2002/0120277 A1 | 8/2002 | Hauschild et al. |
| 2002/0147458 A1 | 10/2002 | Hiblar et al. |
| 2002/0151918 A1 | 10/2002 | Lafontaine et al. |
| 2002/0156457 A1 | 10/2002 | Fisher |
| 2002/0161392 A1 | 10/2002 | Dubrul |
| 2002/0169474 A1 | 11/2002 | Kusleika |
| 2002/0173819 A1 | 11/2002 | Leeflang et al. |
| 2002/0188276 A1 | 12/2002 | Evans et al. |
| 2003/0004536 A1 | 1/2003 | Boylan et al. |
| 2003/0023263 A1 | 1/2003 | Krolik et al. |
| 2003/0069601 A1 | 4/2003 | Nowakowski et al. |
| 2003/0083693 A1 | 5/2003 | Daniel et al. |
| 2003/0100919 A1 | 5/2003 | Hopkins et al. |
| 2003/0114875 A1 | 6/2003 | Sjostrom |
| 2003/0116731 A1 | 6/2003 | Hartley |
| 2003/0125663 A1 | 7/2003 | Coleman et al. |
| 2003/0135151 A1 | 7/2003 | Deng |
| 2003/0135230 A1 | 7/2003 | Massey et al. |
| 2003/0135258 A1 | 7/2003 | Andreas et al. |
| 2003/0153873 A1 | 8/2003 | Luther et al. |
| 2003/0153973 A1 | 8/2003 | Soun et al. |
| 2003/0168068 A1 | 9/2003 | Poole et al. |
| 2003/0176884 A1 | 9/2003 | Berrada et al. |
| 2003/0191425 A1 | 10/2003 | Rosenblatt et al. |
| 2003/0191516 A1 | 10/2003 | Weldon et al. |
| 2003/0208224 A1 | 11/2003 | Broome |
| 2003/0216774 A1 | 11/2003 | Larson |
| 2003/0225379 A1 | 12/2003 | Schaffer et al. |
| 2004/0019310 A1 | 1/2004 | Hogendijk |

(56) References Cited

U.S. PATENT DOCUMENTS

| | | |
|---|---|---|
| 2004/0039351 A1 | 2/2004 | Barrett |
| 2004/0039412 A1 | 2/2004 | Isshiki et al. |
| 2004/0068288 A1 | 4/2004 | Palmer et al. |
| 2004/0073243 A1 | 4/2004 | Sepetka et al. |
| 2004/0098033 A1 | 5/2004 | Leeflang et al. |
| 2004/0102807 A1 | 5/2004 | Kusleika et al. |
| 2004/0122359 A1 | 6/2004 | Wenz et al. |
| 2004/0127936 A1 | 7/2004 | Salahieh et al. |
| 2004/0133232 A1 | 7/2004 | Rosenbluth et al. |
| 2004/0138525 A1 | 7/2004 | Saadat et al. |
| 2004/0138692 A1 | 7/2004 | Phung et al. |
| 2004/0167567 A1 | 8/2004 | Cano et al. |
| 2004/0199201 A1 | 10/2004 | Kellett et al. |
| 2004/0199202 A1 | 10/2004 | Dubrul et al. |
| 2004/0260344 A1 | 12/2004 | Lyons et al. |
| 2004/0267272 A1 | 12/2004 | Henniges et al. |
| 2005/0004534 A1 | 1/2005 | Lockwood et al. |
| 2005/0033172 A1 | 2/2005 | Dubrul et al. |
| 2005/0038468 A1 | 2/2005 | Panetta et al. |
| 2005/0054995 A1 | 3/2005 | Barzell et al. |
| 2005/0055047 A1 | 3/2005 | Greenhalgh |
| 2005/0080398 A1 | 4/2005 | Markel et al. |
| 2005/0085769 A1 | 4/2005 | MacMahon et al. |
| 2005/0085826 A1 | 4/2005 | Nair et al. |
| 2005/0085846 A1 | 4/2005 | Carrison et al. |
| 2005/0085849 A1 | 4/2005 | Sepetka et al. |
| 2005/0119668 A1 | 6/2005 | Teague et al. |
| 2005/0131387 A1 | 6/2005 | Pursley |
| 2005/0177132 A1 | 8/2005 | Lentz et al. |
| 2005/0187570 A1 | 8/2005 | Nguyen et al. |
| 2005/0203605 A1 | 9/2005 | Dolan |
| 2005/0283165 A1 | 12/2005 | Gadberry |
| 2005/0283166 A1 | 12/2005 | Greenhalgh et al. |
| 2005/0283186 A1 | 12/2005 | Berrada et al. |
| 2006/0020286 A1 | 1/2006 | Niermann |
| 2006/0042786 A1 | 3/2006 | West |
| 2006/0047286 A1 | 3/2006 | West |
| 2006/0074401 A1 | 4/2006 | Ross |
| 2006/0079787 A1 | 4/2006 | Whiting et al. |
| 2006/0085952 A1 | 4/2006 | Kaneko et al. |
| 2006/0089533 A1 | 4/2006 | Ziegler et al. |
| 2006/0100662 A1 | 5/2006 | Daniel et al. |
| 2006/0149219 A1 | 7/2006 | Calderon |
| 2006/0155305 A1 | 7/2006 | Freudenthal et al. |
| 2006/0173525 A1 | 8/2006 | Behl et al. |
| 2006/0195137 A1 | 8/2006 | Sepetka et al. |
| 2006/0200221 A1 | 9/2006 | Malewicz |
| 2006/0217664 A1 | 9/2006 | Hattler et al. |
| 2006/0224177 A1 | 10/2006 | Finitsis |
| 2006/0229645 A1 | 10/2006 | Bonnette et al. |
| 2006/0247500 A1 | 11/2006 | Voegele et al. |
| 2006/0253145 A1 | 11/2006 | Lucas |
| 2006/0264905 A1 | 11/2006 | Eskridge et al. |
| 2006/0276874 A1 | 12/2006 | Wilson et al. |
| 2006/0282111 A1 | 12/2006 | Morsi |
| 2006/0293696 A1 | 12/2006 | Fahey et al. |
| 2007/0010787 A1 | 1/2007 | Hackett et al. |
| 2007/0038225 A1 | 2/2007 | Osborne |
| 2007/0093744 A1 | 4/2007 | Elmaleh |
| 2007/0112374 A1 | 5/2007 | Paul, Jr. et al. |
| 2007/0118165 A1 | 5/2007 | DeMello et al. |
| 2007/0149996 A1 | 6/2007 | Coughlin |
| 2007/0161963 A1 | 7/2007 | Smalling |
| 2007/0179513 A1 | 8/2007 | Deutsch |
| 2007/0191866 A1 | 8/2007 | Palmer et al. |
| 2007/0198028 A1 | 8/2007 | Miloslavski et al. |
| 2007/0208361 A1 | 9/2007 | Okushi et al. |
| 2007/0208367 A1 | 9/2007 | Fiorella et al. |
| 2007/0213753 A1 | 9/2007 | Waller |
| 2007/0213765 A1 | 9/2007 | Adams et al. |
| 2007/0233043 A1 | 10/2007 | Dayton et al. |
| 2007/0255252 A1 | 11/2007 | Mehta |
| 2007/0288054 A1 | 12/2007 | Tanaka et al. |
| 2008/0015541 A1 | 1/2008 | Rosenbluth et al. |
| 2008/0087853 A1 | 4/2008 | Kees |
| 2008/0088055 A1 | 4/2008 | Ross |
| 2008/0157017 A1 | 7/2008 | Macatangay et al. |
| 2008/0167678 A1 | 7/2008 | Morsi |
| 2008/0183136 A1 | 7/2008 | Lenker et al. |
| 2008/0228209 A1 | 9/2008 | DeMello et al. |
| 2008/0234715 A1 | 9/2008 | Pesce et al. |
| 2008/0234722 A1 | 9/2008 | Bonnette et al. |
| 2008/0262528 A1 | 10/2008 | Martin |
| 2008/0269798 A1 | 10/2008 | Ramzipoor et al. |
| 2008/0294096 A1 | 11/2008 | Uber, III et al. |
| 2008/0300466 A1 | 12/2008 | Gresham |
| 2008/0312681 A1 | 12/2008 | Ansel et al. |
| 2009/0018566 A1 | 1/2009 | Escudero et al. |
| 2009/0054918 A1 | 2/2009 | Henson |
| 2009/0062841 A1 | 3/2009 | Amplatz et al. |
| 2009/0069828 A1 | 3/2009 | Martin et al. |
| 2009/0076417 A1 | 3/2009 | Jones |
| 2009/0082857 A1 | 3/2009 | Lashinski et al. |
| 2009/0160112 A1 | 6/2009 | Ostrovsky |
| 2009/0163846 A1 | 6/2009 | Aklog et al. |
| 2009/0182362 A1 | 7/2009 | Thompson et al. |
| 2009/0192495 A1 | 7/2009 | Ostrovsky et al. |
| 2009/0281525 A1 | 11/2009 | Harding et al. |
| 2009/0292307 A1 | 11/2009 | Razack |
| 2009/0299393 A1 | 12/2009 | Martin et al. |
| 2009/0312786 A1 | 12/2009 | Trask et al. |
| 2010/0016837 A1 | 1/2010 | Howat |
| 2010/0030256 A1 | 2/2010 | Dubrul et al. |
| 2010/0042136 A1 | 2/2010 | Berrada et al. |
| 2010/0087844 A1 | 4/2010 | Fischer, Jr. |
| 2010/0087850 A1 | 4/2010 | Razack |
| 2010/0094201 A1 | 4/2010 | Mallaby |
| 2010/0106081 A1 | 4/2010 | Brandeis |
| 2010/0114017 A1 | 5/2010 | Lenker et al. |
| 2010/0114113 A1 | 5/2010 | Dubrul et al. |
| 2010/0121312 A1 | 5/2010 | Gielenz et al. |
| 2010/0137846 A1 | 6/2010 | Desai |
| 2010/0190156 A1 | 7/2010 | Van Wordragen et al. |
| 2010/0204712 A1 | 8/2010 | Mallaby |
| 2010/0217276 A1 | 8/2010 | Garrison et al. |
| 2010/0249815 A1 | 9/2010 | Jantzen et al. |
| 2010/0268264 A1 | 10/2010 | Bonnette et al. |
| 2010/0318178 A1 | 12/2010 | Rapaport et al. |
| 2011/0009950 A1 | 1/2011 | Grandfield et al. |
| 2011/0034986 A1 | 2/2011 | Chou et al. |
| 2011/0034987 A1 | 2/2011 | Kennedy |
| 2011/0054405 A1 | 3/2011 | Whiting et al. |
| 2011/0060212 A1 | 3/2011 | Slee et al. |
| 2011/0071503 A1 | 3/2011 | Takagi et al. |
| 2011/0087173 A1 | 4/2011 | Sibbitt, Jr. et al. |
| 2011/0118817 A1 | 5/2011 | Gunderson et al. |
| 2011/0125181 A1 | 5/2011 | Brady et al. |
| 2011/0144592 A1 | 6/2011 | Wong et al. |
| 2011/0152823 A1 | 6/2011 | Mohiuddin et al. |
| 2011/0152889 A1 | 6/2011 | Ashland |
| 2011/0152993 A1 | 6/2011 | Marchand et al. |
| 2011/0160742 A1 | 6/2011 | Ferrera et al. |
| 2011/0160763 A1 | 6/2011 | Ferrera et al. |
| 2011/0190806 A1 | 8/2011 | Wittens |
| 2011/0196309 A1 | 8/2011 | Wells |
| 2011/0196414 A1 | 8/2011 | Porter et al. |
| 2011/0213290 A1 | 9/2011 | Chin et al. |
| 2011/0213403 A1 | 9/2011 | Aboytes |
| 2011/0224707 A1 | 9/2011 | Miloslavski et al. |
| 2011/0245807 A1 | 10/2011 | Sakata et al. |
| 2011/0251629 A1 | 10/2011 | Galdonik et al. |
| 2011/0264132 A1 | 10/2011 | Strauss et al. |
| 2011/0264133 A1 | 10/2011 | Hanlon et al. |
| 2011/0265681 A1 | 11/2011 | Allen et al. |
| 2011/0288529 A1 | 11/2011 | Fulton |
| 2011/0288572 A1 | 11/2011 | Martin |
| 2011/0309037 A1 | 12/2011 | Lee |
| 2011/0319917 A1 | 12/2011 | Ferrera et al. |
| 2012/0059309 A1 | 3/2012 | di Palma et al. |
| 2012/0059356 A1 | 3/2012 | di Palma et al. |
| 2012/0083824 A1 | 4/2012 | Berrada et al. |
| 2012/0083868 A1 | 4/2012 | Shrivastava |
| 2012/0089216 A1 | 4/2012 | Rapaport et al. |
| 2012/0095448 A1 | 4/2012 | Kajii |

(56) References Cited

U.S. PATENT DOCUMENTS

| | | |
|---|---|---|
| 2012/0101480 A1 | 4/2012 | Ingle et al. |
| 2012/0101510 A1 | 4/2012 | Lenker et al. |
| 2012/0109109 A1 | 5/2012 | Kajii |
| 2012/0138832 A1 | 6/2012 | Townsend |
| 2012/0143123 A1 | 6/2012 | Agnew |
| 2012/0143239 A1 | 6/2012 | Aklog et al. |
| 2012/0165919 A1 | 6/2012 | Cox et al. |
| 2012/0172918 A1 | 7/2012 | Fifer et al. |
| 2012/0179181 A1 | 7/2012 | Straub et al. |
| 2012/0197277 A1 | 8/2012 | Stinis |
| 2012/0232655 A1 | 9/2012 | Lorrison et al. |
| 2012/0271105 A1 | 10/2012 | Nakamura et al. |
| 2012/0271231 A1 | 10/2012 | Agrawal |
| 2012/0277788 A1 | 11/2012 | Cattaneo |
| 2012/0310166 A1 | 12/2012 | Huff |
| 2013/0030460 A1 | 1/2013 | Marks et al. |
| 2013/0035628 A1 | 2/2013 | Garrison et al. |
| 2013/0046332 A1 | 2/2013 | Jones et al. |
| 2013/0066348 A1 | 3/2013 | Fiorella et al. |
| 2013/0092012 A1 | 4/2013 | Marchand et al. |
| 2013/0096571 A1 | 4/2013 | Massicotte et al. |
| 2013/0102996 A1 | 4/2013 | Strauss |
| 2013/0116708 A1 | 5/2013 | Ziniti et al. |
| 2013/0116721 A1 | 5/2013 | Takagi et al. |
| 2013/0123705 A1 | 5/2013 | Holm et al. |
| 2013/0126559 A1 | 5/2013 | Cowan et al. |
| 2013/0144326 A1 | 6/2013 | Brady et al. |
| 2013/0150793 A1 | 6/2013 | Beissel et al. |
| 2013/0165871 A1 | 6/2013 | Fiorella et al. |
| 2013/0184703 A1 | 7/2013 | Shireman et al. |
| 2013/0190701 A1 | 7/2013 | Kirn |
| 2013/0197454 A1 | 8/2013 | Shibata et al. |
| 2013/0197567 A1 | 8/2013 | Brady et al. |
| 2013/0204297 A1 | 8/2013 | Melsheimer et al. |
| 2013/0226196 A1 | 8/2013 | Smith |
| 2013/0270161 A1 | 10/2013 | Kumar et al. |
| 2013/0281788 A1 | 10/2013 | Garrison |
| 2013/0289608 A1 | 10/2013 | Tanaka et al. |
| 2013/0317589 A1 | 11/2013 | Martin et al. |
| 2013/0345739 A1 | 12/2013 | Brady et al. |
| 2014/0005712 A1 | 1/2014 | Martin |
| 2014/0005713 A1 | 1/2014 | Bowman |
| 2014/0005715 A1 | 1/2014 | Castella et al. |
| 2014/0005717 A1 | 1/2014 | Martin et al. |
| 2014/0025048 A1 | 1/2014 | Ward |
| 2014/0031856 A1 | 1/2014 | Martin |
| 2014/0046133 A1 | 2/2014 | Nakamura et al. |
| 2014/0046243 A1 | 2/2014 | Ray et al. |
| 2014/0052161 A1 | 2/2014 | Cully et al. |
| 2014/0074144 A1 | 3/2014 | Shrivastava et al. |
| 2014/0121672 A1 | 5/2014 | Folk |
| 2014/0155830 A1 | 6/2014 | Bonnette et al. |
| 2014/0155980 A1 | 6/2014 | Turjman |
| 2014/0163615 A1 | 6/2014 | Gadlage et al. |
| 2014/0180055 A1 | 6/2014 | Glynn et al. |
| 2014/0180397 A1 | 6/2014 | Gerberding et al. |
| 2014/0155908 A1 | 7/2014 | Rosenbluth et al. |
| 2014/0188127 A1 | 7/2014 | Dubrul et al. |
| 2014/0188143 A1 | 7/2014 | Martin et al. |
| 2014/0222070 A1 | 8/2014 | Belson et al. |
| 2014/0236219 A1 | 8/2014 | Dubrul et al. |
| 2014/0243882 A1 | 8/2014 | Ma |
| 2014/0257253 A1 | 9/2014 | Jemison |
| 2014/0257363 A1 | 9/2014 | Lippert |
| 2014/0276403 A1 | 9/2014 | Follmer et al. |
| 2014/0276592 A1 | 9/2014 | Mottola et al. |
| 2014/0296868 A1 | 10/2014 | Garrison et al. |
| 2014/0303658 A1 | 10/2014 | Bonnette et al. |
| 2014/0318354 A1 | 10/2014 | Thompson et al. |
| 2014/0324091 A1 | 10/2014 | Rosenbluth |
| 2014/0330286 A1 | 11/2014 | Wallace et al. |
| 2014/0336691 A1 | 11/2014 | Jones et al. |
| 2014/0343593 A1 | 11/2014 | Chin et al. |
| 2014/0364896 A1 | 12/2014 | Consigny |
| 2014/0371779 A1 | 12/2014 | Vale et al. |
| 2015/0005781 A1 | 1/2015 | Lund-Clausen et al. |
| 2015/0005792 A1 | 1/2015 | Ahn |
| 2015/0018859 A1 | 1/2015 | Quick |
| 2015/0018860 A1 | 1/2015 | Quick |
| 2015/0018929 A1 | 1/2015 | Martin et al. |
| 2015/0025555 A1 | 1/2015 | Sos |
| 2015/0032144 A1 | 1/2015 | Holloway |
| 2015/0059908 A1 | 3/2015 | Mollen |
| 2015/0088190 A1 | 3/2015 | Jensen |
| 2015/0127035 A1 | 5/2015 | Trapp et al. |
| 2015/0133990 A1 | 5/2015 | Davidson |
| 2015/0150672 A1 | 6/2015 | Ma |
| 2015/0164523 A1 | 6/2015 | Brady et al. |
| 2015/0164666 A1 | 6/2015 | Johnson et al. |
| 2015/0173782 A1 | 6/2015 | Garrison et al. |
| 2015/0190155 A1 | 7/2015 | Ulm, III |
| 2015/0190156 A1 | 7/2015 | Ulm, III |
| 2015/0196380 A1 | 7/2015 | Berrada et al. |
| 2015/0196744 A1 | 7/2015 | Aboytes |
| 2015/0209058 A1 | 7/2015 | Ferrera et al. |
| 2015/0209165 A1 | 7/2015 | Grandfield et al. |
| 2015/0238207 A1 | 8/2015 | Cox et al. |
| 2015/0250578 A1 | 9/2015 | Cook et al. |
| 2015/0265299 A1 | 9/2015 | Cooper et al. |
| 2015/0283309 A1 | 10/2015 | Look et al. |
| 2015/0305756 A1 | 10/2015 | Rosenbluth |
| 2015/0305859 A1 | 10/2015 | Eller |
| 2015/0314050 A1 | 11/2015 | Beer |
| 2015/0327875 A1 | 11/2015 | Look et al. |
| 2015/0352325 A1 | 12/2015 | Quick |
| 2015/0360001 A1 | 12/2015 | Quick |
| 2015/0366690 A1 | 12/2015 | Lumauig |
| 2015/0374391 A1 | 12/2015 | Quick |
| 2016/0022293 A1 | 1/2016 | Dubrul et al. |
| 2016/0030708 A1 | 2/2016 | Casiello et al. |
| 2016/0038267 A1 | 2/2016 | Allen et al. |
| 2016/0058540 A1 | 3/2016 | Don Michael |
| 2016/0074627 A1 | 3/2016 | Cottone |
| 2016/0106353 A1 | 4/2016 | Schuetz et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0113666 A1 | 4/2016 | Quick |
| 2016/0128857 A1 | 5/2016 | Kao |
| 2016/0135829 A1 | 5/2016 | Holochwost et al. |
| 2016/0143721 A1 | 5/2016 | Rosenbluth |
| 2016/0151605 A1 | 6/2016 | Welch et al. |
| 2016/0192912 A1 | 7/2016 | Kassab et al. |
| 2016/0206344 A1 | 7/2016 | Bruzzi et al. |
| 2016/0008014 A1 | 8/2016 | Rosenbluth |
| 2016/0220741 A1 | 8/2016 | Garrison et al. |
| 2016/0220795 A1 | 8/2016 | Korkuch et al. |
| 2016/0228134 A1 | 8/2016 | Martin et al. |
| 2016/0262774 A1 | 9/2016 | Honda |
| 2016/0262790 A1 | 9/2016 | Rosenbluth et al. |
| 2016/0287276 A1 | 10/2016 | Cox et al. |
| 2016/0367285 A1 | 12/2016 | Sos |
| 2017/0014560 A1 | 1/2017 | Minskoff et al. |
| 2017/0021130 A1 | 1/2017 | Dye |
| 2017/0037548 A1 | 2/2017 | Lee |
| 2017/0042571 A1 | 2/2017 | Levi |
| 2017/0049942 A1 | 2/2017 | Conlan et al. |
| 2017/0056032 A1 | 3/2017 | Look et al. |
| 2017/0058623 A1 | 3/2017 | Jaffrey et al. |
| 2017/0079672 A1 | 3/2017 | Quick |
| 2017/0086864 A1 | 3/2017 | Greenhalgh et al. |
| 2017/0100142 A1 | 4/2017 | Look et al. |
| 2017/0105743 A1 | 4/2017 | Vale et al. |
| 2017/0105745 A1 | 4/2017 | Rosenbluth et al. |
| 2017/0112514 A1 | 4/2017 | Marchand et al. |
| 2017/0113005 A1 | 4/2017 | Linder et al. |
| 2017/0143359 A1 | 5/2017 | Nguyen et al. |
| 2017/0143880 A1 | 5/2017 | Luxon et al. |
| 2017/0143938 A1 | 5/2017 | Ogle et al. |
| 2017/0172591 A1 | 6/2017 | Ulm, III |
| 2017/0112513 A1 | 7/2017 | Marchand et al. |
| 2017/0189041 A1 | 7/2017 | Cox et al. |

(56) References Cited

U.S. PATENT DOCUMENTS

| | | |
|---|---|---|
| 2017/0196576 A1 | 7/2017 | Long et al. |
| 2017/0233908 A1 | 8/2017 | Kroczynski et al. |
| 2017/0238951 A1 | 8/2017 | Yang et al. |
| 2017/0252057 A1 | 9/2017 | Bonnette et al. |
| 2017/0265878 A1 | 9/2017 | Marchand et al. |
| 2017/0281204 A1 | 10/2017 | Garrison et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0319221 A1 | 11/2017 | Chu |
| 2017/0325839 A1 | 11/2017 | Rosenbluth et al. |
| 2017/0340867 A1 | 11/2017 | Accisano, II |
| 2017/0348014 A1 | 12/2017 | Wallace et al. |
| 2018/0014840 A1 | 1/2018 | Panian |
| 2018/0042623 A1 | 2/2018 | Batiste |
| 2018/0042624 A1 | 2/2018 | Greenhalgh et al. |
| 2018/0042626 A1 | 2/2018 | Greenhalgh et al. |
| 2018/0055999 A1 | 3/2018 | Bare et al. |
| 2018/0064453 A1 | 3/2018 | Garrison et al. |
| 2018/0064454 A1 | 3/2018 | Losordo et al. |
| 2018/0070968 A1 | 3/2018 | Wallace et al. |
| 2018/0078707 A1 | 3/2018 | Loonan |
| 2018/0092652 A1 | 4/2018 | Marchand et al. |
| 2018/0104404 A1 | 4/2018 | Ngo-Chu |
| 2018/0105963 A1 | 4/2018 | Quick |
| 2018/0125512 A1 | 5/2018 | Nguyen et al. |
| 2018/0184912 A1 | 7/2018 | Al-Ali |
| 2018/0193043 A1 | 7/2018 | Marchand et al. |
| 2018/0235742 A1 | 8/2018 | Fields et al. |
| 2018/0236205 A1 | 8/2018 | Krautkremer et al. |
| 2018/0250498 A1 | 9/2018 | Stern et al. |
| 2018/0256177 A1 | 9/2018 | Cooper et al. |
| 2018/0256178 A1 | 9/2018 | Cox et al. |
| 2018/0280623 A1 | 10/2018 | Pilkington |
| 2018/0296240 A1 | 10/2018 | Rosenbluth et al. |
| 2018/0338770 A1 | 11/2018 | Mogi et al. |
| 2018/0339130 A1 | 11/2018 | Ogle |
| 2018/0344339 A1 | 12/2018 | Cox et al. |
| 2018/0361116 A1 | 12/2018 | Quick et al. |
| 2019/0000492 A1 | 1/2019 | Casey et al. |
| 2019/0015298 A1 | 1/2019 | Beatty et al. |
| 2019/0046219 A1 | 2/2019 | Marchand et al. |
| 2019/0070401 A1 | 3/2019 | Merritt et al. |
| 2019/0117244 A1 | 4/2019 | Wallace et al. |
| 2019/0133622 A1 | 5/2019 | Wallace et al. |
| 2019/0133623 A1 | 5/2019 | Wallace et al. |
| 2019/0133624 A1 | 5/2019 | Wallace et al. |
| 2019/0133625 A1 | 5/2019 | Wallace et al. |
| 2019/0133626 A1 | 5/2019 | Wallace et al. |
| 2019/0133627 A1 | 5/2019 | Wallace et al. |
| 2019/0150959 A1 | 5/2019 | Cox et al. |
| 2019/0216476 A1 | 7/2019 | Barry et al. |
| 2019/0223893 A1 | 7/2019 | Gilvarry et al. |
| 2019/0231373 A1 | 8/2019 | Quick |
| 2019/0239910 A1 | 8/2019 | Brady et al. |
| 2019/0321071 A1 | 10/2019 | Marchand et al. |
| 2019/0328411 A1 | 10/2019 | Vale et al. |
| 2019/0336142 A1 | 11/2019 | Torrie et al. |
| 2019/0336148 A1 | 11/2019 | Greenhalgh et al. |
| 2019/0365395 A1 | 12/2019 | Tran et al. |
| 2019/0366036 A1 | 12/2019 | Jalgaonkar et al. |
| 2019/0366049 A1 | 12/2019 | Hannon et al. |
| 2020/0022711 A1 | 1/2020 | Look et al. |
| 2020/0030579 A1 | 1/2020 | Taber |
| 2020/0046368 A1 | 2/2020 | Merritt et al. |
| 2020/0046940 A1 | 2/2020 | Carrison et al. |
| 2020/0054861 A1 | 2/2020 | Korkuch et al. |
| 2020/0069889 A1 | 3/2020 | Lin |
| 2020/0078029 A1 | 3/2020 | Hansen et al. |
| 2020/0113412 A1 | 4/2020 | Jensen |
| 2020/0121334 A1 | 4/2020 | Galdonik et al. |
| 2020/0129741 A1 | 4/2020 | Kawwas et al. |
| 2020/0324079 A1 | 10/2020 | Jalgaonkar et al. |
| 2021/0022843 A1 | 1/2021 | Hauser |
| 2021/0038385 A1 | 2/2021 | Popp et al. |
| 2021/0113224 A1 | 4/2021 | Dinh |
| 2021/0128182 A1 | 5/2021 | Teigen et al. |
| 2021/0137667 A1 | 5/2021 | Sonnette et al. |
| 2021/0138194 A1 | 5/2021 | Carrison et al. |
| 2021/0154433 A1 | 5/2021 | Casey et al. |
| 2021/0186537 A1 | 6/2021 | Buck et al. |
| 2021/0186541 A1 | 6/2021 | Thress |
| 2021/0205577 A1 | 7/2021 | Jalgaonkar et al. |
| 2021/0236148 A1 | 8/2021 | Marchand et al. |
| 2021/0290925 A1 | 9/2021 | Merritt et al. |
| 2021/0315598 A1 | 10/2021 | Buck et al. |
| 2021/0316127 A1 | 10/2021 | Buck et al. |
| 2021/0330344 A1 | 10/2021 | Rosenbluth et al. |
| 2021/0378694 A1 | 12/2021 | Thress et al. |
| 2021/0393278 A1 | 12/2021 | O'Malley et al. |
| 2021/0404464 A1 | 12/2021 | Patoskie |
| 2022/0000505 A1 | 1/2022 | Hauser |
| 2022/0000506 A1 | 1/2022 | Hauser |
| 2022/0000507 A1 | 1/2022 | Hauser |
| 2022/0015798 A1 | 1/2022 | Marchand et al. |
| 2022/0021197 A1 | 1/2022 | Zhao et al. |
| 2022/0022898 A1 | 1/2022 | Cox et al. |
| 2022/0033888 A1 | 2/2022 | Schnall-Levin et al. |
| 2022/0039815 A1 | 2/2022 | Thress et al. |
| 2022/0125451 A1 | 4/2022 | Hauser |
| 2022/0142638 A1 | 5/2022 | Enright et al. |
| 2022/0151647 A1 | 5/2022 | Dolendo et al. |
| 2022/0152355 A1 | 5/2022 | Dolendo et al. |
| 2022/0160381 A1 | 5/2022 | Hauser |
| 2022/0160382 A1 | 5/2022 | Hauser |
| 2022/0160383 A1 | 5/2022 | Hauser |
| 2022/0211400 A1 | 7/2022 | Cox et al. |
| 2022/0211992 A1 | 7/2022 | Merritt et al. |
| 2022/0226555 A1 | 7/2022 | Sunenshine et al. |
| 2022/0240959 A1 | 8/2022 | Quick |
| 2022/0296797 A1 | 9/2022 | Chawla |
| 2022/0331554 A1 | 10/2022 | Beasley et al. |
| 2022/0346800 A1 | 11/2022 | Merritt et al. |
| 2022/0346813 A1 | 11/2022 | Quick |
| 2022/0346814 A1 | 11/2022 | Quick |
| 2022/0347455 A1 | 11/2022 | Merritt et al. |
| 2022/0362512 A1 | 11/2022 | Quick et al. |
| 2022/0370761 A1 | 11/2022 | Chou et al. |
| 2022/0378445 A1 | 12/2022 | Culbert et al. |
| 2022/0378446 A1 | 12/2022 | Culbert et al. |
| 2022/0378447 A1 | 12/2022 | Culbert et al. |
| 2022/0378448 A1 | 12/2022 | Culbert et al. |
| 2022/0378451 A1 | 12/2022 | Goyal et al. |
| 2022/0378460 A1 | 12/2022 | Culbert et al. |
| 2022/0387072 A1 | 12/2022 | Look et al. |
| 2023/0015259 A1 | 1/2023 | Buck et al. |
| 2023/0046775 A1 | 2/2023 | Quick |
| 2023/0047682 A1 | 2/2023 | Deaton et al. |
| 2023/0052964 A1 | 2/2023 | Singh et al. |
| 2023/0059721 A1 | 2/2023 | Chou et al. |
| 2023/0062809 A1 | 3/2023 | Merritt et al. |
| 2023/0070120 A1 | 3/2023 | Cox et al. |
| 2023/0122587 A1 | 4/2023 | Chou et al. |
| 2023/0149034 A1 | 5/2023 | Aklog et al. |
| 2023/0200970 A1 | 6/2023 | Merritt et al. |
| 2023/0210554 A1 | 7/2023 | Bruzzi et al. |
| 2023/0218310 A1 | 7/2023 | Scheinblum et al. |
| 2023/0218313 A1 | 7/2023 | Rosenbluth et al. |
| 2023/0218383 A1 | 7/2023 | Merritt et al. |
| 2023/0233311 A1 | 7/2023 | Merritt et al. |
| 2023/0240705 A1 | 8/2023 | Rosenbluth et al. |
| 2023/0240706 A1 | 8/2023 | Rosenbluth et al. |
| 2023/0241302 A1 | 8/2023 | Merritt et al. |
| 2023/0248380 A1 | 8/2023 | Long et al. |
| 2023/0248498 A1 | 8/2023 | Buck et al. |
| 2023/0248499 A1 | 8/2023 | Buck et al. |
| 2023/0248500 A1 | 8/2023 | Buck et al. |
| 2023/0248501 A1 | 8/2023 | Buck et al. |
| 2023/0248502 A1 | 8/2023 | Buck et al. |
| 2023/0248503 A1 | 8/2023 | Buck et al. |
| 2023/0248504 A1 | 8/2023 | Buck et al. |
| 2023/0270991 A1 | 8/2023 | Merritt et al. |
| 2023/0310137 A1 | 10/2023 | Merritt et al. |

(56) References Cited

U.S. PATENT DOCUMENTS

| | | |
|---|---|---|
| 2023/0310138 A1 | 10/2023 | Merritt et al. |
| 2023/0310751 A1 | 10/2023 | Merritt et al. |
| 2023/0320834 A1 | 10/2023 | Merritt et al. |
| 2023/0338130 A1 | 10/2023 | Merritt et al. |
| 2023/0338131 A1 | 10/2023 | Merritt et al. |
| 2023/0355256 A1 | 11/2023 | Dinh |
| 2023/0355259 A1 | 11/2023 | Marchand et al. |
| 2023/0355371 A1 | 11/2023 | Buck et al. |
| 2023/0355938 A1 | 11/2023 | Merritt et al. |
| 2023/0363776 A1 | 11/2023 | Quick |
| 2023/0363883 A1 | 11/2023 | Merritt et al. |
| 2023/0389932 A1 | 12/2023 | Ozenne et al. |
| 2023/0390045 A1 | 12/2023 | Merritt et al. |
| 2024/0016505 A1 | 1/2024 | Horowitz et al. |
| 2024/0016993 A1 | 1/2024 | Haslam et al. |
| 2024/0058113 A1 | 2/2024 | Strauss et al. |
| 2024/0074771 A1 | 3/2024 | Quick et al. |
| 2024/0082540 A1 | 3/2024 | Brodt et al. |
| 2024/0108366 A1 | 4/2024 | Horowitz et al. |
| 2024/0131235 A1 | 4/2024 | Horowitz et al. |
| 2024/0157041 A1 | 5/2024 | Zikry et al. |
| 2024/0173042 A1 | 5/2024 | Yang et al. |
| 2024/0198072 A1 | 6/2024 | Merritt et al. |
| 2024/0207593 A1 | 6/2024 | Merritt et al. |
| 2024/0225674 A1 | 7/2024 | Dederich et al. |
| 2024/0245501 A1 | 7/2024 | Strauss et al. |
| 2024/0245502 A1 | 7/2024 | Merritt et al. |
| 2024/0261492 A1 | 8/2024 | Yang et al. |
| 2024/0285387 A1 | 8/2024 | Merritt et al. |
| 2024/0299053 A1 | 9/2024 | Hauser |
| 2024/0307082 A1 | 9/2024 | Marchand et al. |
| 2024/0307166 A1 | 9/2024 | Merritt et al. |
| 2024/0341779 A1 | 10/2024 | Dinh |
| 2024/0341788 A1 | 10/2024 | Cox et al. |

FOREIGN PATENT DOCUMENTS

| | | |
|---|---|---|
| CN | 102316809 | 1/2012 |
| CN | 103764049 | 4/2014 |
| CN | 103932756 | 7/2014 |
| CN | 104068910 | 10/2014 |
| CN | 106178227 | 12/2016 |
| CN | 106470728 | 3/2017 |
| CN | 108348319 | 7/2018 |
| CN | 110312481 | 10/2019 |
| CN | 110652645 | 1/2020 |
| CN | 111281482 | 6/2020 |
| DE | 1116001 | 10/1961 |
| DE | 102017004383 | 7/2018 |
| EP | 0914807 | 5/1999 |
| EP | 1254634 | 11/2002 |
| EP | 1991138 | 11/2008 |
| EP | 2073864 | 7/2009 |
| EP | 2203209 | 7/2010 |
| EP | 2209509 | 7/2010 |
| EP | 2394680 | 12/2011 |
| EP | 1867290 | 2/2013 |
| EP | 2624905 | 8/2013 |
| EP | 2540328 | 10/2013 |
| EP | 2726135 | 5/2014 |
| EP | 2908783 | 8/2015 |
| EP | 2939704 | 11/2015 |
| EP | 2942624 | 11/2015 |
| EP | 2967614 | 1/2016 |
| EP | 2977072 | 1/2016 |
| EP | 2367482 | 10/2016 |
| EP | 3102274 | 12/2016 |
| EP | 3122412 | 2/2017 |
| EP | 3202340 | 8/2017 |
| EP | 3302624 | 4/2018 |
| EP | 3305220 | 4/2018 |
| EP | 3305221 | 4/2018 |
| EP | 3311875 | 4/2018 |
| EP | 2231256 | 5/2018 |
| EP | 3344157 | 7/2018 |
| EP | 3417893 | 12/2018 |
| EP | 3419528 | 1/2019 |
| EP | 3422963 | 1/2019 |
| EP | 3439561 | 2/2019 |
| EP | 3449967 | 3/2019 |
| EP | 3544528 | 10/2019 |
| EP | 3583972 | 12/2019 |
| EP | 3589348 | 1/2020 |
| EP | 3603690 | 2/2020 |
| EP | 3612264 | 2/2020 |
| EP | 3620204 | 3/2020 |
| EP | 3013404 | 4/2020 |
| EP | 4039205 | 8/2022 |
| EP | 4072613 | 10/2022 |
| EP | 4076611 | 10/2022 |
| EP | 4079344 | 10/2022 |
| EP | 4137070 | 2/2023 |
| EP | 4144310 | 3/2023 |
| EP | 4252992 | 10/2023 |
| EP | 4419159 | 8/2024 |
| GB | 1588072 | 4/1981 |
| GB | 2498349 | 7/2013 |
| JP | H6190049 | 7/1994 |
| JP | H07323090 A | 12/1995 |
| JP | 2001522631 | 5/1999 |
| JP | 2000175925 | 6/2000 |
| JP | 2004097807 | 4/2004 |
| JP | 2005511989 | 4/2005 |
| JP | 2005-095242 | 6/2005 |
| JP | 2005230132 | 9/2005 |
| JP | 2005323702 | 11/2005 |
| JP | 2006094876 | 4/2006 |
| JP | 2007-222658 | 9/2007 |
| JP | 2011526820 | 1/2010 |
| JP | 2011517424 | 6/2011 |
| JP | 05694718 | 4/2015 |
| JP | 2015208685 | 11/2015 |
| JP | 2016513505 | 5/2016 |
| JP | 2016104212 | 6/2016 |
| JP | 2017533051 | 11/2017 |
| JP | 2018525088 | 9/2018 |
| JP | 2003033359 | 2/2023 |
| JP | 7253376 | 3/2023 |
| JP | 7324264 | 8/2023 |
| JP | 7491974 | 5/2024 |
| WO | WO1997017889 | 5/1997 |
| WO | WO9833443 | 8/1998 |
| WO | WO9838920 | 9/1998 |
| WO | WO9839053 | 9/1998 |
| WO | WO9851237 | 11/1998 |
| WO | WO1999044542 | 9/1999 |
| WO | WO0032118 | 6/2000 |
| WO | WO2000053120 | 9/2000 |
| WO | WO0202162 | 1/2002 |
| WO | WO20002055146 | 7/2002 |
| WO | WO03015840 | 2/2003 |
| WO | WO2004018916 | 3/2004 |
| WO | WO2004093696 | 11/2004 |
| WO | WO2005046736 | 5/2005 |
| WO | WO2006029270 | 3/2006 |
| WO | WO2006110186 | 10/2006 |
| WO | WO2006124307 | 11/2006 |
| WO | WO2007092820 | 8/2007 |
| WO | WO2009082513 | 7/2009 |
| WO | WO2009086482 | 7/2009 |
| WO | WO2009126747 | 10/2009 |
| WO | WO2009155571 | 12/2009 |
| WO | WO2010002549 | 1/2010 |
| WO | WO2010010545 | 1/2010 |
| WO | WO2010023671 | 3/2010 |
| WO | WO2010049121 | 5/2010 |
| WO | WO2010095712 | 8/2010 |
| WO | WO2010102307 | 9/2010 |
| WO | WO2011054531 | 5/2011 |
| WO | WO2011073176 | 6/2011 |
| WO | WO2012009675 | 1/2012 |
| WO | WO2012011097 | 1/2012 |
| WO | WO2012049652 | 4/2012 |
| WO | WO2012065748 | 5/2012 |

(56) References Cited

FOREIGN PATENT DOCUMENTS

| WO | WO2012114633 | 8/2012 |
|---|---|---|
| WO | WO2012120490 | 9/2012 |
| WO | WO2012162437 | 11/2012 |
| WO | WO2014047650 | 3/2014 |
| WO | WO2014081892 | 5/2014 |
| WO | WO2015006782 | 1/2015 |
| WO | WO2015061365 | 4/2015 |
| WO | WO2015121424 | 8/2015 |
| WO | WO2015179329 | 11/2015 |
| WO | WO2015189354 | 12/2015 |
| WO | WO2015191646 | 12/2015 |
| WO | WO2016014955 | 1/2016 |
| WO | WO2016071524 | 5/2016 |
| WO | WO2017024258 | 2/2017 |
| WO | WO2017033182 | 3/2017 |
| WO | WO2017058280 | 4/2017 |
| WO | WO2017070702 | 4/2017 |
| WO | WO2017106877 | 6/2017 |
| WO | WO2017189535 | 11/2017 |
| WO | WO2017189550 | 11/2017 |
| WO | WO2017189591 | 11/2017 |
| WO | WO2017189615 | 11/2017 |
| WO | WO2017210487 | 12/2017 |
| WO | WO2018049317 | 3/2018 |
| WO | WO2018065092 | 4/2018 |
| WO | WO2018080590 | 5/2018 |
| WO | WO2018148174 | 8/2018 |
| WO | WO2019010318 | 1/2019 |
| WO | WO2019050765 | 3/2019 |
| WO | WO2019064306 | 4/2019 |
| WO | WO2019075444 | 4/2019 |
| WO | WO2019094456 | 5/2019 |
| WO | WO2019173475 | 9/2019 |
| WO | WO2019222117 | 11/2019 |
| WO | WO2019246240 | 12/2019 |
| WO | WO2020036809 | 2/2020 |
| WO | WO2020142381 | 7/2020 |
| WO | WO2021067134 | 4/2021 |
| WO | WO2021076954 | 4/2021 |
| WO | WO2021127202 | 6/2021 |
| WO | WO2021248042 | 12/2021 |
| WO | WO2022032173 | 2/2022 |
| WO | WO2022103848 | 5/2022 |
| WO | WO2022109021 | 5/2022 |
| WO | WO2022109034 | 5/2022 |
| WO | WO2023018819 | 2/2023 |
| WO | WO2023069874 | 4/2023 |
| WO | WO2003048616 | 6/2023 |
| WO | WO2023115032 | 6/2023 |
| WO | WO2023137341 | 7/2023 |
| WO | WO2023147353 | 8/2023 |
| WO | WO2023154612 | 8/2023 |
| WO | WO2023192925 | 10/2023 |
| WO | WO2023215779 | 11/2023 |
| WO | WO2024103036 | 5/2024 |
| WO | WO2024151629 | 7/2024 |

OTHER PUBLICATIONS

US 12,115,056 B2, 10/2024, Merritt et al. (withdrawn)
International Search Report and Written Opinion for International App. No. PCT/US23/60927; Date of Filing: Jan. 19, 2023, Applicant: Inari Medical, Inc., Date of Mailing: Jul. 20, 2023, 12 pages.
Extended European Search Report issued for EP Application No. 20877370.5, Date of Mailing: Oct. 17, 2023, 11 pages.
International Search Report and Written Opinion for International App. No. PCT/US23/65128; Date of Filing: Mar. 30, 2023, Applicant: Inari Medical, Inc., Date of Mailing: Nov. 14, 2023, 14 pages.
International Search Report and Written Opinion for International App. No. PCT/US23/66538; Date of Filing: May 3, 2023, Applicant: Inari Medical, Inc., Date of Mailing: Jan. 4, 2024, 14 pages.
English translation of Japanese Office Action received for JP Application No. 2022-574456, Applicant: Inari Medical, Inc, Date of Mailing: Jan. 23, 2024, 12 pages.
Chinese First Office Action received for CN Application No. 201980067623.1, Applicant: Inari Medical, Inc., Date of Mailing: Jan. 31, 2024, 10 pages.
Gibbs, et al., "Temporary Stent as a bail-out device during percutaneous transluminal coronary angioplasty: preliminary clinical experience," British Heart Journal, 1994, 71:372-377, Oct. 12, 1993, 6 pgs.
Gupta, S. et al., "Acute Pulmonary Embolism Advances in Treatment", JAPI, Association of Physicians India, Mar. 2008, vol. 56, 185-191.
International Search Report and Written Opinion for International App. No. PCT/US13/61470, mailed Jan. 17, 2014, 7 pages.
International Search Report and Written Opinion for International App. No. PCT/US2014/046567, mailed Nov. 3, 2014, 13 pages.
International Search Report and Written Opinion for International App. No. PCT/US2014/061645, mailed Jan. 23, 2015, 15 pages.
International Search Report for International App. No. PCT/US13/71101, mailed Mar. 31, 2014, 4 pages.
Konstantinides, S. et al., "Pulmonary embolism hotline 2012—Recent and expected trials", Thrombosis and Haemostasis, Jan. 9, 2013:33; 43-50.
Konstantinides, S. et al., "Pulmonary embolism: risk assessment and management", European Society of Cardiology; European Heart Journal, Sep. 7, 2012:33, 3014-3022.
Kucher, N. et al., "Percutaneous Catheter Thrombectomy Device for Acute Pulmonary Embolism: In Vitro and in Vivo Testing", Circulation, Sep. 2005:112:e28-e32.
Kucher, N., "Catheter Interventions in Massive Pulmonary Embolism", Cardiology Rounds, Mar. 2006 vol. 10, Issue 3, 6 pages.
Kucher, N. et al., "Management of Massive Pulmonary Embolism", Radiology, Sep. 2005:236:3 852-858.
Kucher, N. et al., "Randomized, Controlled Trial of Ultrasound-Assisted Catheter-Directed Thrombolysis for Acute Intermediate-Risk Pulmonary Embolism." Circulation, 2014, 129, pp. 9 pages.
Kuo, W. et al., "Catheter-directed Therapy for the Treatment of Massive Pulmonary Embolism: Systematic Review and Meta-analysis of Modern Techniques", Journal of Vascular and Interventional Radiology, Nov. 2009:20:1431-1440.
Kuo, W. et al., "Catheter-Directed Embolectomy, Fragmentation, and Thrombolysis for the Treatment of Massive Pulmonary Embolism After Failure of Systemic Thrombolysis", American College of CHEST Physicians 2008: 134:250-254.
Kuo, W. MD, "Endovascular Therapy for Acute Pulmonary Embolism", Continuing Medical Education Society of Interventional Radiology ("CME"); Journal of Vascular and Interventional Radiology, Feb. 2012: 23:167-179.
Lee, L. et al, "Massive pulmonary embolism: review of management strategies with a focus on catheter-based techniques", Expert Rev. Cardiovasc. Ther. 8(6), 863-873 (2010).
Liu, S. et al, "Massive Pulmonary Embolism: Treatment with the Rotarex Thrombectomy System", Cardiovascular Interventional Radiology; 2011: 34:106-113.
Muller-Hulsbeck, S. et al. "Mechanical Thrombectomy of Major and Massive Pulmonary Embolism with Use of the Amplatz Thrombectomy Device", Investigative Radiology, Jun. 2001:36:6:317-322.
Reekers, J. et al., "Mechanical Thrombectomy for Early Treatment of Massive Pulmonary Embolism", CardioVascular and Interventional Radiology, 2003: 26:246-250.
Schmitz-Rode et al., "New Mesh Basket for Percutaneous Removal of Wall-Adherent Thrombi in Dialysis Shunts," Cardiovasc Intervent Radiol 16:7-10 1993 4 pgs.
Schmitz-Rode et al., "Temporary Pulmonary Stent Placement as Emergency Treatment of Pulmonary Embolism," Journal of the American College of Cardiology, vol. 48, No. 4, 2006 (5 pgs.).
Schmitz-Rode, T. et al., "Massive Pulmonary Embolism: Percutaneous Emergency Treatment by Pigtail Rotation Catheter", JACC Journal of the American College of Cardiology, Aug. 2000:36:2:375-380.
Spiotta, A et al., "Evolution of thrombectomy approaches and devices for acute stroke: a technical review." J NeuroIntervent Surg 2015, 7, pp. 7 pages.

(56) References Cited

OTHER PUBLICATIONS

Svilaas, T. et al., "Thrombus Aspiration During Primary Percutaneous Coronary Intervention." The New England Journal of Medicine, 2008, vol. 358, No. 6, 11 pages.

Tapson, V., "Acute Pulmonary Embolism", The New England Journal of Medicine, Mar. 6, 2008:358:2037-52.

The Penumbra Pivotal Stroke Trial Investigators, "The Penumbra Pivotal Stroke Trial: Safety and Effectiveness of a New Generation of Mechanical Devices for Clot Removal in Intracranial Large Vessel Occlusive Disease." Stroke, 2009, 40: p. 9 pages.

Truong et al., "Mechanical Thrombectomy of Iliocaval Thrombosis Using a Protective Expandable Sheath," Cardiovasc Intervent Radiol27-254-258, 2004, 5 pgs.

Turk et al., "ADAPT FAST study: a direct aspiration first pass technique for acute stroke thrombectomy." J NeuroIntervent Surg, vol. 6, 2014, 6 pages.

Uflacker, R., "Interventional Therapy for Pulmonary Embolism", Journal of Vascular and Interventional Radiology, Feb. 2001: 12:147-164.

Verma, R., MD et al. "Evaluation of a Newly Developed Percutaneous Thrombectomy Basket Device in Sheep With Central Pulmonary Embolisms", *Investigative Radiology*, Oct. 2006, 41, 729-734.

International Search Report and Written Opinion for International App. No. PCT/US2015/034987 filed Jun. 9, 2015, Applicant: Inceptus Medical, LLC, Date of Mailing: Sep. 17, 2015, 12 pages.

International Search Report and Written Opinion for International App. No. PCT/US2016/067628 filed Dec. 19, 2016, Applicant: Inari Medical, Inc., Date of Mailing: Apr. 10, 2017, 11 pages.

Goldhaber, S. et al. "Percutaneous Mechanical Thrombectomy for Acute Pulmonary Embolism—A Double-Edged Sword," American College of CHEST Physicians, Aug. 2007, 132:2, 363-372.

Goldhaber, S., "Advanced treatment strategies for acute pulmonary embolism, including thrombolysis and embolectomy," Journal of Thrombosis and Haemostasis, 2009: 7 (Suppl. 1): 322-327.

International Search Report and Written Opinion for International App. No. PCT/US2017/029696, Date of Filing: Apr. 26, 2017, Applicant: Inari Medical, Inc., Date of Mailing: Sep. 15, 2017, 19 pages.

International Search Report and Written Opinion for International App. No. PCT/US2016/058536, Date of Filing: Oct. 24, 2016, Applicant: Inari Medical, Inc., Date of Mailing: Mar. 13, 2017, 14 pages.

International Search Report and Written Opinion for International App. No. PCT/US2018/048786, Date of Filing: Aug. 30, 2018, Applicant: Inari Medical, Inc., Date of Mailing: Dec. 13, 2018, 12 pages.

International Search Report and Written Opinion for International App. No. PCT/US2018/055780, Date of Filing: Oct. 13, 2018, Applicant: Inceptus Medical LLC., Date of Mailing: Jan. 22, 2019, 8 pages.

International Search Report and Written Opinion for International App. No. PCT/US2019/045794, Date of Filing: Aug. 8, 2019, Applicant: Inari Medical, Inc., Date of Mailing: Nov. 1, 2019, 17 pages.

International Search Report and Written Opinion for International App. No. PCT/US2020/056067, Date of Filing: Oct. 16, 2020; Applicant: Inari Medical, Inc., Date of Mailing: Jan. 22, 2021, 8 pages.

International Search Report and Written Opinion for International App. No. PCT/US2020/055645, Date of Filing: Dec. 17, 2020; Applicant: Inari Medical, Inc., Date of Mailing: Apr. 14, 2021, 12 pages.

Vorwerk, D. MD, et al., "Use of a Temporary Caval Filter to Assist Percutaneous Iliocaval Thrombectomy: Experimental Results." SCVIR, 1995, 4 pages.

Wikipedia; Embolectomy; retrieved from the internet: https://en.wikipedia.org/wiki/Embolectomy; 4 pgs.; retrieved/printed: Mar. 24, 2016.

O'Sullivan; Thrombolysis versus thrombectomy in acute deep vein thrombosis; Interventional Cardiology; 3(5); pp. 589-596; Oct. 2011.

Capture Vascular Systems; (company website); retrieved from the internet: http://www.capturevascular.com; 3 pgs.; retrieved/printed: Mar. 24, 2016.

Edwards LifeSciences; Fogarty® Occlusion Catheters (product brochure); retrieved from the internet: http://web.archive.org/web/20150228193218/http://www.edwards.com/products/vascular/atraumaticocclusion/pages/occlusioncatheter.aspx; © 2011; 2 pgs.; retrieved/printed: Mar. 24, 2011.

Boston Scientific; Fetch(TM) 2 Aspiration Catheter (product information);retrieved from the internet: http://www.bostonscientific.com/en-US/products/thrombectomy-systems/fetch2-aspiration-catheter.html; 2 pgs.; retrieved/printed: Mar. 24, 2016.

Penumbra, Inc.; Indigo® System (product information); retrieved from the internet: http://www.penumbrainc.com/peripherallpercutaneous-thromboembolectomy/indigo-system; 7 pgs.; retrieved/printed: Mar. 24, 2016.

YouTube; Merci Retrieval System X Series Animation; uploaded Mar. 16, 2009 (product information); posted on May 7, 2009 by SSMDePaul, time 1:09, retrieved from the internet: https://www.youtube.com/watch?v=MGX7deuFkhc; 3 pgs.; retrieved/printed: Mar. 24, 2016.

Covidien; Solitaire(TM) AS Neurovascular Remodeling Device (product information); retrieved from the internet: http://www.ev3.net/neuro/intl/remodeling-devices/solitaire-ab. htm; © 2015; 2 pgs.; retrieved/printed: Mar. 24, 2016.

International Search Report and Written Opinion for International App. No. PCT/US21/35965, Date of Filing: Jun. 4, 2021, Applicant: Inari Medical, Inc., Date of Mailing: Sep. 28, 2021, 12 pages.

International Search Report and Written Opinion for International App. No. PCT/US21/45072 Date of Filing: Aug. 6, 2021, Applicant: Inari Medical, Inc., Date of Mailing: Jan. 20, 2022, 10 pages.

International Search Report and Written Opinion for International App. No. PCT/US21/58793; Date of Filing: Nov. 10, 2021, Applicant: Inari Medical, Inc., Date of Mailing: Mar. 16, 2022, 13 pages.

International Search Report and Written Opinion for International App. No. PCT/US21/59718; Date of Filing: Nov. 17, 2021, Applicant: Inari Medical, Inc., Date of Mailing: Mar. 22, 2022, 13 pages.

International Search Report and Written Opinion for International App. No. PCT/US21/59735; Date of Filing: Nov. 17, 2021, Applicant: Inari Medical, Inc., Date of Mailing: Mar. 22, 2022, 11 pages.

International Search Report and Written Opinion for International App. No. PCT/US23/60502; Date of Filing: Jan. 11, 2023, Applicant: Inari Medical, Inc., Date of Mailing: May 25, 2023, 9 pages.

International Search Report and Written Opinion for International App. No. PCT/US23/61256; Date of Filing: Jan. 25, 2023, Applicant: Inari Medical, Inc., Date of Mailing: Jun. 7, 2023, 8 pages.

Gross et al., "Dump the pump: manual aspiration thrombectomy (MAT) with a syringe is technically effective, expeditious, and cost-efficient," J NeuroIntervent Surg, 2018, 4 pages.

International Search Report and Written Opinion for International App. No. PCT/US23/73765; Date of Filing: Sep. 8, 2023, Applicant: Inari Medical, Inc., Date of Mailing: Feb. 28, 2024, 7 pages.

International Search Report and Written Opinion for International App. No. PCT/US23/69892; Date of Filing: Jul. 10, 2023, Applicant: Inari Medical, Inc., Date of Mailing: Feb. 29, 2024, 12 pages.

English translation of Japanese Office Action mailed Jan. 19, 2024 for Japanese Application No. 2022-160947, 8 pages.

International Search Report and Written Opinion for International App. No. PCT/US2024/010875; Applicant: Inari Medical, Inc., Date of Mailing: Apr. 26, 2024, 15 pages.

International Search Report and Written Opinion for International App. No. PCT/US2023/079428; Applicant: Inari Medical, Inc., Date of Mailing: May 29, 2024, 18 pages.

Extended European Search Report for European Application No. 21818772.2, Applicant: Inari Medical, Inc., Date of Mailing: May 10, 9 pages.

Chinese Office Action received for Application No. 202111061740.2, Applicant: Inari Medical, Inc, Date of Mailing: May 23, 2024, 15 pages.

(56) References Cited

OTHER PUBLICATIONS

English translation of Japanese Office Action mailed Jun. 25, 2024 for Japanese Application No. 2022-574456, 5 pages.
Japanese Office Action mailed Jul. 8, 2024 for Japanese Application No. 2022-522892, 14 pages.
Chinese first Office Action mailed May 10, 2024 for Chinese Application No. 202080087833.X, 11 pages.
Partial Supplementary European Search Report received for European Application No. 21852966.7; Applicant: Inari Medical, Inc., Date of Mailing: Jul. 23, 2024, 12 pages.
Japanese Office Action mailed Aug. 2, 2024 for Japanese Application No. 2023-213724, 3 pages.
English Translation of Japanese Office Action mailed Jul. 23, 2024 for Japanese Application No. 2022-535535, 11 pages.
Extended European Search Report received for European Application No. 21895504.5; Applicant: Inari Medical, Inc., Date of Mailing: Aug. 16, 2024, 10 pages.
English translation of Japanese Office Action mailed Sep. 17, 2024 for Japanese Application No. 2023-203650, 6 pages.
English machine translation of Japanese Office Action mailed Oct. 10, 2024 for Japanese Application No. 2022-522892, 11 pages.

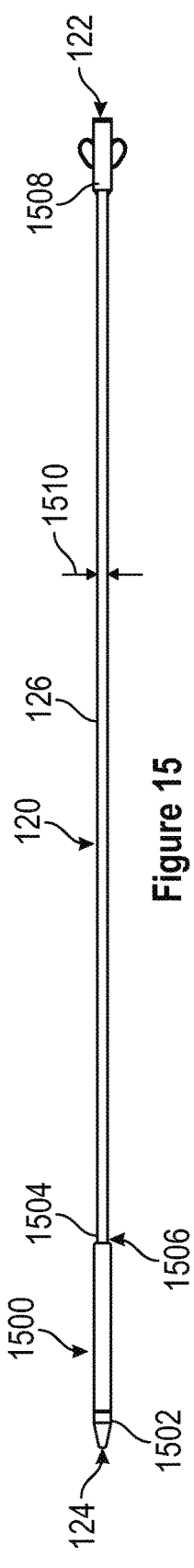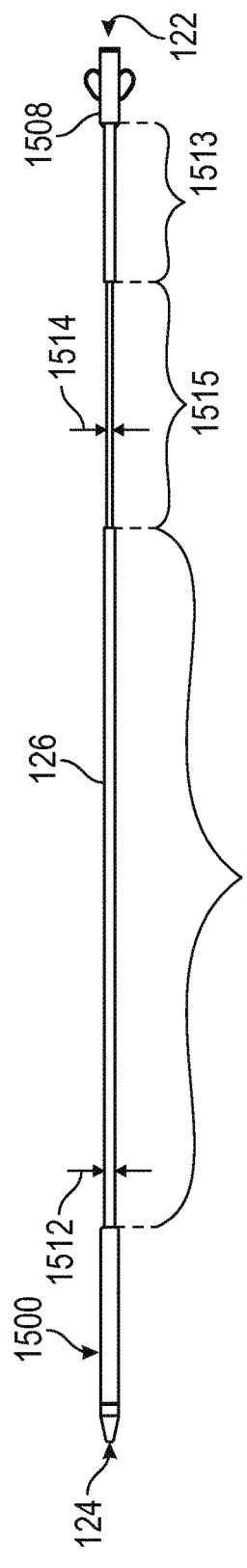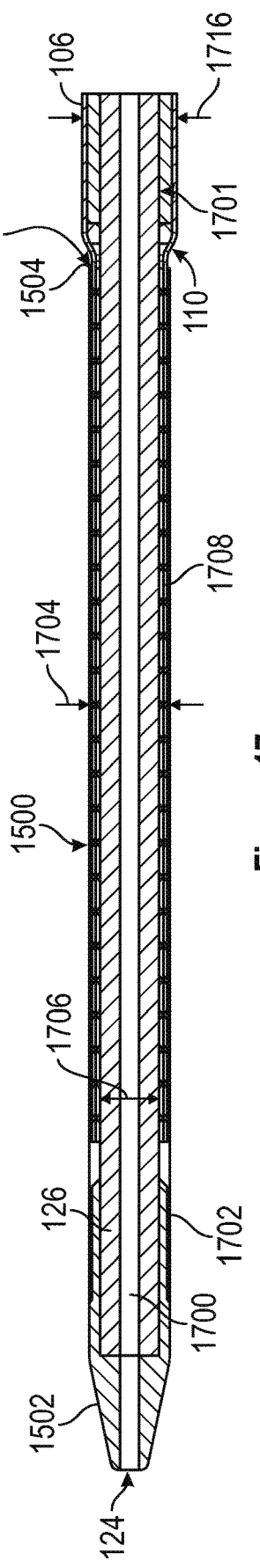

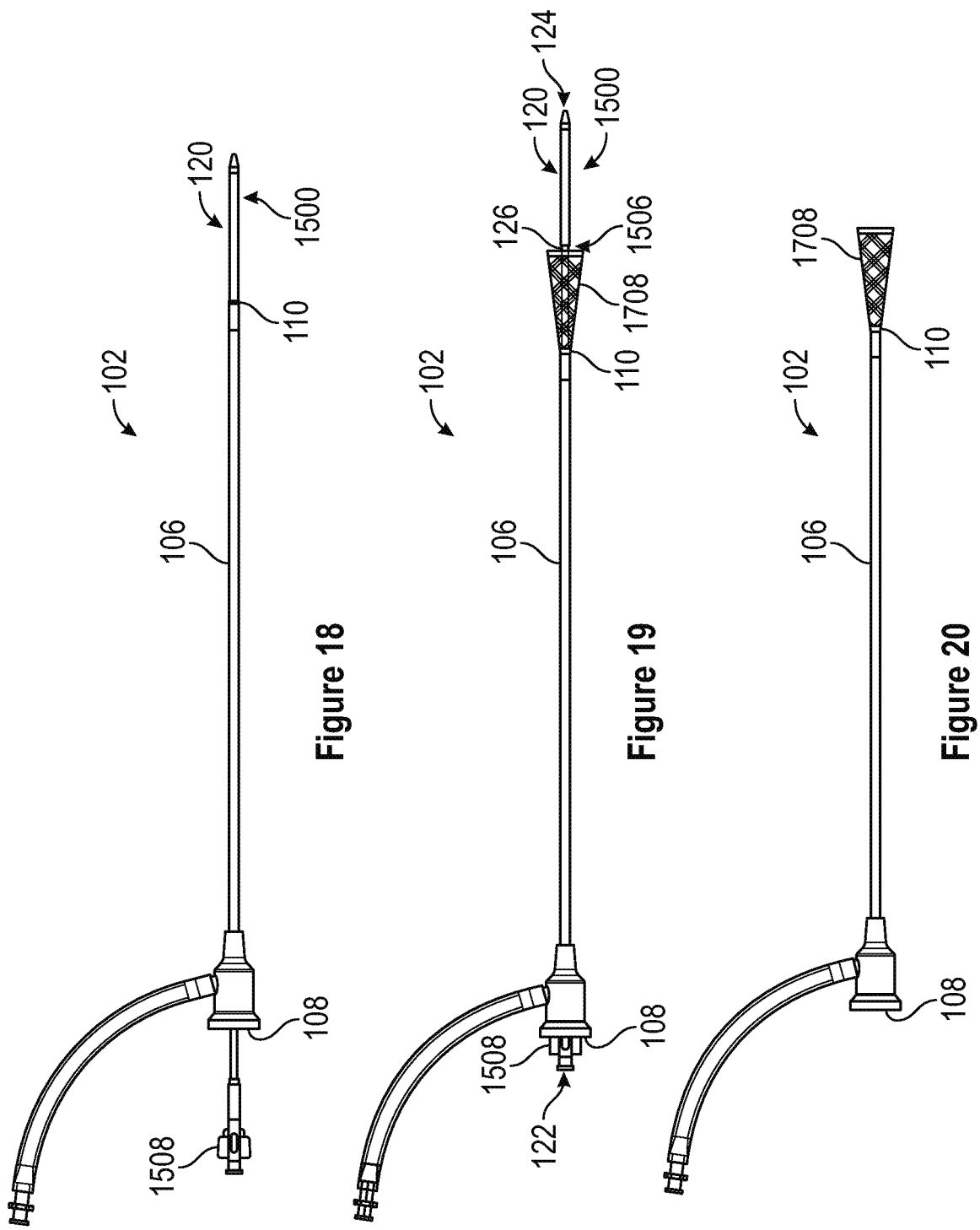

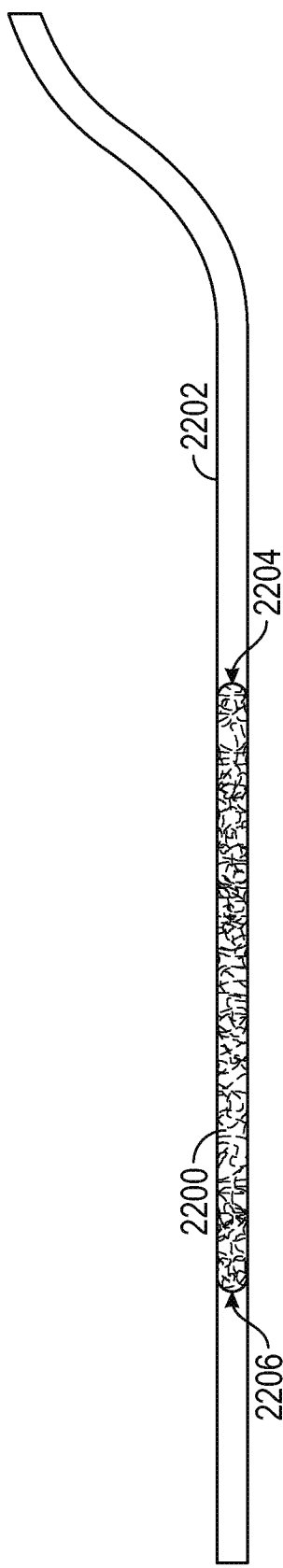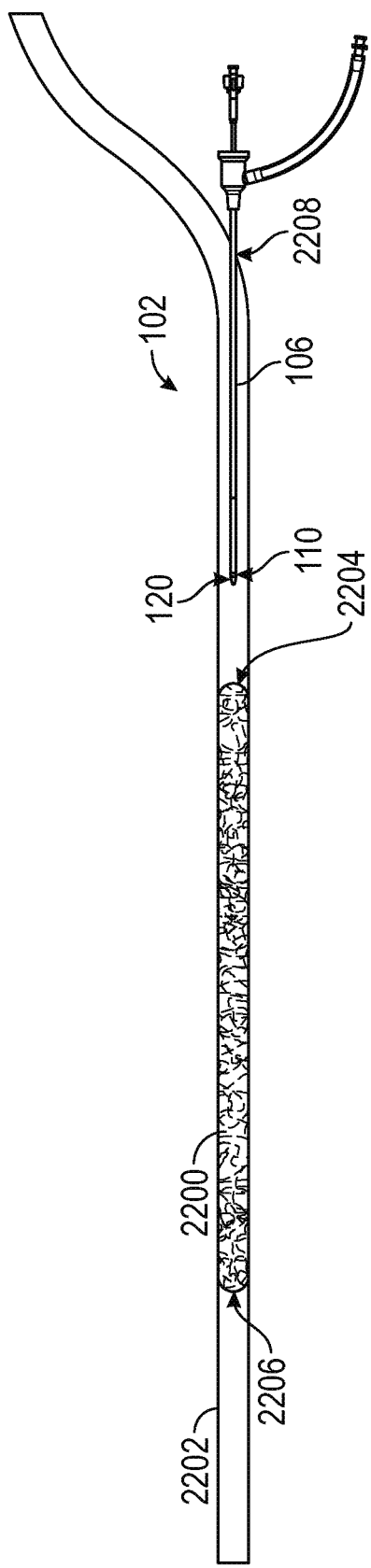
Figure 23-A
Figure 23-B

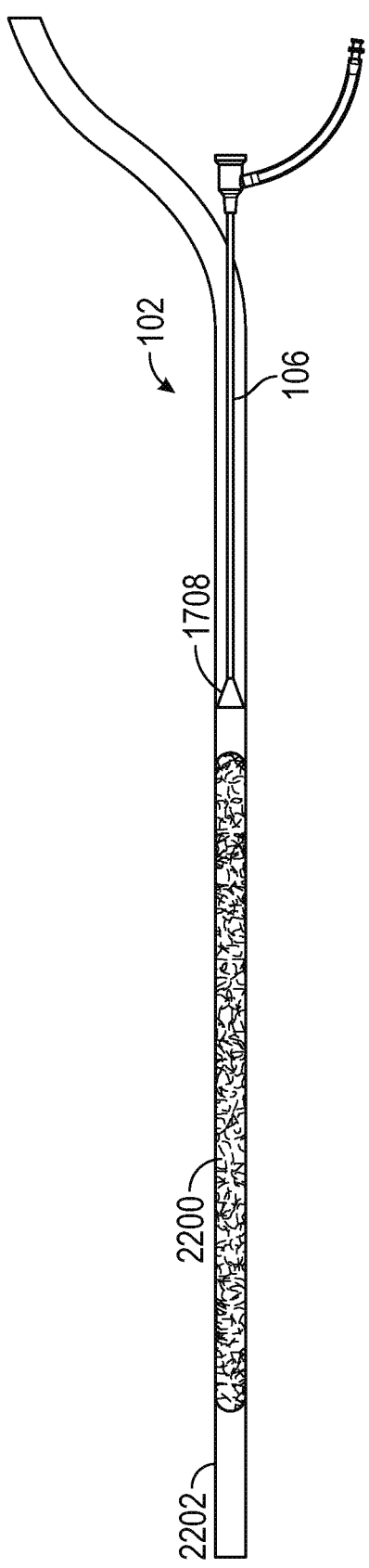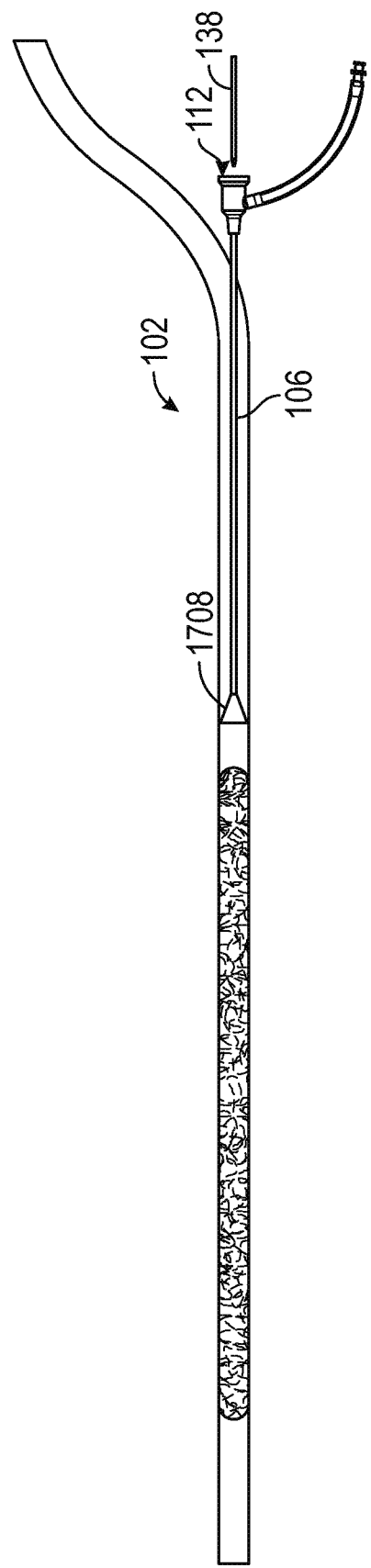

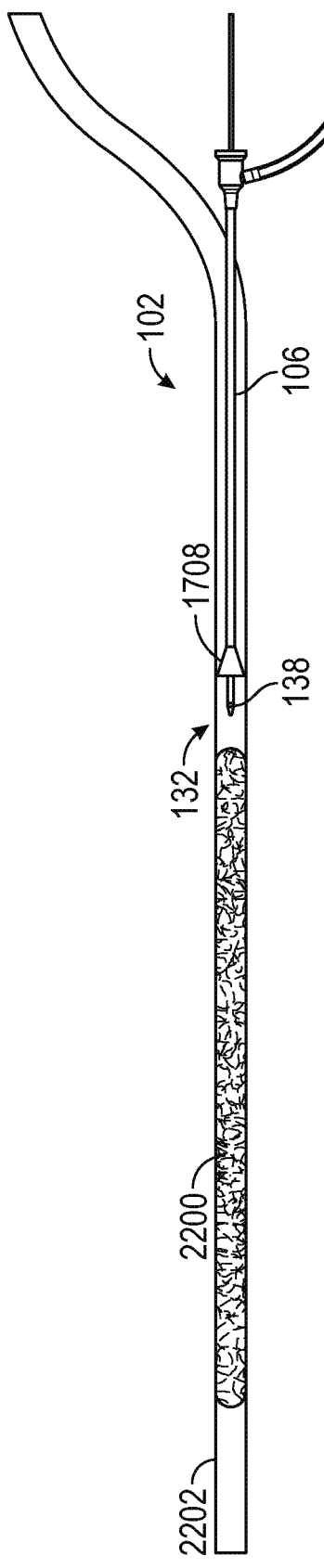
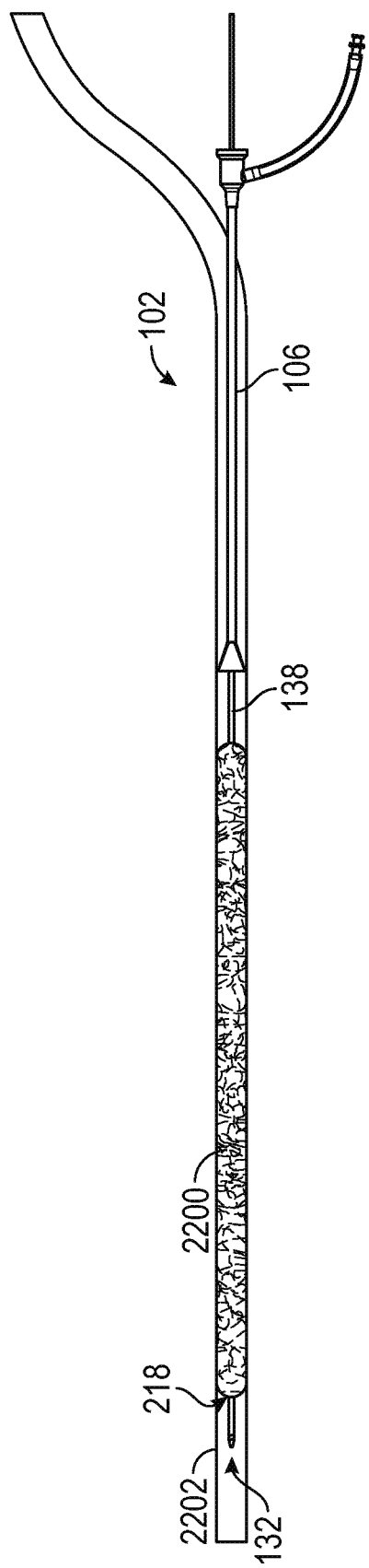
Figure 23-E
Figure 23-F

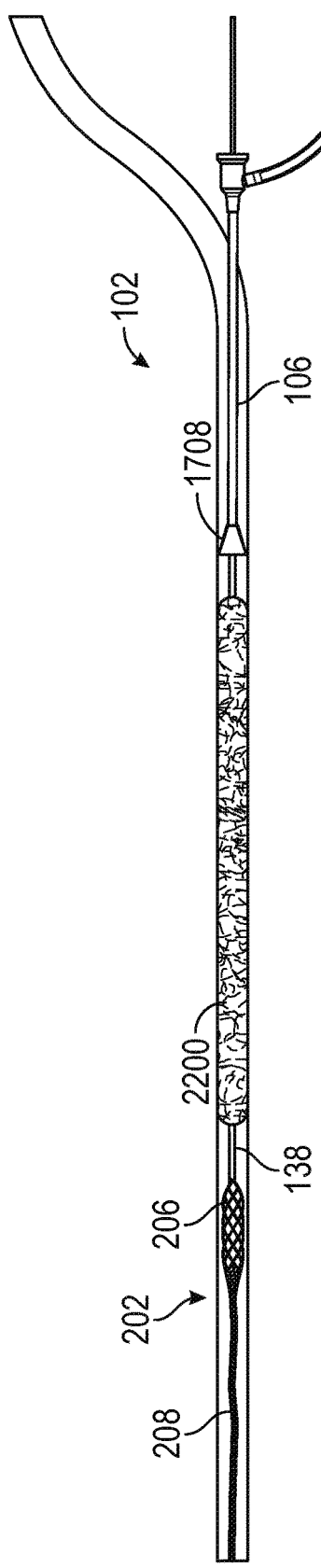
Figure 23-G
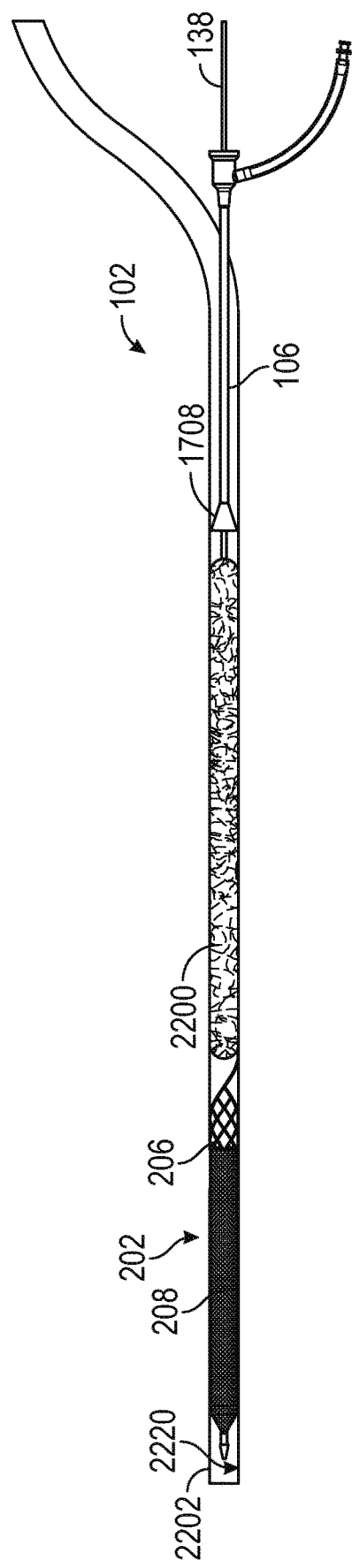
Figure 23-H

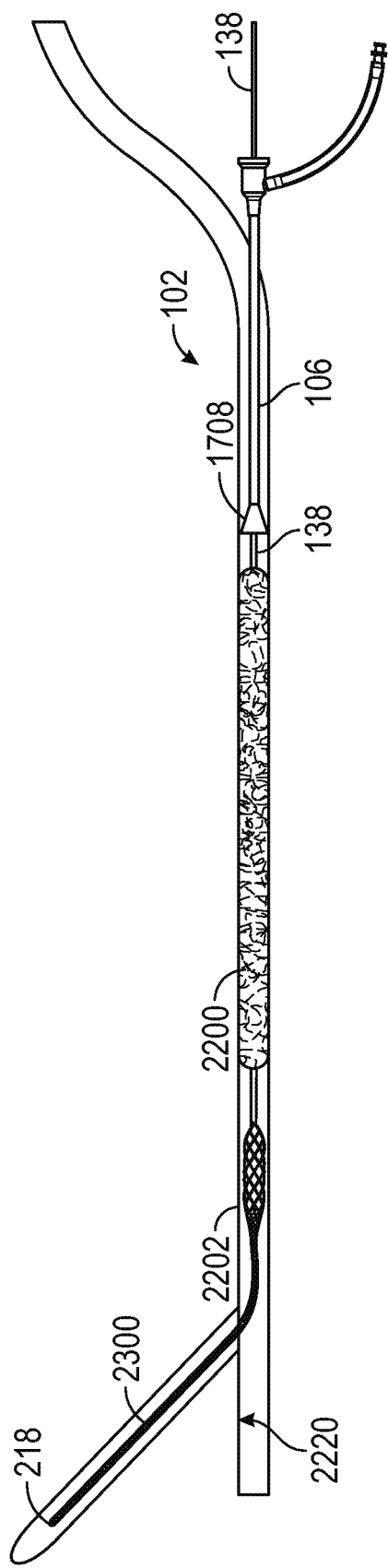
Figure 24-A
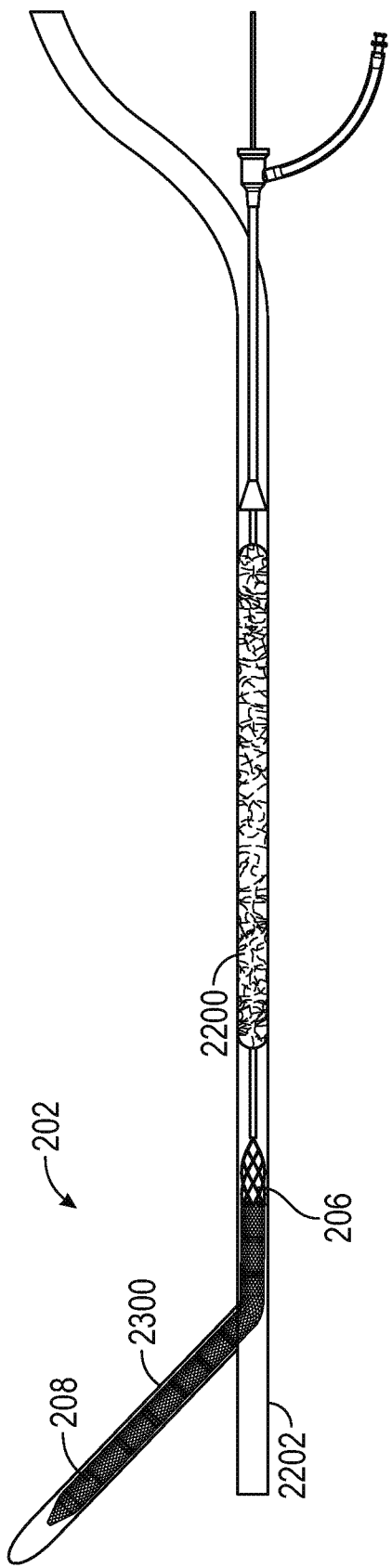
Figure 24-B

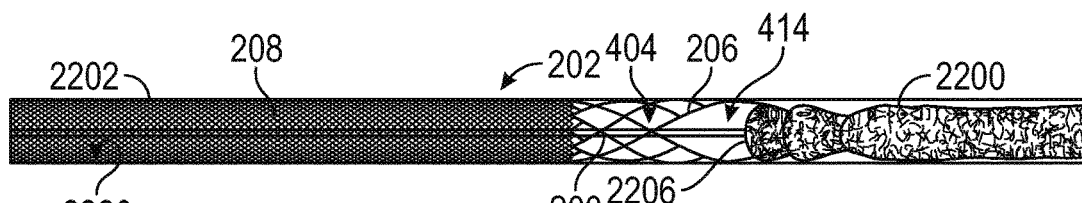
Figure 25-A
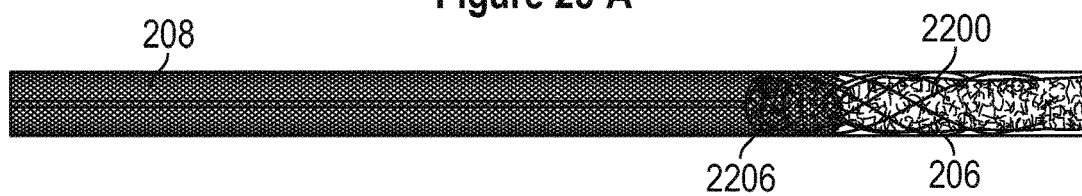
Figure 25-B
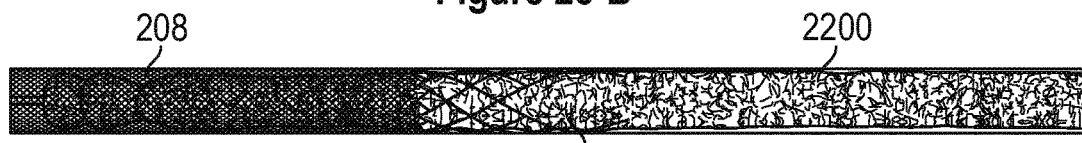
Figure 25-C
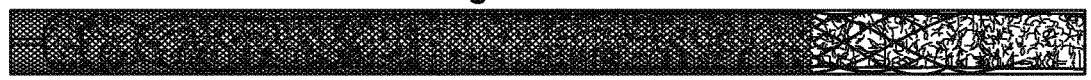
Figure 25-D
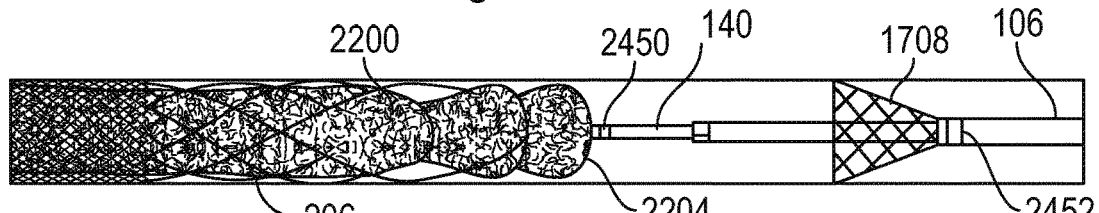
Figure 25-E
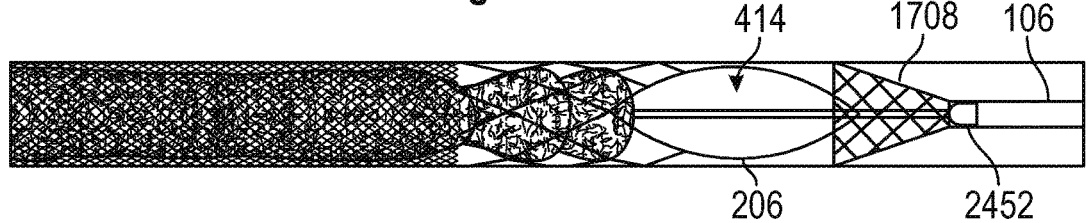
Figure 25-F
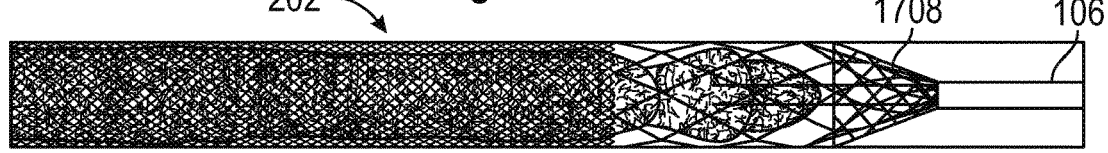
Figure 25-G
Figure 25-H

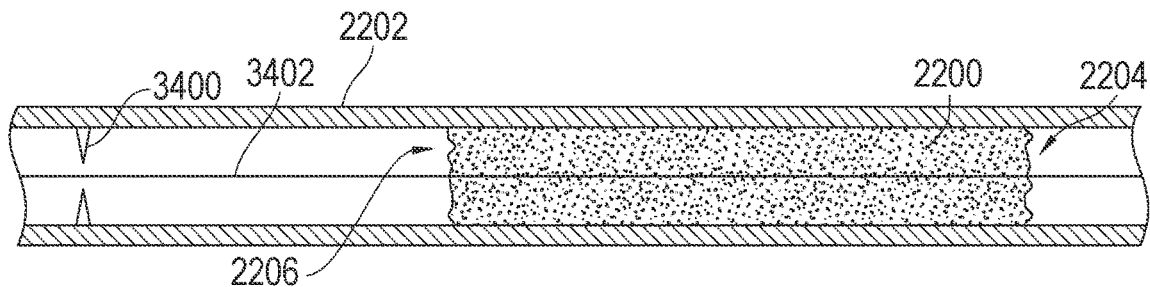
Figure 34-A
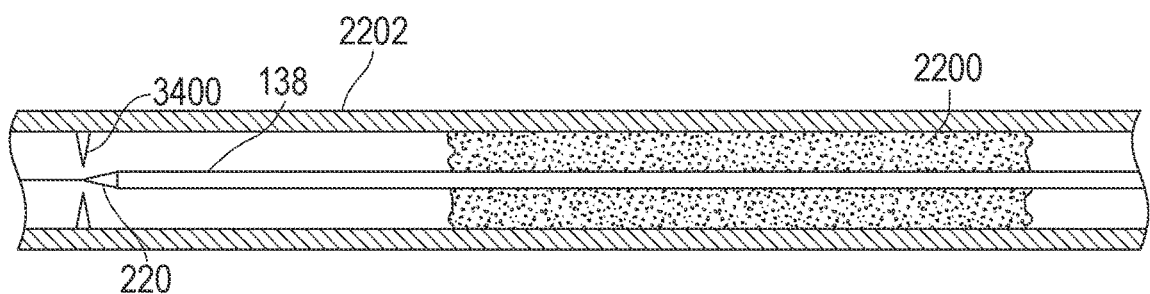
Figure 34-B
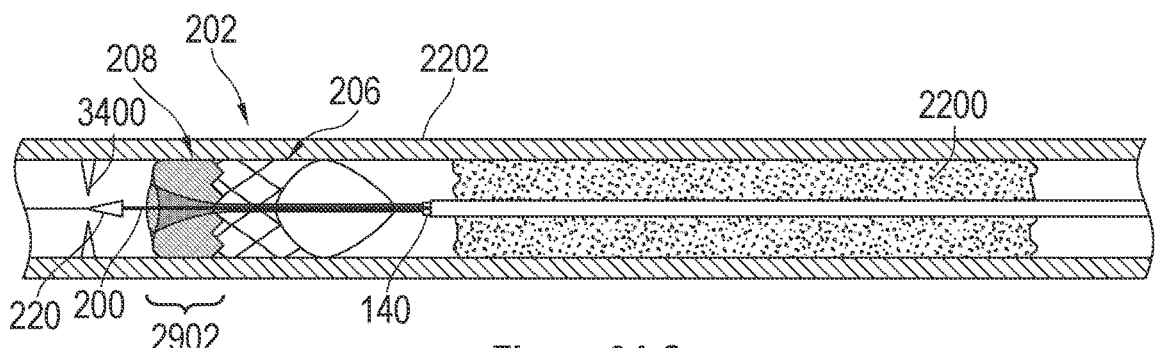
Figure 34-C
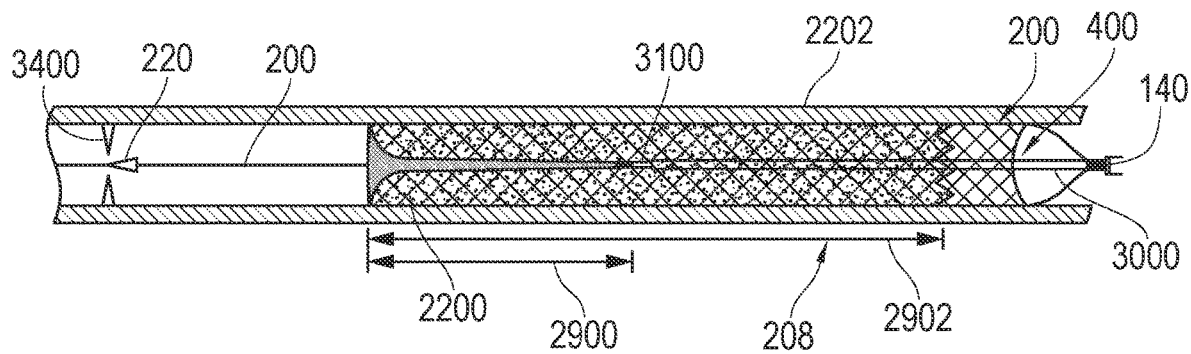
Figure 34-D

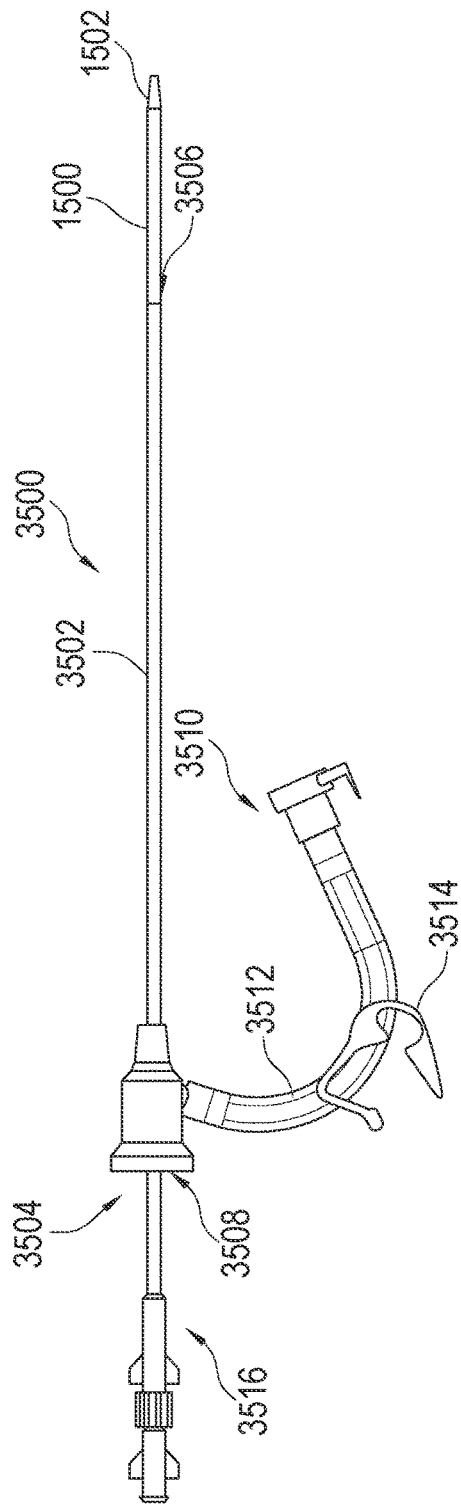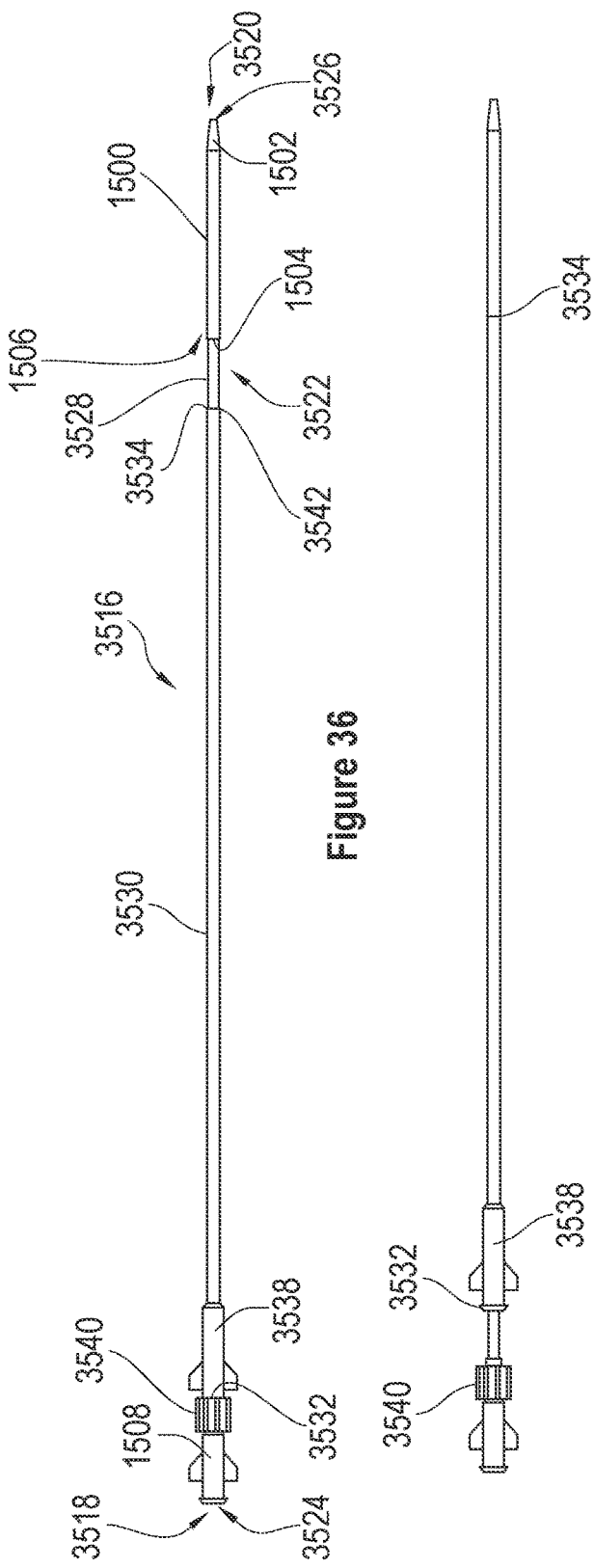
Figure 35
Figure 36
Figure 37

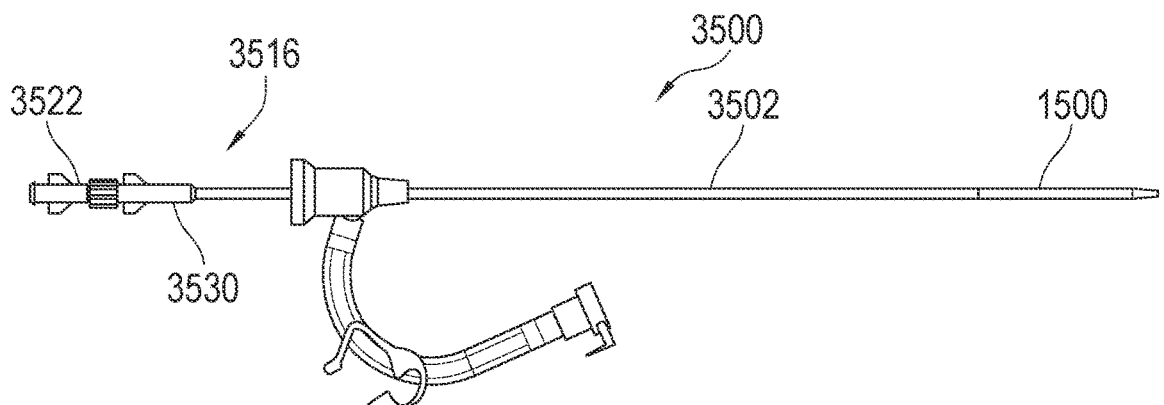
Figure 38-A
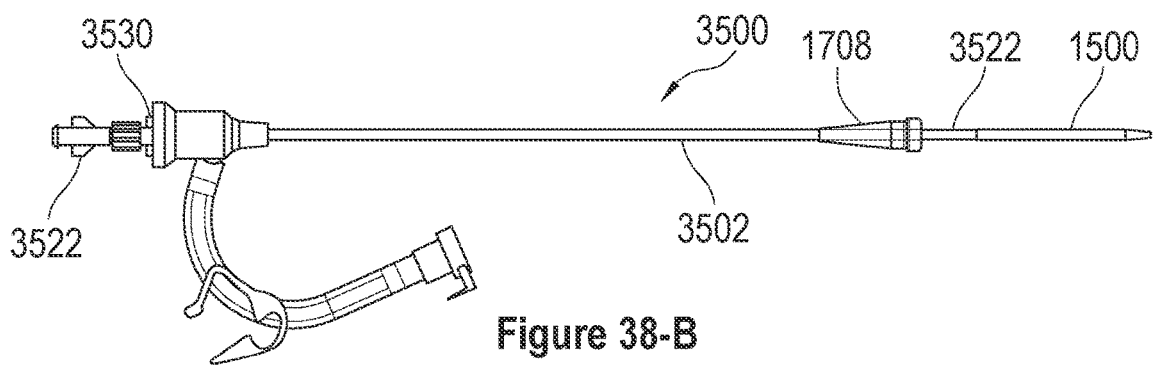
Figure 38-B
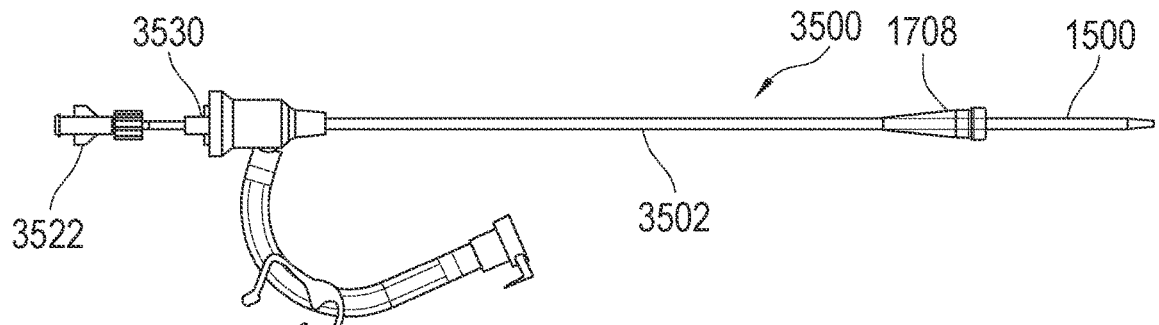
Figure 38-C
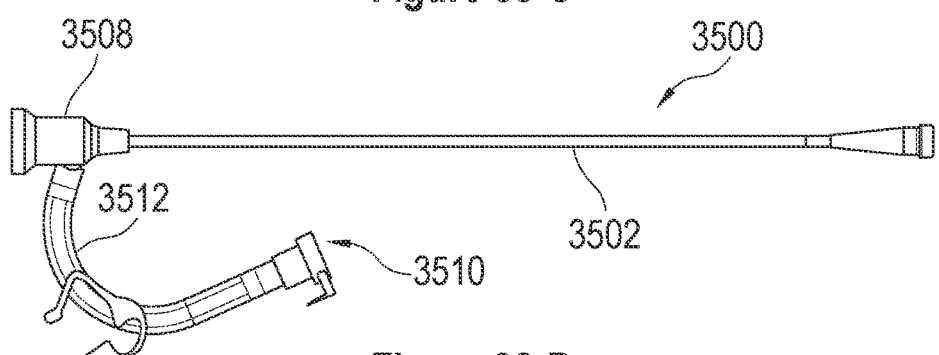
Figure 38-D

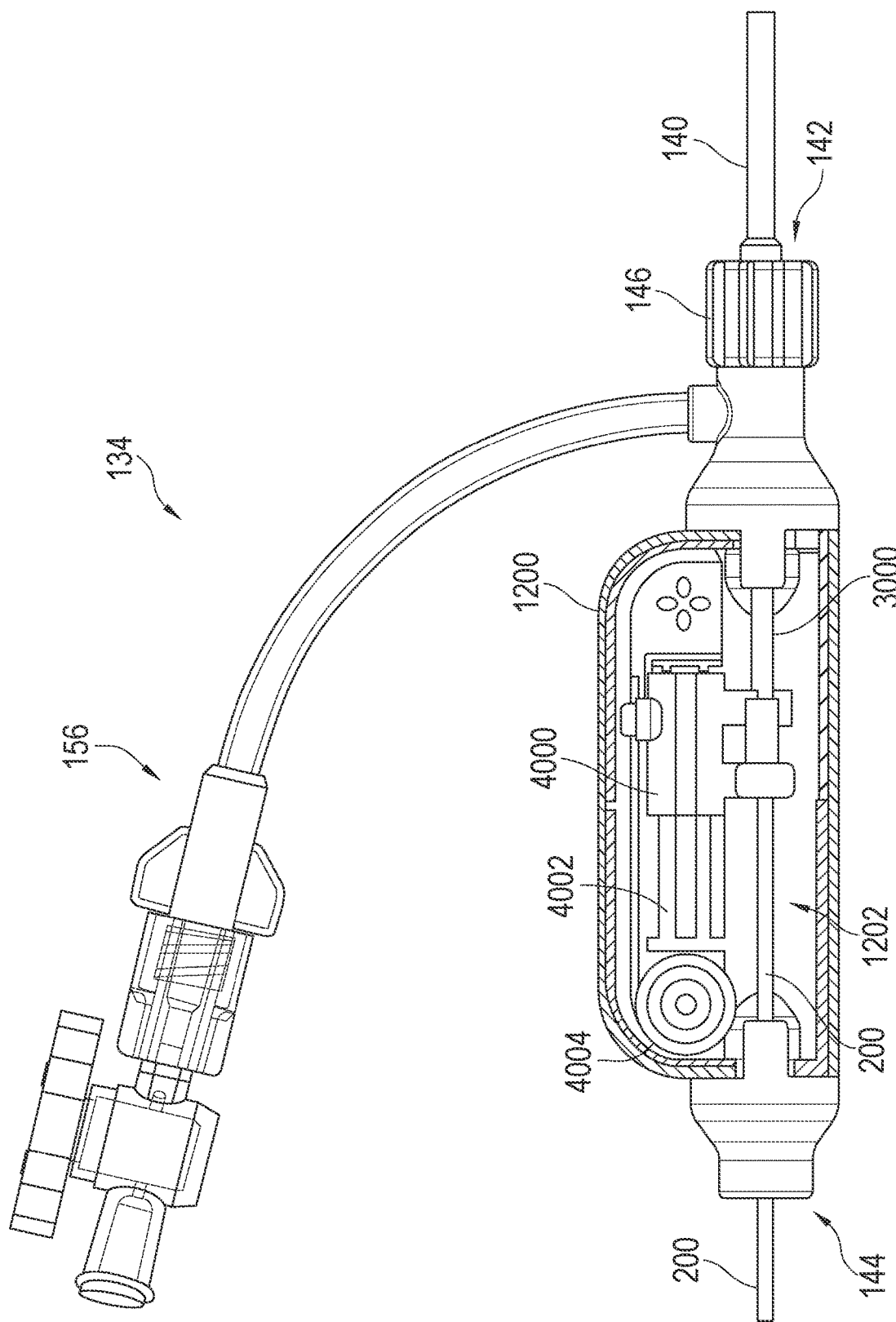

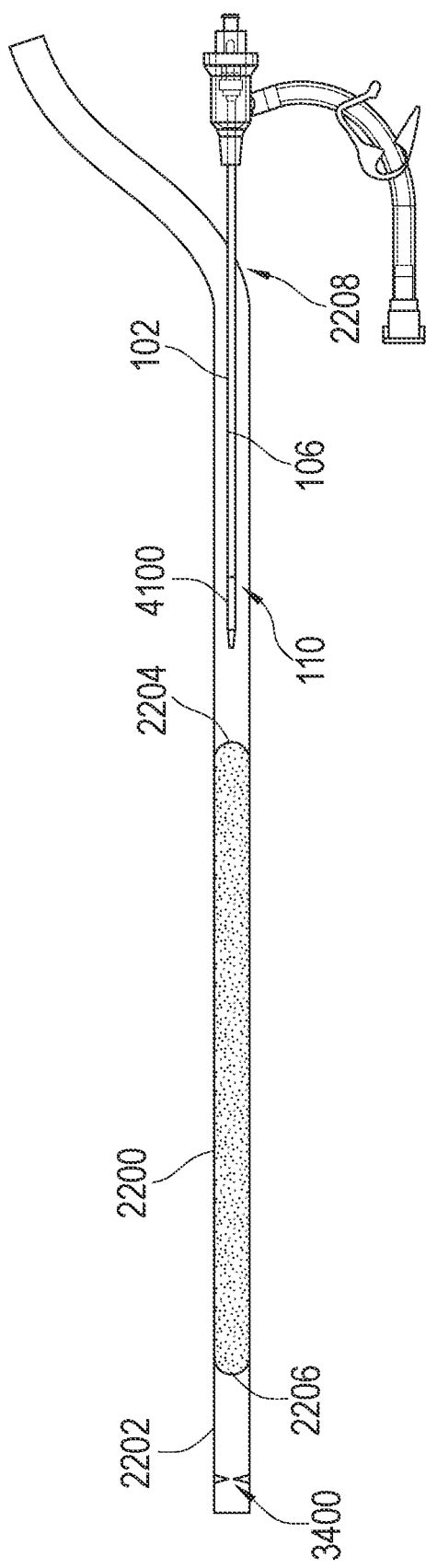
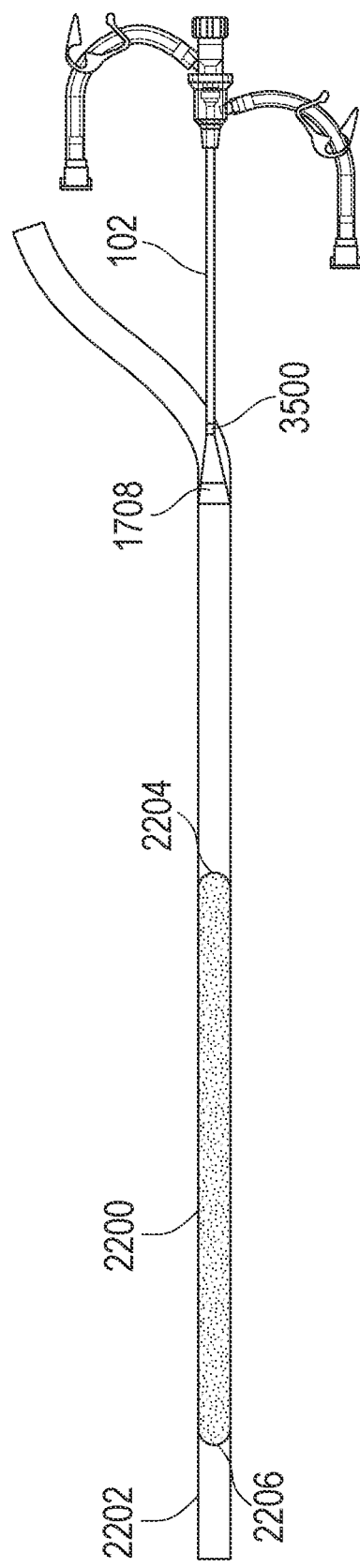
Figure 41-A   Figure 41-B

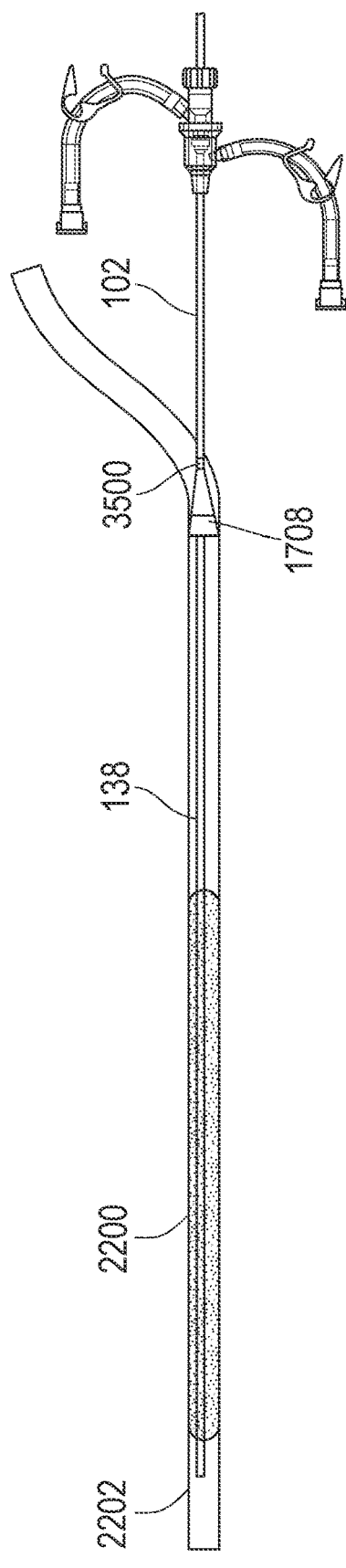
Figure 41-C
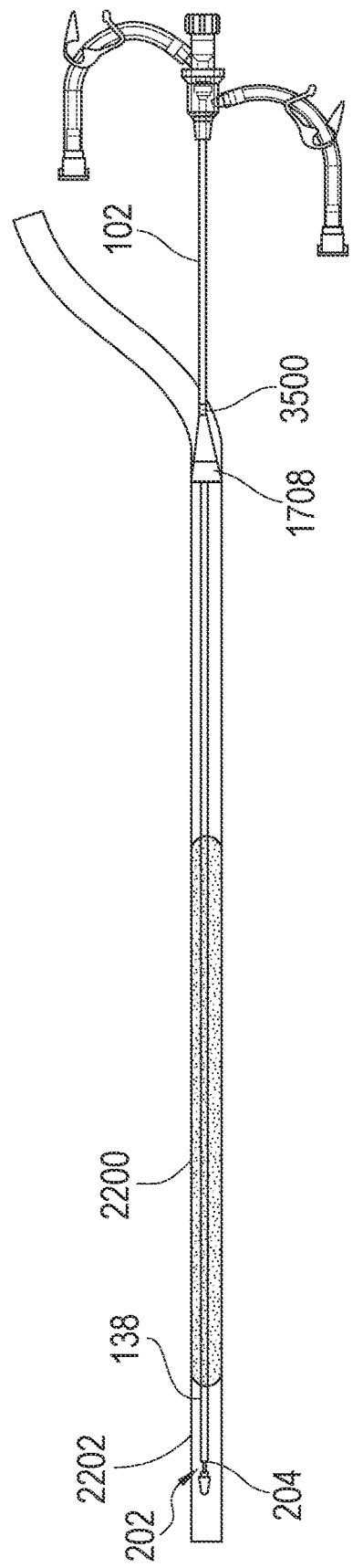
Figure 41-D

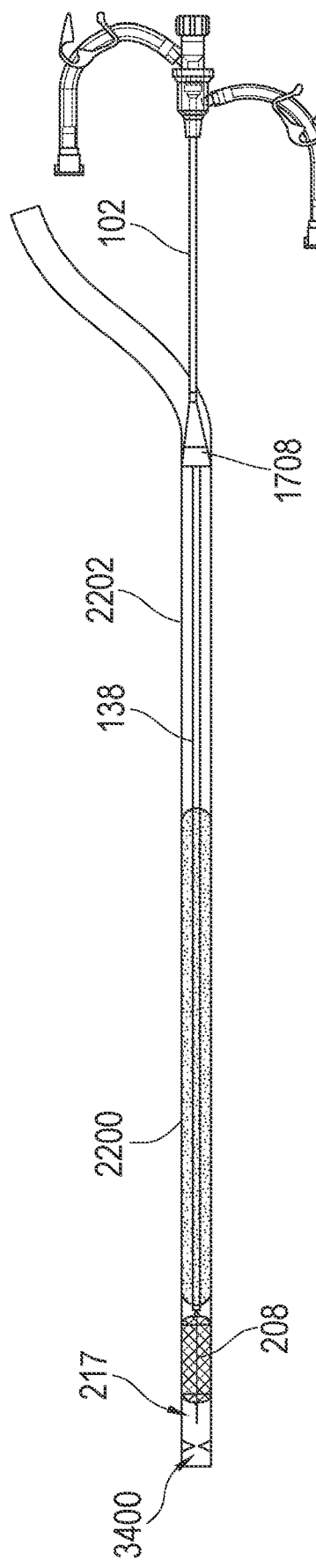
Figure 41-E
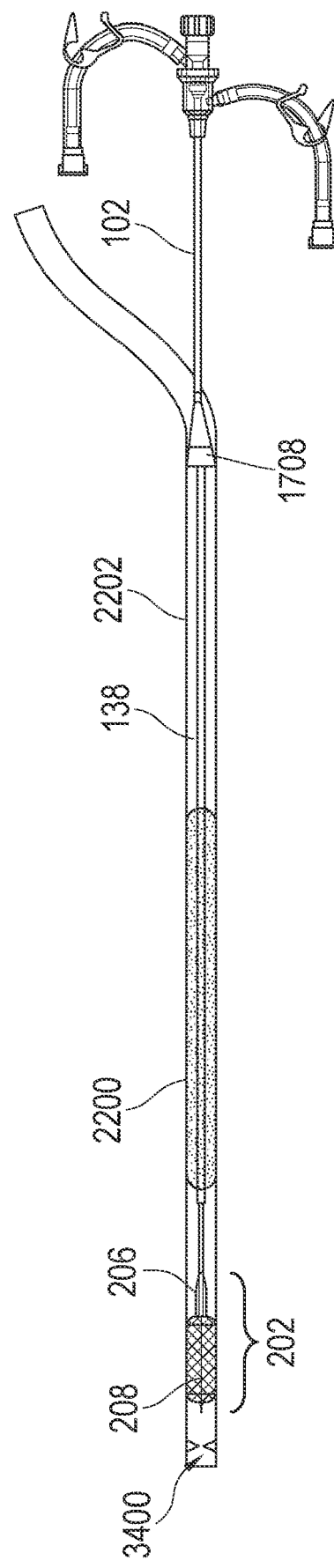
Figure 41-F

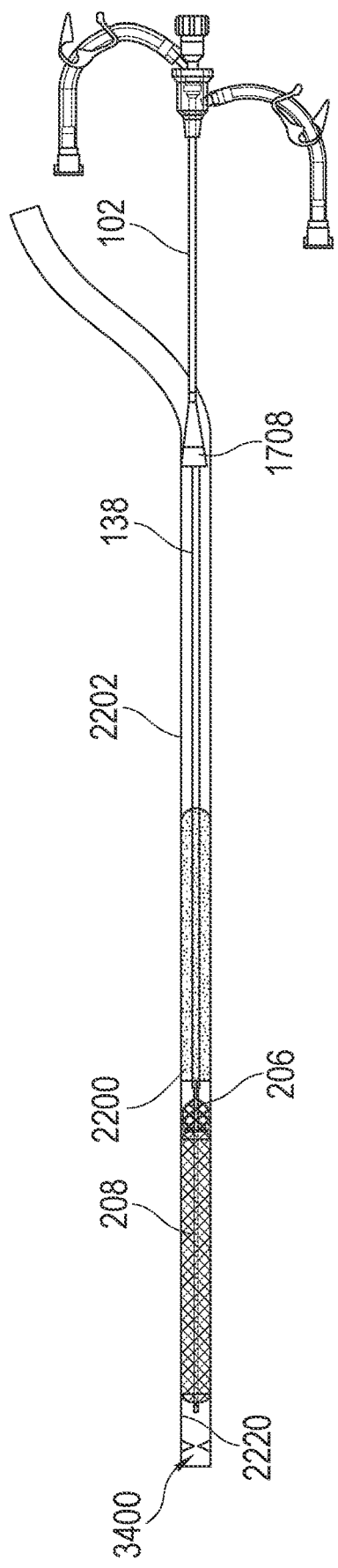
Figure 42-A
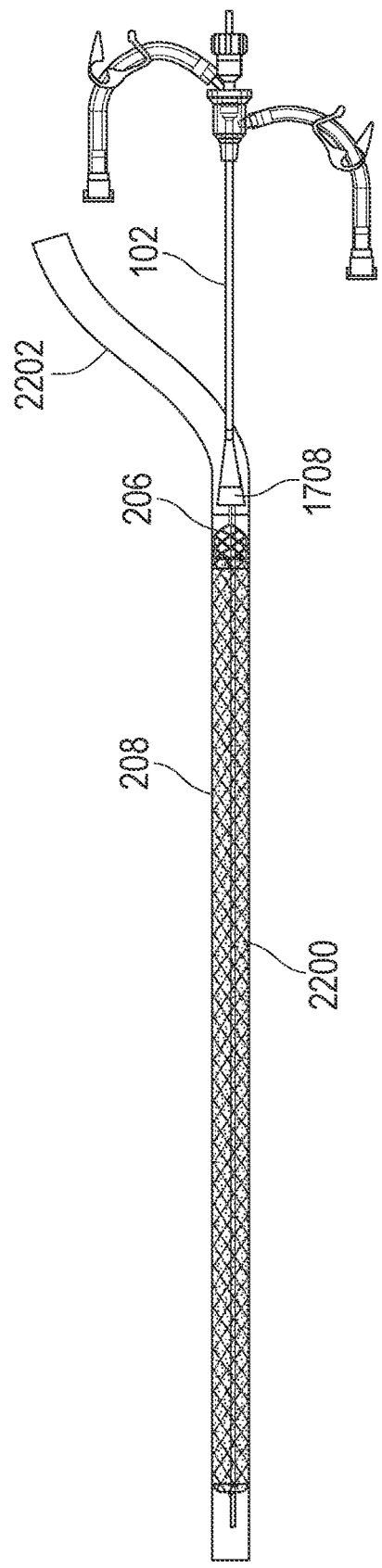
Figure 42-B

DEVICES AND METHODS FOR TREATING VASCULAR OCCLUSION

CROSS-REFERENCES TO RELATED APPLICATIONS

This application is a continuation of U.S. patent application Ser. No. 17/154,806, filed on Jan. 21, 2021, and titled "DEVICES AND METHODS FOR TREATING VASCULAR OCCLUSION," which is a continuation of U.S. patent application Ser. No. 16/160,920, filed on Oct. 15, 2018, and titled "DEVICES AND METHODS FOR TREATING VASCULAR OCCLUSION," now issued as U.S. Pat. No. 10,912,577, which is a continuation of U.S. patent application Ser. No. 15/498,320, filed on Apr. 26, 2017, and titled "DEVICES AND METHODS FOR TREATING VASCULAR OCCLUSION," now issued as U.S. Pat. No. 10,098,651, which claims the benefit of U.S. Provisional Application No. 62/444,705, filed on Jan. 10, 2017, and titled "INVERTED OR SELF-FEEDING DEVICES AND METHODS FOR TREATING VASCULAR OCCLUSION," each of which is herein incorporated by reference in its entirety.

This application is related to U.S. Provisional Application No. 62/245,935, filed on Oct. 23, 2015, and titled "INTRAVASCULAR TREATMENT OF VASCULAR OCCLUSION AND ASSOCIATED DEVICES, SYSTEMS AND METHODS"; U.S. patent application Ser. No. 15/268,296, filed on Sep. 16, 2016, and titled "INTRAVASCULAR TREATMENT OF VASCULAR OCCLUSION AND ASSOCIATED DEVICES, SYSTEMS AND METHODS"; U.S. patent application Ser. No. 15/268,406, filed on Sep. 16, 2016, and titled "INTRAVASCULAR TREATMENT OF VASCULAR OCCLUSION AND ASSOCIATED DEVICES, SYSTEMS AND METHODS"; and International Patent Application No. PCT/US2016/058536, filed on Oct. 24, 2016, and titled "INTRAVASCULAR TREATMENT OF VASCULAR OCCLUSION AND ASSOCIATED DEVICES, SYSTEMS AND METHODS", the entirety of each of which is hereby incorporated by reference herein.

BACKGROUND OF THE INVENTION

Thrombosis is a term for a blood clot occurring inside a blood vessel, and a venous thrombus is a blood clot (thrombus) that forms within a vein. A common type of venous thrombosis is a deep vein thrombosis (DVT). DVT is the formation of a blood clot (thrombus) within a deep vein, predominantly in the legs. Nonspecific signs may include pain, swelling, redness, warmness, and engorged superficial veins.

If the thrombus breaks off (embolizes) and flows towards the lungs, it can become a life-threatening pulmonary embolism (PE), a blood clot in the lungs. In addition to the loss of life that can arise from PE, DVT can cause significant health issues such as post thrombotic syndrome, which can cause chronic swelling, pressure, pain, and ulcers due to valve and vessel damage. Further, DVT can result in significant health-care costs either directly or indirectly through the treatment of related complications and inability of patients to work.

Three processes are believed to result in venous thrombosis. These are a decreased blood flow rate (venous stasis), increased tendency to clot (hypercoagulability), and changes to the blood vessel wall. DVT formation typically begins inside the valves of the calf veins, where the blood is relatively oxygen deprived, which activates certain biochemical pathways. Several medical conditions increase the risk for DVT, including diabetes, cancer, trauma, and antiphospholipid syndrome. Other risk factors include older age, surgery, immobilization (as with bed rest, orthopedic casts, and sitting on long flights), combined oral contraceptives, pregnancy, the postnatal period, and genetic factors. The rate of DVT increases dramatically from childhood to old age and in adulthood, about 1 in 1,000 adults develops it annually.

While current devices and methods of prevention and/or treatment of DVT exist, there are a number of shortcomings that have yet to be resolved, such as high incidence of DVT re-occurrence, use of devices not designed to remove large clot volumes, and/or complicated treatments involving multiple treatment devices and/or pharmaceuticals. Accordingly, new devices, systems, and methods of treating thrombus, and particularly DVT are desired.

BRIEF SUMMARY OF THE INVENTION

Aspects of the present disclosure relate to systems and methods for thrombus extraction, and particularly for thrombus extraction from a peripheral vasculature. The thrombus extraction devices of the present invention are designed to remove large clot volumes, including mature and organized clots, with reduced needs for pharmaceuticals, such as thrombolytics. This reduces risk of bleeding, post-treatment recovery time, and reduces health care procedure costs. The thrombus extraction device may comprise a self-expanding coring portion connected to a braided net so as to effectively core and separate large volumes of thrombus from large vessels in, for example, the venous system or arterial system while capturing the separated thrombus in the braided net.

One aspect of the present disclosure relates to method for removal of thrombus from a blood vessel in a body of a patient. The method includes: providing a thrombus extraction device. The thrombus extraction device can include: a proximal self-expanding member formed of a fenestrated structure, and a substantially cylindrical portion formed of a net-like filament mesh structure having a proximal end coupled to a distal end of the fenestrated structure. The method includes: advancing a catheter constraining the thrombus extraction device through a vascular thrombus, deploying the thrombus extraction device by stacking a portion of the net-like filament mesh structure outside of the catheter by distally advancing the self-expanding member until the self-expanding member is beyond a distal end of the catheter; retracting the self-expanding member relative to the distal end of the net-like filament mesh structure to unstack the portion of the net-like filament mesh structure and to separate a portion of the thrombus from the vessel wall and to capture the portion of the thrombus within the net-like filament mesh structure; and withdrawing the thrombus extraction device from the body to remove thrombus from the patient.

In some embodiments, advancing the catheter through the vascular thrombus includes inserting the catheter into the blood vessel until a radiopaque distal tip of the catheter is past the thrombus portion. In some embodiments, stacking a portion of the net-like filament mesh structure includes: fixing a position of the distal end of the net-like filament mesh structure; and distally advancing the self-expanding member relative to the distal end of the net-like filament mesh structure.

In some embodiments, the position of the distal end of the net-like filament mesh structure is fixed proximal relative to one or several valves in the body of the patient. In some embodiments, the position of the distal end of the net-like filament mesh structure is fixed in the inferior vena cava, at one or several valves, and/or distal to one or several valves. In some embodiments, the valve is located in the blood vessel containing the thrombus. In some embodiments, the valve is located in a second blood vessel, wherein the second blood vessel is connected to the blood vessel containing the thrombus.

In some embodiments, stacking a portion of the net-like filament mesh structure includes changing the braid angle of portion of the net-like filament mesh structure. In some embodiments, the braid angle of the portion of the net-like filament mesh structure is greater than 45° when stacked. In some embodiments, a diameter of the portion of the net-like filament mesh structure is greater than a diameter of the fenestrated structure. In some embodiments, the catheter is inserted into the blood vessel through a popliteal access site and the catheter is distally advanced from the popliteal access site. In some embodiments, the net-like filament mesh structure is interwoven on the fenestrated structure.

In some embodiments the method includes moving the fenestrated structure to full expansion. In some embodiments, moving the fenestrated structure to full expansion includes retracting a stop shaft relative to the fenestrated structure. In some embodiments, the stop shaft is retracted relative to the fenestrated structure via movement of a plunger from a first position to a second position. In some embodiments, the stop shaft is retracted relative to the fenestrated structure via movement of a shuttle from a first position to a second position. In some embodiments, the shuttle is moved from a first position to a second position via a force applied to the shuttle by a spring. In some embodiments, the stop shaft applies a constant pressure on the stop ring. In some embodiments, the stop shaft is replaced by a tether, or filament, to engage the fenestrated structure. In some embodiments, the stop shaft can comprise a filament such as a metal or polymeric filament, a monofilament, and/or a braided or woven strand. This tether or filament can be attached proximally to the catheter hub or handle, and can apply constant tension when the fenestrated structure is deployed.

In some embodiments, advancing the catheter through the vascular thrombus includes inserting the catheter into the blood vessel through a funnel catheter including: an elongate sheath; and a self-expanding funnel coupled to a distal end of the elongate sheath. In some embodiments, withdrawing the thrombus extraction device from the body to remove thrombus from the patient includes retracting the thrombus extraction device until at least a portion of the self-expanding member is contained within the self-expanding funnel. In some embodiments, the at least a portion of the self-expanding member contained within the self-expanding funnel includes an opening of the self-expanding member. In some embodiments, the method includes simultaneously proximally retracting the thrombus extraction device and the funnel catheter from the patient. In some embodiments, the opening of the thrombus extraction device is maintained within the self-expanding funnel during the simultaneous proximal retraction of the thrombus extraction device and the funnel catheter from the patient.

One aspect of the present disclosure relates to a thrombus extraction device for removal of a vascular thrombus from a blood vessel of a patient. The thrombus extraction device includes: a catheter having a proximal end and a distal end, an outer shaft defining a first lumen, a coring element shaft defining a second lumen, a stop shaft, and a tip shaft. In some embodiments, the stop shaft can define a third lumen, and in some embodiments, the tip shaft can define a tip lumen. In some embodiments, the coring element shaft is coaxial the first lumen and the tip shaft is coaxial the second lumen. The thrombus extraction device includes a self-expanding coring element formed of a fenestrated structure having an opening at a proximal end and configured to core and separate a portion of the vascular thrombus from the blood vessel. In some embodiments, the proximal end of the fenestrated structure is coupled to a distal end of the coring element shaft. The thrombus extraction device can include an expandable cylindrical portion formed of a filament mesh structure that can capture the vascular thrombus portion. In some embodiments, a proximal end of the mesh structure is coupled to a distal end of the fenestrated structure. In some embodiments, the stop shaft is displaceable independent of the tip shaft with respect to the coring element shaft and the proximal end the self-expanding coring element to move the self-expanding coring element to an expanded state.

In some embodiments, the filament mesh structure is interwoven on the fenestrated structure. In some embodiments the thrombus extraction device further includes an expansion mechanism that can maintain a desired radial force on a vessel wall with the self-expanding coring element. In some embodiments, the expansion mechanism can hold the fenestrated structure in full expansion. In some embodiments, the expansion mechanism includes a ring feature of the fenestrated structure and a stop feature that can engage with the ring feature when the fenestrated structure is in full expansion. In some embodiments, the stop feature can engage with the ring feature when the fenestrated structure is in full expansion and throughout the full travel and/or diameter range of the fenestrated structure. In some embodiments, the stop feature can be a tab on a stop shaft. In some embodiments, the tab can engage with the ring feature, and the stop shaft is coaxial with the first lumen.

In some embodiments, the thrombus extraction device can include a handle including a plunger that can control a relative position of the stop shaft with respect to the coring element shaft and that can selectively secure the relative position of the stop shaft with respect to the coring element shaft. In some embodiments, the thrombus extraction device further includes a handle having a spring connected to the stop shaft via a displaceable shuttle. In some embodiments, the shuttle is displaceable between a first position in which self-expanding coring element is collapsed and a second position in which self-expanding coring element is expanded. In some embodiments, the spring includes at least one of: a constant force spring; a tension spring; or a compression spring. In some embodiments, the spring can include any means for applying force to the stop including, for example, an elastomer, a pressure chamber, a hydraulic or pneumatic piston, or a torsion spring.

One aspect of the present disclosure relates to a funnel catheter for accessing and removing thrombus within a blood vessel of a patient. The funnel catheter includes: an elongate sheath having a proximal end, a distal end, and a lumen extending therebetween; a self-expanding funnel coupled to the distal end of the elongate sheath; and a dilator assembly that can be received within the lumen of the capture sheath. The dilator assembly includes: an obturator having an elongate shaft having proximal end, a distal end, and a capture sheath proximate to the distal end, which capture sheath can retain the self-expanding funnel in a constrained configuration. In some embodiments, the dilator assembly can include a moveable shaft coaxially extending along a portion of the elongate shaft of the obturator between the proximal end of the obturator and the capture sheath. In some embodiments the moveable shaft includes a mating feature at a distal end of the moveable shaft, which mating feature can mate with the capture sheath.

In some embodiments, the funnel catheter includes a sealed hub located at the proximal end of the elongate sheath. In some embodiments, the sealed hub can include an aspiration port. In some embodiments, the self-expanding funnel has a diameter equal to or less than a diameter of the capture sheath when the self-expanding funnel is in the constrained configuration. In some embodiments, the moveable shaft has a diameter equal to the diameter of the capture sheath. In some embodiments, the moveable shaft is moveable between a loading position and a retracting position. In some embodiments, the moveable shaft includes a connecting feature that can connect the moveable shaft to the proximal end of the proximal end of the elongate shaft when the moveable shaft is in the loading position. In some embodiments, the mating feature of the moveable shaft can mate with the capture sheath when the moveable shaft is in the retracting position.

One aspect of the present disclosure relates to a method of accessing and removing thrombus from a venous vessel of a patient. The method includes percutaneously accessing a venous vessel of a patient through an access site with a funnel catheter. In some embodiments, the funnel catheter includes an elongate sheath defining a lumen, a self-expanding funnel coupled to a distal end of the elongate sheath, and a dilator assembly including: an elongate obturator extending through the lumen and retaining the self-expanding funnel in a constrained configuration within a capture sheath of the obturator; and a moveable shaft coaxially extending along a portion of the elongate obturator. In some embodiments, the access site can be a popliteal access site, a femoral access site, a mid-femoral access site, a tibial access site, a contralateral access site, or an internal jugular access site. The method includes: advancing a distal end of the funnel catheter to a position proximal of a thrombus; deploying the self-expanding funnel from the constrained configuration within the capture sheath to an expanded configuration free of the capture sheath; capturing thrombus in the self-expanding funnel; and aspirating the captured material through the lumen of the elongate sheath.

In some embodiments, deploying the self-expanding funnel includes: distally advancing the dilator assembly relative to the elongate sheath to unsheathe the self-expanding funnel from the constrained configuration to the expanded configuration; displacing the moveable shaft from a loading position to a retracting position; and removing the dilator assembly from the funnel catheter by proximally retracting the dilator assembly through the deployed self-expanding funnel and through the lumen of the elongate sheath. In some embodiments, deploying the self-expanding funnel can include: proximally retracting the elongate sheath over the dilator assembly to unsheathe the self-expanding funnel from the constrained configuration to the expanded configuration; displacing the moveable shaft from a loading position to a retracting position; and removing the dilator assembly from the funnel catheter by proximally retracting the dilator assembly through the deployed self-expanding funnel and through the lumen of the elongate sheath. In some embodiments, a mating feature of the moveable shaft mates with the capture sheath when the moveable shaft is in the retracting position In some embodiments, the method includes inserting a catheter constraining a thrombus extraction device through the lumen of the elongate sheath so that a distal tip of the catheter is distally past the vascular thrombus portion, deploying the thrombus extraction device from the catheter, and proximally retracting the thrombus extraction device relative to the funnel catheter until an opening of the thrombus extraction device is within the self-expanding funnel. In some embodiments, the method includes percutaneously accessing a venous vessel of a patient with an introducer sheath through the access site. In some embodiments, percutaneously accessing the venous vessel of the patient with the funnel catheter through the access site includes inserting the funnel catheter into the venous vessel through the introducer sheath. In some embodiments, the method includes simultaneously proximally retracting the thrombus extraction device and the funnel catheter from the patient via the introducer sheath. In some embodiments, the opening of the thrombus extraction device is maintained within the self-expanding funnel during the simultaneous proximal retraction of the thrombus extraction device and the funnel catheter from the patient.

One aspect of the present disclosure relates to a method for removal of thrombus from a blood vessel in a body of a patient. The method includes providing a thrombus extraction device having a proximal self-expanding member formed of a unitary fenestrated structure, a substantially cylindrical portion formed of a net-like filament mesh structure having a non-everted portion coupled to a distal end of the unitary fenestrated structure and an everted portion extending proximally through the unitary fenestrated structure, and an inner shaft member coupled to a distal end of the net-like filament mesh structure. The method can include: advancing a catheter constraining the thrombus extraction device through a vascular thrombus; and deploying the thrombus extraction device by either advancing the unitary fenestrated structure beyond a distal end of the catheter or retracting the catheter relative to the unitary fenestrated structure thus exposing the unitary fenestrated structure and the non-everted portion of the net-like filament mesh structure distally past a portion of the thrombus and allowing expansion of the unitary fenestrated structure to engage a wall of the blood vessel. The method can include: distally advancing at least a part of the everted portion of the net-like filament mesh structure through the unitary fenestrated structure; retracting the thrombus extraction device to separate a portion of the thrombus from the vessel wall and to capture the portion of the thrombus within the net-like filament mesh structure; and withdrawing the thrombus extraction device from the body to remove thrombus from the patient.

In some embodiments, advancing the catheter through the vascular thrombus includes inserting the catheter into the blood vessel until a radiopaque distal tip of the catheter is past the thrombus portion. In some embodiments, distally advancing at least a part of the everted portion includes: fixing a position of a radiopaque tip of the inner shaft; and proximally retracting the unitary fenestrated structure. In some embodiments, the position of the radiopaque tip is fixed proximal relative to a valve of the blood vessel. In some embodiments, the catheter is inserted into the blood vessel through a popliteal access site and the catheter is distally advanced from the popliteal access site.

In some embodiments, distally advancing at least a part of the everted portion of the net-like filament mesh structure through the unitary fenestrated structure increases a size of the non-everted portion of the net-like filament mesh structure relative to a size on the everted portion of the net-like filament mesh structure. In some embodiments, the at least a part of the everted portion of the net-like filament mesh structure is distally advanced through the unitary fenestrated structure until the portion of the thrombus is wholly contained in the net-like filament mesh structure.

In some embodiments, the net-like filament mesh structure everts on itself. In some embodiments, the method includes limiting proximal movement of the inner shaft with respect to the unitary fenestrated structure to prevent full eversion of the net-like filament mesh. In some embodiments, the net-like filament mesh structure is integrally formed on the unitary fenestrated structure. In some embodiments, the net-like filament mesh structure everts inside of and/or on the unitary fenestrated structure. In some embodiments, the method includes: retracting an intermediate shaft member relative to the catheter and the unitary fenestrated structure until a stop feature fixed on the intermediate shaft member engages a corresponding feature on the fenestrated structure; and locking the intermediate shaft member with respect to the unitary fenestrated structure for full expansion of the unitary fenestrated structure. In some embodiments, the method includes unlocking the intermediate shaft member with respect to the unitary fenestrated structure prior to withdrawing the thrombus extraction device from the body. In some embodiments, the thrombus extraction device as constrained within the catheter includes the non-everted portion and the everted portion extending proximally through the unitary fenestrated structure.

One aspect of the present disclosure relates to a thrombus extraction device for removal of a vascular thrombus from a blood vessel of a patient. The thrombus extraction device can include a catheter having a proximal end and a distal end, an outer shaft defining a first lumen, a first intermediate shaft defining a second lumen, and an inner shaft. In some embodiments, the first intermediate shaft is coaxial the first lumen and the inner shaft is coaxial the second lumen. The thrombus extraction device can include a self-expanding coring element formed of a unitary fenestrated structure having an opening at a proximal end that can core and separate a portion of the vascular thrombus from the blood vessel. In some embodiments, the proximal end of the fenestrated structure is coupled to a distal end of the first intermediate shaft. The thrombus extraction device can include an expandable cylindrical portion formed of a braided filament mesh structure having an everted portion. In some embodiments, the braided filament mesh structure can capture the vascular thrombus portion. In some embodiments, a proximal end of the mesh structure is coupled to a distal end of the fenestrated structure, and the everted portion of the mesh structure extends proximally through the opening of the unitary fenestrated structure. In some embodiments, a length of the everted portion relative to the non-everted portion of the braided filament mesh structure varies based on a position of the first intermediate shaft relative to the inner shaft of the catheter.

In some embodiments, the net-like filament mesh structure is integrally formed on the unitary fenestrated structure. In some embodiments, the net-like filament mesh structure everts on the unitary fenestrated structure. In some embodiments, the braided filament mesh structure includes a non-everted portion coupled to the distal end of the fenestrated structure. In some embodiments, the distal end of the braided mesh is coupled to the inner shaft. In some embodiments, the distal end of the braided mesh is fixedly coupled to the inner shaft. In some embodiments, the distal end of the braided mesh is slidably coupled to the inner shaft.

In some embodiments, the thrombus extraction device can include an expansion mechanism that can maintain a desired radial force on a vessel wall with the unitary fenestrated structure. In some embodiments, the expansion mechanism can hold the unitary fenestrated structure in full expansion. In some embodiments, the expansion mechanism includes a ring feature of the unitary fenestrated structure and a stop feature that can engage with the ring feature when the unitary fenestrated structure is in full expansion. In some embodiments, the stop feature can be a tab on a second intermediate shaft. In some embodiments, the tab can engage with the ring feature, and the second intermediate shaft can be coaxial with the first lumen. In some embodiments, the stop feature can be a tension spring dynamically coupled with the ring feature.

In some embodiments, the net-like filament mesh structure everts on itself. In some embodiments, the thrombus extraction device can include an eversion stop that can limit proximal movement of the inner shaft with respect to the unitary fenestrated structure to prevent full eversion of the net-like filament mesh structure. In some embodiments, the net-like filament mesh structure can include a plurality of filaments and can have a first pore size at a proximal portion and a second pore size at a distal portion. In some embodiments, the first pore size is different from the second pore size. In some embodiments, the at least some of the plurality of filaments are longitudinally overlaid in the distal portion. In some embodiments, the self-expanding coring element and the expandable cylindrical portion are contained within the outer shaft of the catheter such that the everted portion of the mesh structure extends proximally through the opening of the unitary fenestrated structure.

One aspect of the present disclosure relates to a method for removal of thrombus from a blood vessel in a body of a patient. The method includes advancing a catheter constraining the thrombus extraction device through a vascular thrombus. In some embodiments, the thrombus extraction device includes a proximal self-expanding member formed of a fenestrated structure, and a substantially cylindrical portion formed of a net-like filament mesh structure having a proximal end coupled to a distal end of the fenestrated structure. The method includes: deploying the thrombus extraction device by distally advancing the self-expanding member with respect to the catheter until the self-expanding member is beyond a distal end of the catheter; retracting the self-expanding member relative to the distal end of the net-like filament mesh structure to increase a distal length of the net-like filament mesh structure and to separate a portion of the thrombus from the vessel wall and to capture the portion of the thrombus within the net-like filament mesh structure; and withdrawing the thrombus extraction device from the body to remove thrombus from the patient.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

FIG. 15 is a side view of one embodiment of an obturator having a constant dimension of an elongate shaft.

FIG. 16 is a side view of one embodiment of an obturator having a variable dimension of an elongate shaft.

FIG. 17 is a detailed section view of one embodiment of the capture sheath of the obturator.

FIG. 18 is a side view of one embodiment of an introducer sheath in an undeployed configuration.

FIG. 19 is a side view of one embodiment of an introducer sheath in a partially deployed configuration.

FIG. 20 is a side view of one embodiment of an introducer sheath in a deployed configuration.

FIGS. 23-A through 23-H are views depicting one embodiment of a process for fully expanding the thrombus extraction device in a blood vessel.

FIGS. 24-A and 24-B are views depicting alternative steps in the process for fully expanding the thrombus extraction device in a blood vessel.

FIGS. 25-A through 25-H are views depicting one embodiment of a process for removal of thrombus with an expanded thrombus extraction device.

FIGS. 34-A to 34-D are views depicting one embodiment of a process for affecting the relative lengths of the everted portion and the non-everted portion of a thrombus extraction device in a blood vessel.

FIG. 35 is a schematic illustration of one embodiment of a funnel catheter.

FIG. 36 is schematic illustration of one embodiment of a dilator assembly with a moveable sheath in a loading position.

FIG. 37 is schematic illustration of one embodiment of a dilator assembly with a moveable sheath in a retracting position.

FIGS. 38-A to 38-D are views depicting one embodiment of steps in a process for deploying the self-expanding funnel of a funnel catheter.

FIG. 40 is a section view of one embodiment of a handle and a shuttle of the thrombectomy system.

FIGS. 41-A to 41-F are views depicting one embodiment of steps in a process for expanding a stackable thrombus extraction device in a blood vessel.

FIGS. 42-A and 42-B are views depicting one embodiment of steps in a process for retracting stackable thrombus extraction device through thrombus in a blood vessel.

DETAILED DESCRIPTION OF THE INVENTION

Figure 1:
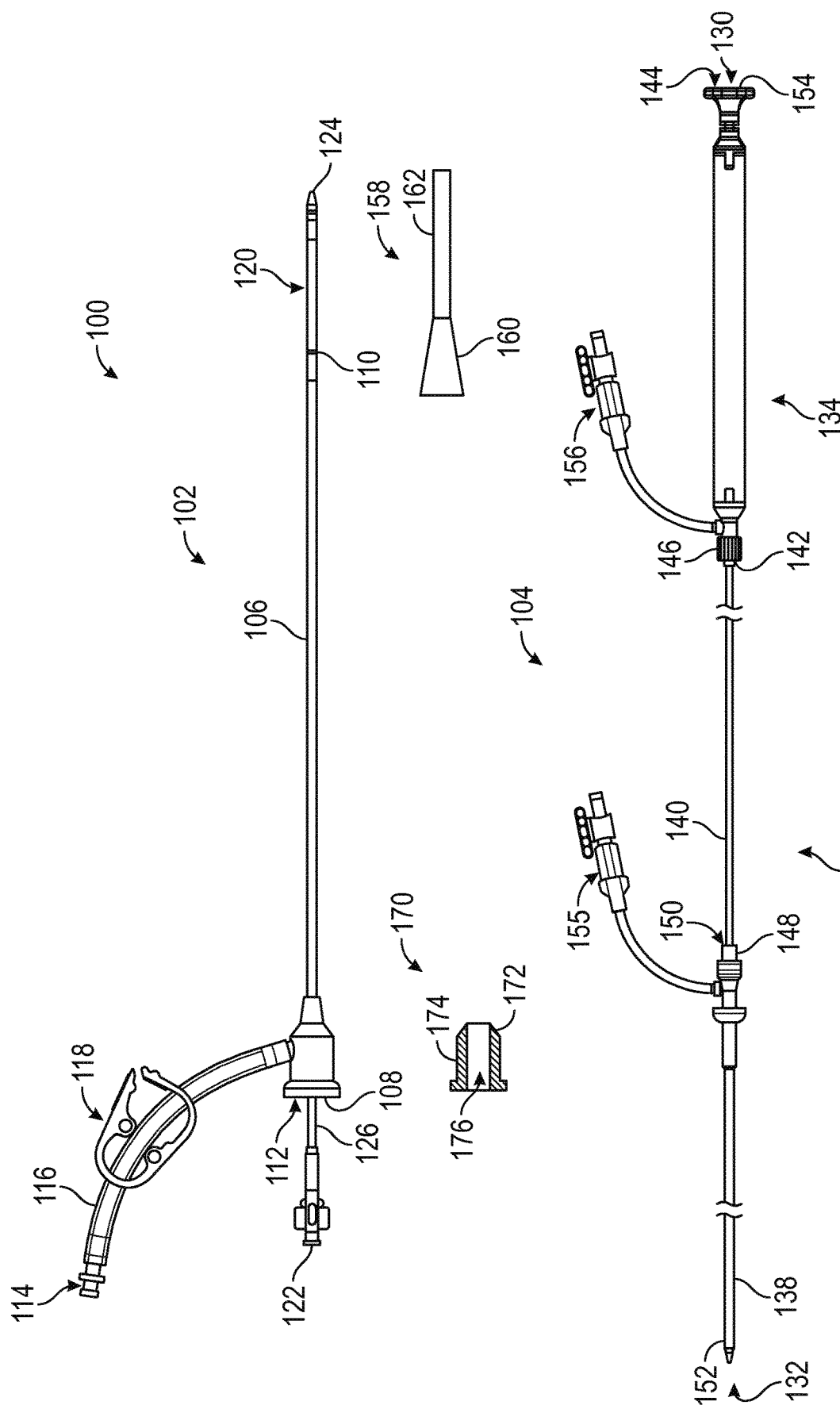
FIG. 1 is a perspective view of one embodiment of a thrombectomy system for removal of a thrombus from a blood vessel of a patient.

The present disclosure relates to a thrombectomy system for removal of a vascular thrombus from a blood vessel of a patient. The thrombectomy system can remove thrombus from a blood vessel, and particularly from a venous vessel of a patient via the coring of the thrombus and/or the separating of the thrombus from the walls of the blood vessel that can occur when the thrombectomy system is retracted through the vascular thrombus. Thrombus that is cored and/or separated from the walls of the blood vessel can be captured within the thrombectomy system and removed from the patient.

The thrombectomy system can include a thrombus extraction catheter including a Thrombus Extraction Device ("TED"). The TED can include a proximal self-expanding coring element that can be a stent portion and/or that can be formed of a fenestrated structure such as, for example, a unitary fenestrated structure. In some embodiments, the self-expanding coring element can be a semi-rigid structure that can be, for example, a semi-rigid collapsible structure. The TED can include a distal expandable cylindrical portion formed of a braided filament mesh structure that can, in some embodiments, include an everted portion and a non-everted portion. The braided filament mesh structure can be formed, looped, and/or interwoven on the coring element to thereby form a unitary TED, also referred to herein as an interwoven TED. This forming of the braided filament mesh structure directly on the coring element can eliminate problems, such as: inconsistent material properties, decreased flexibility, decreased strength, and/or quality control issues, arising from connecting the braided filament mesh structure to the coring element via, for example, welding or adhesive.

Thrombectomy systems including a TED having an everted portion and a non-everted portion can allow use of the thrombectomy system in blood vessels having smaller diameters than would be otherwise possible and can decrease the potential damage inflicted to valves located in the blood vessel. Specifically, such thrombus extraction devices can limit the length of the blood vessel used in deploying the TED, and particularly limit the length of the blood vessel beyond the thrombus used in deploying the thrombus extraction device allowing the TED to extract thrombus more distally located. Thus, the number of valves through which the thrombus extraction device extends can be reduced and potential valve damage can be prevented. Additionally, due to the everting nature of the TED, the device can be operated in such a way that is either in the same direction as the venous blood flow or retrograde the venous blood flow. In some embodiments, operation in the same direction as venous blood flow can further reduce the potential damage caused to the venous valves by the TED.

The expansion of the TED can be controlled by the relative movement of portions of the thrombus extraction catheter. For example, a proximal end of the TED, and specifically a proximal end of the self-expanding coring element can be connected to an intermediate shaft that is slidable within an outer shaft of the thrombus extraction catheter. A distal end of the TED, and specifically a distal end of the expandable cylindrical portion can be either fixedly or slidably connected to an inner shaft that is slidable within the intermediate shaft of the thrombus extraction catheter. As the inner shaft and the intermediate shaft are slidable with respect to the outer shaft, the TED can be withdrawn into the outer shaft to constrain the TED to an undeployed configuration, also referred to herein as a constrained configuration. Similarly, the TED can be deployed from the outer shaft by the relative movement of the intermediate shaft with respect to the outer shaft. In some embodiments, after the TED has been deployed from the outer shaft, the inner shaft and the intermediate shaft can be moved with respect to each other to either expand or contract the expandable cylindrical portion of the TED and to bring the self-expanding coring element to full expansion. In some embodiments, after the TED has been deployed from the outer shaft, the inner shaft and the intermediate shaft can be moved with respect to each other to change the length of the everted portion and the non-everted portion.

In some embodiments, self-expanding coring element can be controlled independent of the expandable cylindrical portion, and/or the expandable cylindrical portion can be controlled independent of the self-expanding coring element. In some embodiments, for example, the TED can be self-expanding coring element can be relatively distally advanced towards the expandable cylindrical portion. In such an embodiment, the expandable cylindrical portion can compress, also referred to herein as "stack" which can, in some embodiments, result in a decreased length of the expandable cylindrical portion and, in some embodiments, can result in an increased diameter of at least a portion of the expandable cylindrical portion. In some embodiments, the ability to control the self-expanding coring element independent of the expandable cylindrical portion, and the ability to stack the expandable cylindrical portion can allow the use of the thrombectomy system, and can specifically allow the capturing of large and/or lengthy thrombus without having the TED, and specifically the expandable cylindrical portion far beyond the location of the thrombus. In some embodiments, this limited extension of the expandable cylindrical portion beyond the location of the thrombus can ease the use of the thrombectomy system by limiting the extension of the thrombectomy system beyond the thrombus. In some embodiments, for example, this limitation of the extension of the thrombectomy system beyond the thrombus can mitigate risk of damage to tissues, blood vessels, and/or organs beyond the thrombus from the thrombectomy system. Specifically, such thrombus extraction devices can limit the length of the blood vessel used in deploying the TED, and particularly limit the length of the blood vessel beyond the thrombus used in deploying the thrombus extraction device. Thus, risk of damage to blood vessels, tissues, and/or organs beyond the thrombus can be minimized via stacking of the TED.

The thrombectomy system can include an introducer sheath that can be sized to slidably receive the outer sheath of the thrombus extraction catheter. In some embodiments, the introducer sheath can include a sealed aperture at a proximal end of the introducer sheath and a self-expanding funnel. In some embodiments, the introducer sheath can include a sealed aperture at a proximal end and an open distal end, and the thrombectomy system can include a funnel catheter having a self-expanding funnel. The self-expanding funnel can be located at a distal end of the introducer sheath and can be selectably held in a constrained position by a capture sheath. In some embodiments, the self-expanding funnel can be slidably contained within the introducer sheath and can specifically be slidable with respect to the distal end of the introducer sheath. In some embodiments, the self-expanding funnel can be distally slid from a constrained configuration within the introducer sheath to a deployed configuration at which the self-expanding funnel extends from the distal end of the capture sheath.

The self-expanding funnel can be sized to engage with the self-expanding coring element when the TED is retracted towards the funnel. As the TED is retracted into the funnel, the funnel compresses the TED, and specifically the coring element, and guides the TED, and specifically the coring element into a lumen defined by the introducer sheath. The TED can be retracted until it is completely contained within the introducer sheath, and then the TED and the thrombus captured in the TED can be removed from the patient via the sealed aperture. Alternatively, in some embodiments, the TED can be retracted until all or a portion of the coring element is contained within the funnel attached to the funnel catheter, and the funnel catheter and the TED can then be simultaneously retracted, in some embodiments, through the introducer sheath.

The thrombectomy system can access the blood vessel containing the thrombus via a plurality of access sites. These can include, for example, an internal jugular (IJ) access site, a femoral access site, a popliteal access site, or other venous or arterial access sites. The thrombectomy system can be used to extract thrombus and/or embolus from a variety of venous and/or arterial vessels, which can be peripheral vessels, including any vessel, including, by way of non-limiting example, a venous vessel, having a diameter of at least 3 millimeters (mm). The thrombectomy system can be inserted through an access point into a circulatory system of a patient and can be advanced to a position proximate to the thrombus. The TED can then be advanced through the thrombus, and, after being expanded distally of the thrombus, the TED can be retracted through the thrombus, thereby capturing all or portions of the thrombus.

With reference now to FIG. 1, one embodiment of a thrombectomy system 100, also referred to herein as a thrombus extraction system 100, is shown. The thrombectomy system 100 can be used to access a portion of a blood vessel such as a venous vessel containing thrombus and the thrombectomy system 100 can be used to remove all or portions of that thrombus from the blood vessel. The thrombectomy system 100 can include an introducer sheath 102 and a thrombus extraction catheter 104.

The introducer sheath 102 comprises an elongate member 106, also referred to herein as an elongate sheath 106, having a proximal end 108 and a distal end 110. The elongate member 106 can be elastic and/or flexible. The elongate member 106 can comprise any desired length and any desired diameter. In some embodiments, the elongate sheath 106 can have an outer diameter of at least 10 French, at least 12 French, at least 14 French, at least 18 French, at least 20 French, at least 22 French, between 14 French and 24 French, between 15 French and 21 French, between 16 French and 22 French, and/or any other or intermediate size.

The elongate member 106 can comprise a radiopaque marker that can be, for example, part of the distal end 110 of the elongate member 106. The elongate member 106 defines a lumen extending between the proximal end 108 and the distal end 110. The lumen 1701 (shown in FIG. 17) of the elongate member 106 can be sized to slidably receive the thrombus extraction catheter 104. In some embodiments, the lumen 1701 of the elongate member 106 can have an internal diameter of at least 2 French, at least 10 French, at least 14 French, at least 18 French, at least 20 French, at least 22 French, between 11 French and 12 French, between 10 French and 22 French, between 14 French and 21 French, between 16 French and 20 French, and/or any other or intermediate size. The lumen 1701 can terminate at a sealed aperture 112, also referred to herein as a sealed hub 112, located at the proximal end 108 of the elongate member 106. In some embodiments, the sealed aperture 112 can be self-sealing and/or can comprise a self-sealing seal.

The introducer sheath 102 can further include an aspiration port 114 that can be at the proximal end 108 of the elongate member 106 and/or connected to the proximal end 108 of the elongate member 106 via, for example, a connecting tube 116. In some embodiments, the aspiration port 114 can be a part of, and/or connected to the sealed hub 112. In some embodiments, the aspiration port 114 can be selectively fluidly connected to the lumen 1701 via, for example, a valve 118, also referred to herein as an aspiration valve 118, which valve 118 can be a tubing clamp that can be located at a position along the connecting tube 116 between the lumen 1701 and the aspiration port 114.

The introducer sheath 102 can further hold an obturator 120, also referred to herein as a dilator 120. The obturator 120 can be configured to hold a self-expanding funnel that can be attached to the distal end 110 of the elongate member 106 in a constrained configuration, and to release the self-expanding funnel from that constrained configuration. The obturator 120 can comprise a proximal end 122, a distal end 124, and an elongate shaft 126 extending therebetween. In some embodiments, the elongate shaft 126 can have a length that is greater than a length of the elongate member 106 of the introducer sheath 102. The obturator 120 can further define a lumen extending through the obturator 120, which lumen can receive a guidewire. In some embodiments, the guidewire can comprise any desired dimensions and can, in some embodiments, have a diameter of approximately 0.035 inches. The obturator 120 can be sized and shaped so as to be able to slidably move through the lumen of the elongate member 106.

The thrombectomy system 100 can include the thrombus extraction catheter 104. The thrombus extraction catheter 104 can have a proximal end 130 and a distal end 132. A handle 134, also referred to herein as a deployment handle 134, can be located at the proximal end 130 of the thrombus extraction catheter 104 and can connect to a catheter portion 136, also referred to herein as the catheter 136.

The catheter 136 can include an outer shaft 138, an intermediate shaft 140, also referred to herein as a first intermediate shaft 140 or as a coring element shaft 140, a second intermediate shaft, also referred to herein as a stop shaft, a third intermediate shaft, and an inner shaft, also referred to herein as the tip shaft. The outer shaft 138 can comprise a variety of lengths and sizes. In some embodiments, the outer shaft 138 can be sized to slidably fit within the introducer sheath 102. In some embodiments, the outer shaft 138 can have a size of at least 8 French, at least 10 French, at least 11 French, at least 12 French, at least 14 French, at least 16 French, between 8 French and 14 French, between 11 French and 12 French, and/or any other or intermediate size.

Each of the outer shaft 138, the one or several intermediate shafts 140, 3000, 3002, and the inner shaft can define a lumen that can be a central, axial lumen. In some embodiments, the intermediate shaft 140 can be sized and/or shaped to slidably fit within the lumen 802 (shown in FIG. 8) of the outer shaft 138 such that the intermediate shaft 140 and the outer shaft 138 are coaxial. Similarly, in some embodiments, the inner shaft can be sized and/or shaped to slidably fit within the lumen 804 (shown in FIG. 8) of the intermediate shaft 140 such that the inner shaft and the intermediate shaft 140 are coaxial. In this configuration, each of the outer shaft 138, the intermediate shaft 140, and the inner shaft can be displaced relative to the others of the outer shaft 138, the intermediate shaft 140, and the inner shaft.

In some embodiments, the first intermediate shaft 140 can be sized and/or shaped to slidably fit within the lumen 802 (shown in FIG. 8) of the outer shaft 138 such that the intermediate shaft 140 and the outer shaft 138 are coaxial, the second intermediate shaft 3000, also referred to herein as the stop shaft 3000, can be sized and/or shaped to slidably fit within the first intermediate shaft 140, and/or the third intermediate shaft 3002 can sized and/or shaped to slidably fit within the second intermediate shaft 3000. Similarly, in some embodiments, the inner shaft can be sized and/or shaped to slidably fit within the second intermediate shaft 3000 or the third intermediate shaft 3002 such that the inner shaft and the intermediate shaft 140 are coaxial. In this configuration, each of the outer shaft 138, the intermediate shafts 140, 3000, 3002, and the inner shaft can be displaced relative to the others of the outer shaft 138, the intermediate shafts 140, 3000, 3002, and the inner shaft.

In some embodiments, each of the outer shaft 138, the intermediate shafts 140, 3000, 3002, and the inner shaft can have the same length, and in some embodiments some or all of the outer shaft 138, the intermediate shafts 140, 3000, 3002, and the inner shaft can have different lengths. In some embodiments, for example, one or more of the intermediate shafts 140, 3000, 3002 can be relatively longer than the outer shaft 138, and in some embodiments, the inner shaft can be relatively longer than the intermediate shaft 140.

The thrombus extraction catheter 104 can further include a thrombus extraction device (TED). In some embodiments, the TED can connect to the intermediate shaft 140 and the inner shaft, and can be contained in an undeployed configuration within the lumen 802 of the outer shaft 138, and in some embodiments, the TED can connect to the first intermediate shaft 140 and one of the second intermediate shaft 3000, the third intermediate shaft 3002, and the inner shaft. In some embodiments, the relative positioning of the outer shaft 138, one or more of the intermediate shafts 140, 3000, 3002, and/or the inner shaft can result in the TED being in an undeployed configuration, a deployed configuration, a partial expansion configuration, and/or a full expansion configuration. In some embodiments, the TED in the deployed configuration can be in either the full expansion configuration or in the partial expansion configuration.

The handle 134 can include a distal end 142, also referred to herein as a lock end 142, and a proximal end 144, also referred to herein as a plunger end 144. In some embodiments, the intermediate shaft 140 connects to, and distally extends towards the distal end 132 of the thrombus extraction catheter 104 from the distal end 142 of the handle 134. In some embodiments, in which the TED includes an everted or partially everted braided filament mesh structure, a handle is not used to deploy or actuate the braided filament mesh structure. In some such embodiments, the force of the clot against the braided filament mesh structure expands and/or deploys the braided filament mesh structure when the TED is retracted through the clot.

As seen in FIG. 1, the distal end 142 of the handle 134 can include a lock feature 146 such as, for example, a spinlock. The lock feature 146 can selectively engage and/or lockingly engage with a mating feature 148 located on a proximal end 150 of the outer sheath 138. In some embodiments, for example, the outer sheath 138 can proximally slide over the intermediate sheath 140 until the lock feature 146 engages with the mating feature 148 to thereby secure the position of the outer sheath 138 with respect to the intermediate sheath 140. In embodiments in which the intermediate shaft 146 is relatively longer than the outer shaft 138, a portion of the intermediate shaft 146 distally extends from a distal end 152 of the outer shaft 138 when the outer shaft 138 is lockingly engaged with the lock feature 146.

The handle 134 can include a plunger 154 that can be movable between a first, non-extended position and a second, extended position. In some embodiments, the plunger 154 can be moved from the first position to the second position by proximally displacing the plunger 154 relative to the handle 134. The plunger 154 can be lockable in one or both of the first position and/or the second position. In some embodiments, the plunger 154 can be connected to one or several features of the TED that can lock the TED in a full expansion configuration and/or move the TED to a full expansion configuration.

The plunger 154 can connect to one of: the second intermediate shaft 3000; the third intermediate shaft 3002; and the inner shaft such that the connected one of: the second intermediate shaft 3000; the third intermediate shaft 3002; and the inner shaft is displaceable relative to the handle 134, the outer shaft 138, and/or the intermediate shaft 140 via the movement of the plunger 154 from the first position to the second position. In some embodiments in which the inner shaft is relatively longer than the intermediate shaft 140 and/or the outer shaft 138, the inner shaft can have a length such that the inner shaft distally extends past a distal end of the intermediate shaft 140 regardless of whether the plunger 154 is in the first position or the second position.

The thrombus extraction catheter 104 can further include a first flush port 155 connecting to the outer shaft 138 and a second flush port 156 connecting to the handle 134. In some embodiments, the first flush port 155 can be fluidly connected to the lumen 802 of the outer shaft 138 so as to allow the flushing of the lumen 802 of the outer shaft 138 via the first flush port 155. In some embodiments, the second flush port 156 can be fluidly connected to an internal portion of the handle 134 and thereby the lumen of the intermediate shaft 140 so as to allow the flushing of the lumen of the intermediate shaft 140.

The thrombectomy system 100 can further include a loading funnel 158. The loading funnel 158 can include a funnel portion 160 and a shaft portion 162. The funnel portion 160 can define a funnel shaped interior volume connecting to a lumen of the shaft portion 162. The funnel shaped interior volume can be sized and shaped to receive the self-expanding funnel and to move the self-expanding funnel to a constrained position as the self-expanding funnel is advanced through the funnel portion 160. The funnel shaped interior volume and the lumen can be sized to allow the distal end 124 of the obturator 120 to pass completely through the loading funnel 158.

In some embodiments, the loading funnel 158 can be configured to facilitate loading of the self-expanding funnel into the obturator 102. In some embodiments, the self-expanding funnel can be loaded by inserting the obturator 120 through the elongate member 106 such that the obturator 120 extends from the distal end 110 of the elongate member 106 and beyond the self-expanding funnel. The loading funnel 158 can then be proximally slid over the obturator 120 and the self-expanding funnel until the self-expanding funnel is fully encapsulated by the loading funnel 158 and/or until the self-expanding funnel is in the constrained configuration. The obturator 120 can then be retracted to thereby load and/or capture the self-expanding funnel within a portion of the obturator 120, and the loading funnel 158 can then be removed from the obturator 120 and the elongate member 106.

Figure 2:
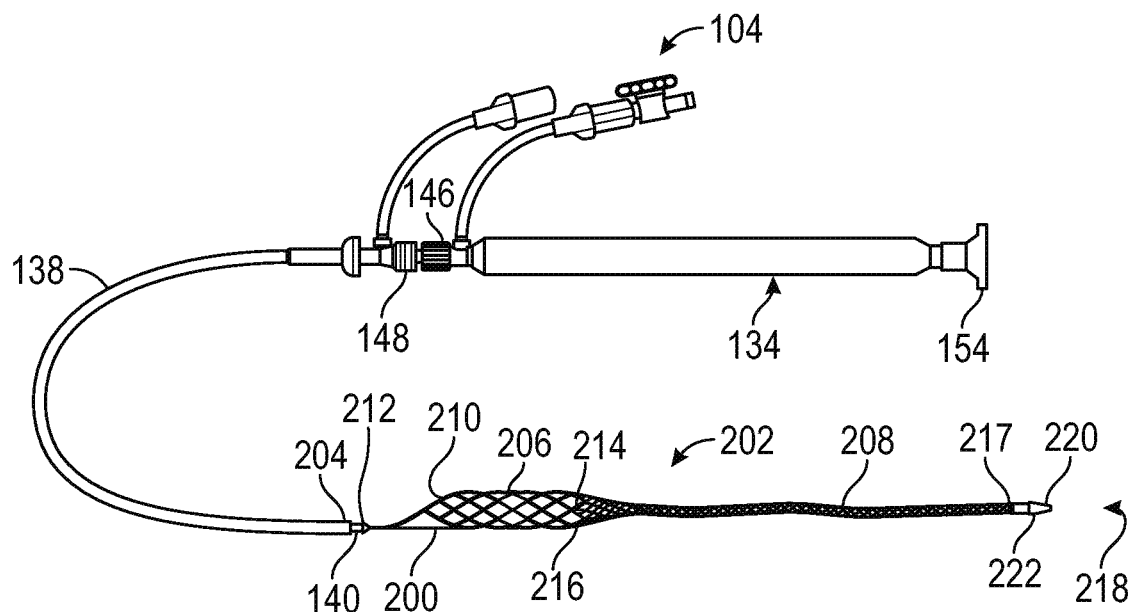
FIG. 2 is a side view of one embodiment of the thrombus extraction catheter having a thrombus extraction device is a deployed configuration.

The thrombectomy system 100 can further include a sealed hub dilator 170, also referred to herein as a seal dilator 170 and/or an aperture dilator 170. A section view of seal dilator 170 is shown in FIG. 1. The seal dilator 170 can be sized and shaped for insertion into the sealed aperture 112 prior to removal of thrombus through the sealed aperture 112. By this insertion into the sealed aperture 112, the seal dilator 170 can dilate the sealed aperture 112. In some embodiments, this dilation of the sealed aperture 112 can prevent the application of force from the sealed aperture 112 onto the thrombus during removal of the thrombus through the sealed aperture 112. In some embodiments, the seal dilator 170 can comprise an insertion portion 172 configured to facilitate the insertion of the seal dilator 170 into the sealed aperture 112. The seal dilator 170 can further comprise a body portion 174 that can, alone, or together with the insertion portion 172 define an extraction lumen 176 through which the thrombus can be removed from the lumen 1701 of the elongate member 106. In some embodiments, the internal diameter of the extraction lumen 176 can be larger than a diameter of the sealed aperture 112 in a sealed configuration With reference now to FIG. 2, a side view of one embodiment of the thrombus extraction catheter 104 is shown. The thrombus extraction catheter 104 includes the handle 134, the outer shaft 138, the intermediate shaft 140, the inner shaft 200, and the thrombus extraction device 202, also referred to herein as the TED 202. As shown in FIG. 2, the outer shaft 138 is proximally displaced relative to the handle 134 such that the mating feature 148 of the outer shaft 138 is contacting the locking feature 146 of the handle 134. Due to this positioning of the outer shaft 138 with respect to the handle 134, each of the intermediate shaft 140, the inner shaft 200, and the TED 202 distally extend beyond a distal end 204 of the outer shaft 138. The thrombus extraction device 202 shown in FIG. 2 is in a deployed and partial expansion configuration.

The thrombus extraction device 202 can include a self-expanding coring element 206, and an expandable cylindrical portion 208. The self-expanding coring element 206 can be relatively more proximally located on the thrombus extraction catheter 104 than the expandable cylindrical portion 208. The self-expanding coring element 206 can include a proximal end 210 connecting to a distal end 212 of the intermediate shaft 140 and a distal end 214 connecting to a proximal end 216 of the expandable cylindrical portion 208. The distal end 217 of the expandable cylindrical portion 208 can connect to a distal end 218 of the inner shaft 200.

In some embodiments, the distal end 218 of the inner shaft 200 can further include a tip 220 such as an atraumatic tip and/or a radiopaque marker 222. In some embodiments, the tip 220 can include the radiopaque marker 222. Further radiopaque markers can be located on, for example, the outer shaft 138 and specifically the distal end 204 of the outer shaft 138 and/or the distal end 212 of the intermediate shaft 140. In some embodiments, one or both of the distal end 204 of the outer shaft 138 and the distal end 212 of the intermediate shaft 140 can each comprise a radiopaque marker. In some embodiments, the atraumatic tip 220 can define a channel configured to allow the guidewire to pass through the atraumatic tip 220.

Figure 3:
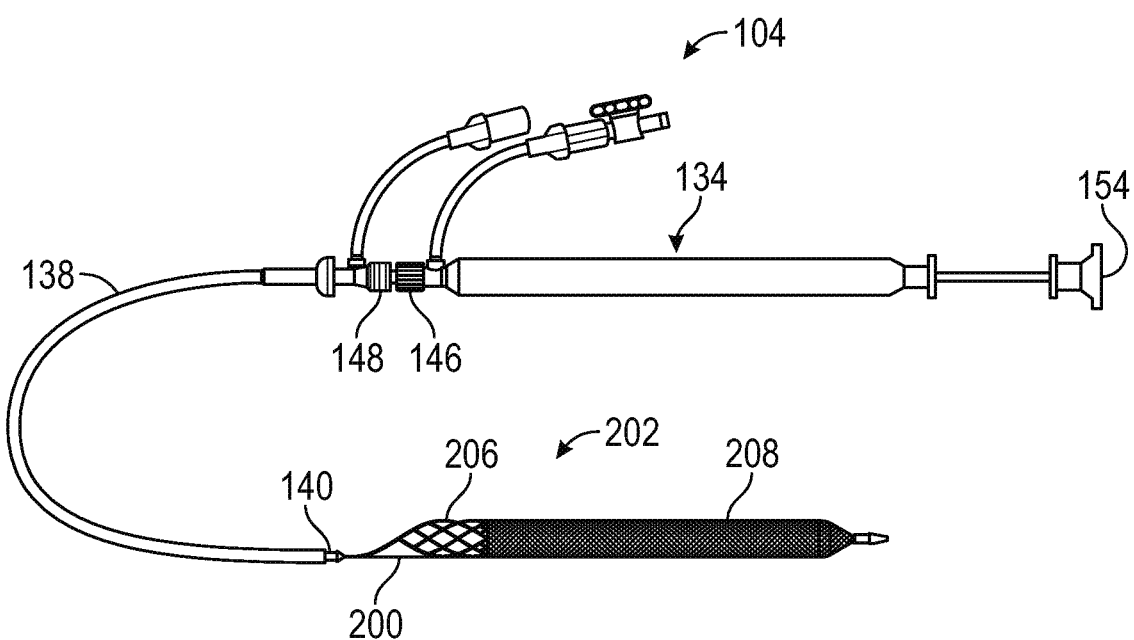
FIG. 3 is a side view of one embodiment of the thrombus extraction catheter having a thrombus extraction device is a deployed configuration at full expansion.

With reference now to FIG. 3, a side view of one embodiment of the thrombus extraction catheter 104 with the thrombus extraction device 202 in the deployed and full expansion configuration is shown. In contrast to the embodiment of FIG. 2, the plunger 154 is in the second position, proximally retracted from the handle 134, and the inner shaft 200 is thereby proximally retracted relative to the intermediate shaft 140 to thereby fully expand the expandable cylindrical portion 208 and to secure the expandable cylindrical portion 208 and the self-expanding coring element 206 in full expansion configurations and/or in full expansion.

The thrombus extraction catheter 104 can comprise one or several features configured to secure the thrombus extraction device 202, and specifically the self-expanding coring element 206 and/or the expandable cylindrical portion 208 in a fully expanded position and/or in full expansion. As used herein, full expansion describes a condition in which the thrombus extraction device 202 is in a state of continual bias to or toward expansion by one or several forces in addition to the self-expanding forces arising from the thrombus extraction device 202. In some embodiments, full expansion occurs when the thrombus extraction device 202 is deployed and when the plunger 154 is in the second position, or when the thrombus extraction device 202 is deployed and biased towards expansion via a spring connected either directly or indirectly to the thrombus extraction device 202. In such an embodiment in which the thrombus extraction device 202 is biased towards expansion via a spring, forces less than a minimal radial compressive force do not change the diameter of the thrombus extraction device 202. In some embodiments, for example, the thrombus extraction device 202 at full expansion maintains at least a desired radial force on a blood vessel when the thrombus extraction device 202 is drawn through that blood vessel. In some embodiments, one or several dimensions of the thrombus extraction device 202 can vary when the thrombus extraction device 202 is in full expansion. In some embodiments, this can facilitate apposition of the walls of the blood vessel by the thrombus extraction device 202 and/or a desired force or force level applied to the walls of the blood vessel by the thrombus extraction device 202.

In some embodiments, the plunger 154 can be locked in the second position by, for example, rotating the plunger 154 with respect to the handle 134 to thereby engage one or several locking features on the plunger 154 and in the handle 134. In some embodiments, by locking the plunger 154 in the second position, the thrombus extraction device 202, and specifically the self-expanding coring element 206 and/or the expandable cylindrical portion 208 can be secured in the full expansion by securing the position of the inner shaft 200 with respect to the intermediate shaft 140. In some embodiments, securing the position of the inner shaft 200 with respect to the intermediate shaft 140 can include locking the inner shaft 200 with respect to the intermediate shaft 140 and/or coupling the position of the inner shaft 200 with respect to the position of the intermediate shaft 140. In some embodiments, this locking and/or coupling can be static, referred to herein as statically locked and/or statically coupled, in that the position of the inner shaft 200 is fixed with respect to the position of the intermediate shaft 140, and in some embodiments, this locking and/or coupling can be dynamic, referred to herein as dynamically locked and/or dynamically coupled, in that the position of the inner shaft 200 with respect to the intermediate shaft 140 is limited. In some embodiments, and as will be discussed at greater length below, the inner shaft 200 can be dynamically locked to the plunger 154 via a compliance spring 1214, which can be, for example, a tension spring or a compression spring, which allows some movement of the inner shaft 200 with respect to the intermediate shaft 140 when the plunger is locked in the second position. Thus, in such an embodiment, the inner shaft 200 is dynamically locked and/or dynamically coupled to the intermediate shaft 140 and/or with respect to the intermediate shaft 140.

Figure 4:
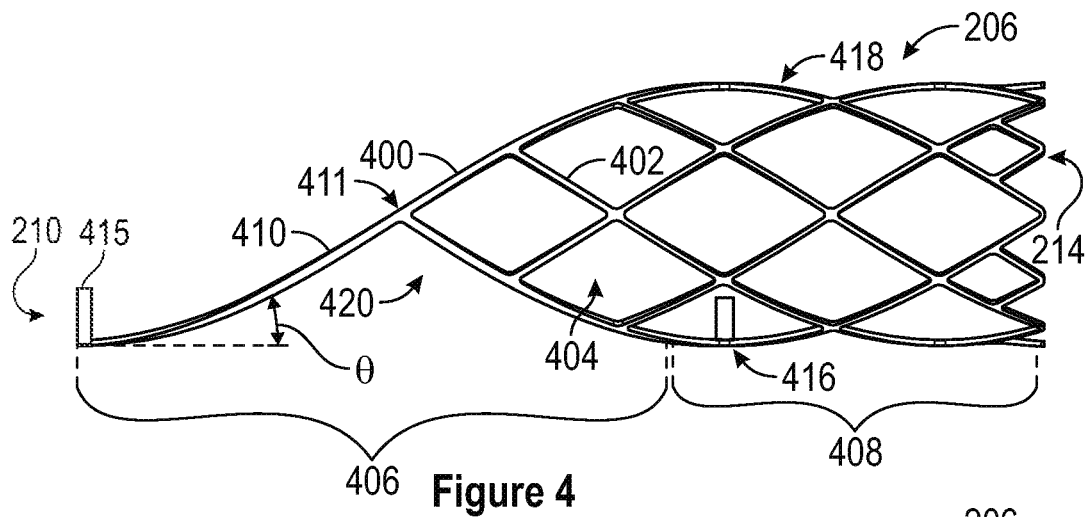
FIG. 4 is a side view of one embodiment of a self-expanding coring element.

With reference now to FIG. 4, a side view of one embodiment of the self-expanding coring element 206 is shown. The self-expanding coring element 206 can comprise a variety of shapes and sizes and can be made from a variety of materials. In some embodiments, the self-expanding coring element can be made from a shape memory material such as, for example, a shape memory alloy and/or a shape memory polymer. In some embodiments, the self-expanding coring element 206 can comprise a nitinol and/or a nitinol alloy. In some embodiments, the self-expanding coring element 206 can comprise a braid that can, for example, form a semi-rigid collapsible structure.

The self-expanding coring element 206 can be made using a variety of techniques including, for example, welding, laser welding, cutting, laser cutting, braiding, expanding, or the like. In some embodiments, the self-expanding coring element 206 can be laser cut from a piece of nitinol such as, for example, a nitinol tube, after which the self-expanding coring element 206 can be blown up and/or expanded. In some embodiment, the self-expanding coring element 206 can be laser cut nitinol, laser cut polymer tube, one or several wireform structures, metal or polymeric, or one or several injection molded polymeric structures. In some embodiments, the self-expanding coring element 206 can be castellated nitinol wire braid, nitinol braided structure, laser cut nitinol, laser cut polymer tube, injection molded polymeric structure, an inflatable balloon, or one or several other metal or polymeric structures.

The self-expanding coring element 206 can comprise a fenestrated structure 400, which can be a unitary fenestrated structure, a non-unitary fenestrated structure, and/or a stent or a stent portion that can be configured to core and separate a portion of a thrombus such as a vascular thrombus from the blood vessel containing the thrombus. This fenestrated structure 400 can comprise a plurality of struts 402 that together define a plurality of interstices 404. The struts can comprise a variety of shapes and sizes, and in some embodiments, the struts can have a thickness and/or diameter between approximately 0.05 and 0.15 inches, between approximately 0.075 and 0.125 inches, between approximately 0.09 and 0.1 inches, and/or of approximately 0.096 inches.

Figure 5:
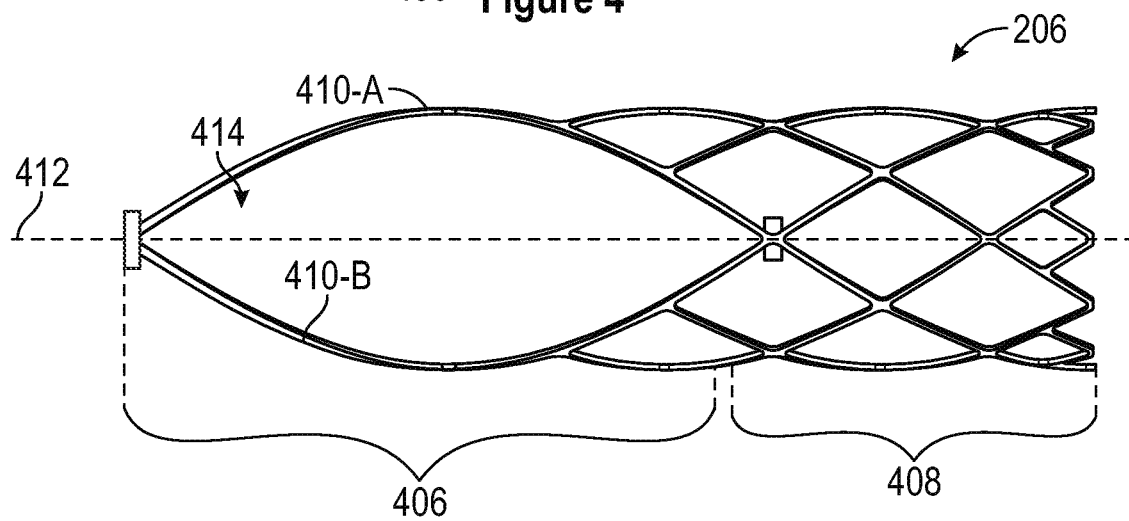
FIG. 5 is a top view of one embodiment of a self-expanding coring element.
Figure 6:
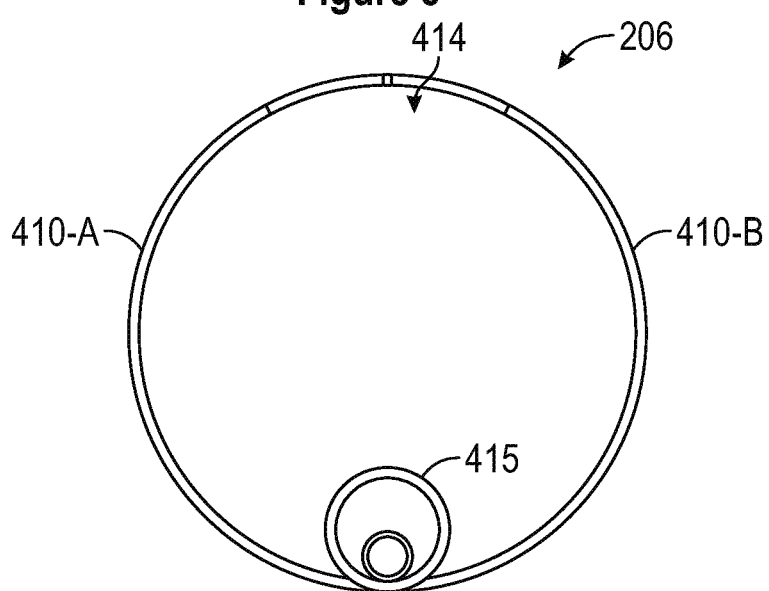
FIG. 6 is a front view of one embodiment of a self-expanding coring element.

In some embodiments, the self-expanding coring element 206 can comprise a first region 406 and a second region 408. The second region 408 can be generally tubular and can include a plurality of interconnected struts 402. The first region 406, as seen in FIG. 5, can comprise a reduced number of struts 402 as compared to the second region to facilitate the collapse of the self-expanding coring element 206 to a non-expanded configuration and to maintain a coring orientation when the blood vessel is tortuous. In some embodiments, the first region can further comprise two curved struts 410-A, 410-B twisting in opposite directions around a central axis 412, also referred to herein as a longitudinal axis 412, of the self-expanding coring element 206 to define a mouth 414 of the self-expanding coring element 206.

In some embodiments, the connection of the self-expanding coring element 206 to the intermediate shaft 140 via the two curved struts 410-A, 410-B can improve the operation of the thrombus extraction device 202 by flexibly connecting the self-expanding coring element 206 to the intermediate shaft 140. Particularly, the removal of struts from region 420 of the self-expanding coring element 206 allows the self-expanding coring element 206 to flex about a connection member 415 located at the proximal end 210 of the self-expanding coring element 206 and connecting the self-expanding coring element 206 to the intermediate shaft 140 of the thrombus extraction catheter 104. This ability to flex can facilitate the maintenance of the coring orientation with the blood vessel is tortuous. In some embodiments, such flexing of the self-expanding coring element 206 can result in the region 420 functioning as the mouth 414.

As seen in FIG. 4, the curved struts 410 extend at an angle θ, also referred to herein as a coring angle, relative to the central axis 412 from a bottom 416 of the self-expanding coring element 206 towards the top 418 of the self-expanding coring element 206. In some embodiments, this angle can be between 20 degrees and 50 degrees and/or between 30 degrees and 45 degrees when fully expanded.

In some embodiments, the coring angle can either positively or adversely affect the operation of the TED 202. For example, too steep a coring angle can prevent the self-expanding coring element 206 from being collapsible and thus prevent the retraction of the self-expanding coring element 206 into the introducer sheath 102. Additionally, too shallow a coring angle can result in the self-expanding coring element 206 too easily collapsing which can decrease the coring ability of the self-expanding coring element 206. In some embodiments, this decrease in the coring ability of the self-expanding coring element 206 can result in the self-expanding coring element 206 no longer effectively coring thrombus.

In some embodiments, the most proximal edge of the two curved struts 410-A, 410-B, referred to herein as a leading edge 411, can be sharpened and/or the leading edge 411 of the two curved struts 410-A, 410-B can comprise a cutting element, knife, or the like The self-expanding coring element 206 can comprise a variety of sizes. In some embodiments, the self-expanding coring element 206 can comprise a length, defined as the shortest distance between the proximal end 210 of the self-expanding coring element 206 and the distal end 214 of the self-expanding coring element 206, of between approximately one and 3 inches, between approximately 1.5 and 2.5 inches, between approximately 1.75 and 2.25 inches, between approximately 1.9 2.0 inches, and/or of approximately 1.96 inches. In some embodiments, the self-expanding coring element 206 can comprise a fully expanded diameter between approximately 2 and 50 mm, between approximately 4 and 25 mm, between approximately 6 and 20 mm, and/or between approximately 8 and 16 mm. In some embodiments, the self-expanding coring element can be applied to debulking of an artery or vein such as, for example, the inferior vena cava. In some embodiments, such debulking can be performed in response to the occluding and/or partial occluding of one or several filters in the inferior vena cava.

In some embodiments, the length and the diameter of the self-expanding coring element 206 can be selected based on the size of the blood vessel, and particularly the diameter of the blood vessel from which thrombus is to be extracted. In some embodiments, the length of the self-expanding coring element 206 can be selected based on the fully expanded diameter of the self-expanding coring element 206 to prevent undesired tipping and/or rotation of the self-expanding coring element within the blood vessel and with respect to the blood vessel. As used anywhere herein, "approximately" refers to a range of +/−1-10% of the value and/or range of values for which "approximately" is used.

Figure 7:
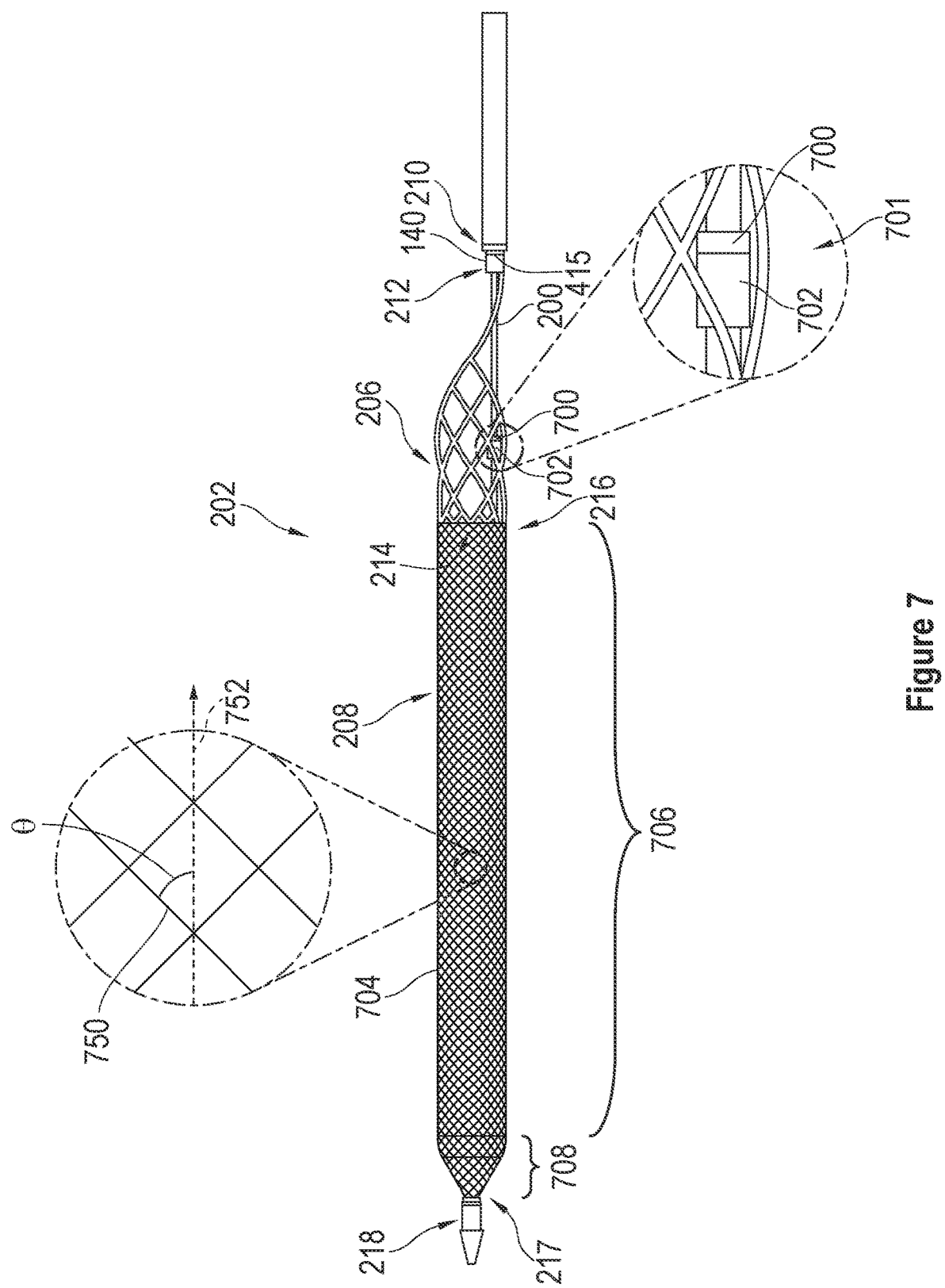
FIG. 7 is a side view of one embodiment of the thrombus extraction device in a full expansion configuration.

With reference now to FIG. 7, a side view of one embodiment of the thrombus extraction device 202 is shown. As seen in FIG. 7, the self-expanding coring element 206 is connected via the connection member 415 at the proximal end 210 of the self-expanding coring element 206 to the distal end 212 of the intermediate shaft 140. The proximal end 216 of the expandable cylindrical portion 208 connects to the distal end 214 of the self-expanding coring element 206. In some embodiments, the expandable cylindrical portion 208 and specifically the proximal end 216 of the expandable cylindrical portion 208 is formed on the distal end 214 of the self-expanding coring element 206 to thereby form a unitary thrombus extraction device 202. The distal end 217 of the expanding cylindrical portion 208 connects to the distal end 218 of the inner shaft 200.

In some embodiments, and as seen in FIG. 7, the self-expanding coring element 206 can engage with all or portions of the inner shaft 200 to affect the expansion of the self-expanding coring element 206. Specifically, in some embodiments, the self-expanding coring element 206 can include one or several features that can together form an expansion mechanism. 701. In some embodiments, the expansion mechanism 701 can include a ring 700, also referred to herein as a ring feature 700. The ring 700 can be the same material as the self-expanding coring element 206 or can be a different material than the self-expanding coring element 206. The ring 700 can be integrally formed with the self-expanding coring element 206 and/or can be attached to the self-expanding coring element via, for example, one or several welds, adhesive, one or several mechanical fasteners, or the like. The ring 700 can have a diameter larger than the diameter of the inner shaft 200 such that the ring 700 is slidable along the inner shaft 200.

As further seen in FIG. 7, the expansion mechanism 701 can include a stop 702 that can be located on one of the shafts such as, for example, one of: the second intermediate shaft 3000; the third intermediate shaft 3002; and the inner shaft 200. In some embodiments, the stop 702 can comprise a polymeric member and/or metallic member that is affixed to a portion of the inner shaft 200. The stop 702 can, in some embodiments, have the form of a tab, a protrusion, a flange, a ridge or the like. In some embodiments, the stop 702 can be sized and shaped to engage with the ring 700 to thereby apply proximally directed force to the self-expanding coring element 206 when shaft 200, 3000, 3002 to which the stop 702 is connected is proximally displaced via, for example movement of the plunger 154 to the second position and/or displacement of a shuttle moved according to a spring, such as a constant force spring connected to the shuttle. In some embodiments, a portion of the self-expanding coring element 206 located between the ring 700 and the connection member 415 can be forcibly expanded by the application of this proximally directed force to ring 700, thereby moving the self-expanding coring member 206 to full expansion. In another embodiment, the expansion mechanism 701 does not include the ring 700 and the stop 702 is not attached the one of the intermediate shafts 140, 3000, 3002, rather, the expansion mechanism 701 comprises a wire or filament that can be, for example, a metallic or polymeric material. The wire or filament wraps through the self-expanding coring element 206 and can be attached such as fixedly attached to one of the shafts such as, for example, the outer shaft 138 of the thrombus extraction catheter 104. In such an embodiment the stop 702 feature is engaged when the self-expanding coring element 206 is fully deployed by the wire or filament creating tension on the self-expanding coring element 206. In some embodiments, for example, the terminating end of the filament can be fixed to one of the shafts such as, for example, the outer shaft 138 of the thrombus extraction catheter 104 via a compression or tension spring, which spring allows the self-expanding coring element 206 to reduce in diameter slightly without disengaging the stop 702. In some embodiments, the wire or filament is comprised of an elastic material to include the functionality of the compression or tension spring.

In some embodiments, the inner shaft 200 of the thrombus extraction catheter 104 can be selectively connected to the distal end 217 of the expandable cylindrical portion 208. This can allow the displacement of the inner shaft 200 to bring the self-expanding coring element 206 to full expansion via the engagement of the ring feature 700 with the stop 702. In some embodiments, and after the self-expanding coring element 206 is at full expansion, the inner shaft 200 can be recoupled to the distal end 217 of the expandable cylindrical portion 208 such that the expandable cylindrical portion 208 is fully expanded and/or can be recoupled to the distal end 217 of the expandable cylindrical portion 208 to compress the expandable cylindrical portion 208 when the plunger 154 is moved from the second position to the first position.

In some embodiments, the expandable cylindrical portion 208 can comprise a braided filament mesh structure 704 that can be configured to capture thrombus. In some embodiments, the braided filament mesh structure can be coextensive with the expandable cylindrical portion 208 and thus can share a proximal end 216 and/or a distal end 217. In the embodiment shown in FIG. 7, the braided filament mesh structure 704 is a braid of elastic filaments having a generally tubular, elongated portion 706 and a distal tapered portion 708. In other embodiments, the braided filament mesh structure 704 can be any porous structure and/or can have other suitable shapes, sizes, and configurations (e.g., the distal portion 708 can be generally cylindrical, etc.).

Due to the connection of the braided filament mesh structure 704 to the distal end 218 of the inner shaft 200, axial movement of the inner shaft 200 radially expands/shortens or collapses/lengthens the braided filament mesh structure 704 of the TED 200. For example, so long as the intermediate shaft 140 is fixed and/or limited to axial movement at a rate less than that of the inner shaft 200: (1) distal movement of the inner shaft 200 stretches the braided filament mesh structure 704 along its longitudinal axis such that the radius of the braided filament mesh structure 704 decreases and the length of the braided filament mesh structure 704 increases; and (2) proximal movement of the inner shaft 200 compresses the braided filament mesh structure 704 along its longitudinal axis such that the radius of the braided filament mesh structure 704 increases and the length of the braided filament mesh structure 704 decreases. The filament mesh structure 704 can be positioned in a plurality of configurations including, for example, a stacked configuration, a collapsed configuration, and an expanded configuration. The filament mesh structure 704 in the stacked configuration can have a shorter length than the filament mesh structure 704 in the expanded configuration, and the filament mesh structure 704 in the expanded configuration can have a shorter length the filament mesh structure 704 in the collapsed configuration. In certain embodiments, the braided filament mesh structure 704 can have any desired length in the collapsed configuration, including, for example, a length in the collapsed configuration between approximately 1 and 80 inches, between 2 and 60 inches, between 3 and 50 inches, between approximately 5 and 30 inches, between approximately 10 and 20 inches, and/or of approximately 16 inches, and in some embodiments, the braided filament mesh structure 704 can have a length in the expanded configuration of between approximately 1 and 25 inches, between approximately 10 and 20 inches, and/or of approximately 11 inches. In some embodiments, the filament mesh structure 704 can have any desired length in the stacked configuration including, for example, a length between 1 and 50 inches, a length between 1 and 30 inches, a length between 1 and 20 inches, a length of between 1 and 15 inches, between 2 and 10 inches, and/or of approximately 5 inches in the stacked configuration.

In some embodiments, the braid angles of the filament mesh structure 704 can change between configurations. In some embodiments, for example, the filament mesh structure 704 can be defined by a braid angle $\theta$ as shown in FIG. 7. The braid angle $\theta$ can be the angle between the wire/filament 750 of the braid and the center line 752 of the braid. As the length of the filament mesh structure 704 increases, the braid angle $\theta$ can decrease, and as the length of the filament mesh structure 704 decreases, the braid angle $\theta$ can increase. In some embodiments, the braid angle $\theta$ of the filament mesh structure 704 can be less than approximately 10°, less than approximate 20°, less than approximately 30°, less than approximately 40°, and/or less than approximately 50° when the filament mesh structure 704 is in the collapsed configuration. In some embodiments, the braid angle of the filament mesh structure 704 can be between 20° and 85°, between 30° and 70°, between 35° and 60°, between 40° and 50°, and/or approximately 45° when the filament mesh structure 704 is in the expanded configuration. In some embodiments, the braid angle of the filament mesh structure 704 can be greater than approximately 45°, greater than approximately 60°, greater than approximately 70°, and/or greater than approximately 80° when the filament mesh structure 704 is in the stacked configuration.

In some embodiments, the braided filament mesh structure 704 can be formed by a braiding machine and/or weaving machine, and in some embodiments, the braided filament mesh structure 704 can be manually braided and/or woven. It can be advantageous to utilize a braiding machine and/or weaving machine that does not employ bobbins or other filament spooling mechanisms, typical of many conventional braiders as they make forming the braid onto the self-expanding coring element 206 significantly more difficult. Braiding machine and/or weaving machine where the filaments are free-hanging allow for much easier loading directly onto the self-expanding coring element 206. In some embodiments, the braided filament mesh structure 704 can be braided using methods or devices contained in some or all of: U.S. Pat. No. 8,833,224, entitled "BRAIDING MECHANISM AND METHOD OF USE", and filed on May 8, 2013; U.S. Pat. No. 8,826,791, entitled "BRAIDING MECHANISM AND METHOD OF USE", and filed on Sep. 10, 2012; U.S. Pat. No. 8,261,648, entitled "BRAIDING MECHANISM AND METHOD OF USE", and filed on Oct. 17, 2011; U.S. Pat. No. 8,820,207, entitled "BRAIDING MECHANISM AND METHOD OF USE", and filed on Apr. 26, 2013; U.S. Patent Publication No. 2016/0030155, entitled "ANEURYSM GRAFT WITH STABILIZATION", and entering the U.S. National Phase on Sep. 14, 2015; and U.S. Patent Publication No. 2014/0318354, entitled "BRAIDING MECHANISM AND METHOD OF USE", and filed on Jul. 11, 2014; the entirety of each of which is hereby incorporated by reference herein.

In some embodiments, the braided filament mesh structure 704 may be formed as a tubular braid, which tubular braid may then be further shaped using a heat setting process. In some embodiments, the braid may be a tubular braid of fine metal wires such as nitinol (nickel-titanium alloy), platinum, cobalt-chrome alloy, stainless steel, tungsten or titanium. In some embodiments, the braided filament mesh structure 704 can be formed at least in part from a cylindrical braid of elastic filaments. Thus, the braid may be radially constrained without plastic deformation and will self-expand on release of the radial constraint. Such a braid of elastic filaments is herein referred to as a "self-expanding braid."

In some embodiments, the thickness of the braid filaments can be less that about 0.15 mm. In some embodiments, the braid may be fabricated from filaments and/or wires with diameters ranging from about 0.05 mm to about 0.25 mm. In some embodiments, braid filaments of different diameters may be combined to impart different characteristics including: stiffness, elasticity, structure, radial force, pore size, embolic capturing or filtering ability, etc. In some embodiments, the braided filament count is between 20 and 80, is greater than 30, and/or is approximately 24. Pore sizes of the braided mesh in the elongated portion 706 may be in the range of about 0.4 mm to 4.0 mm. In some embodiments, the pore size may be in the range of 0.5 mm to 2.5 mm.

Figure 8:
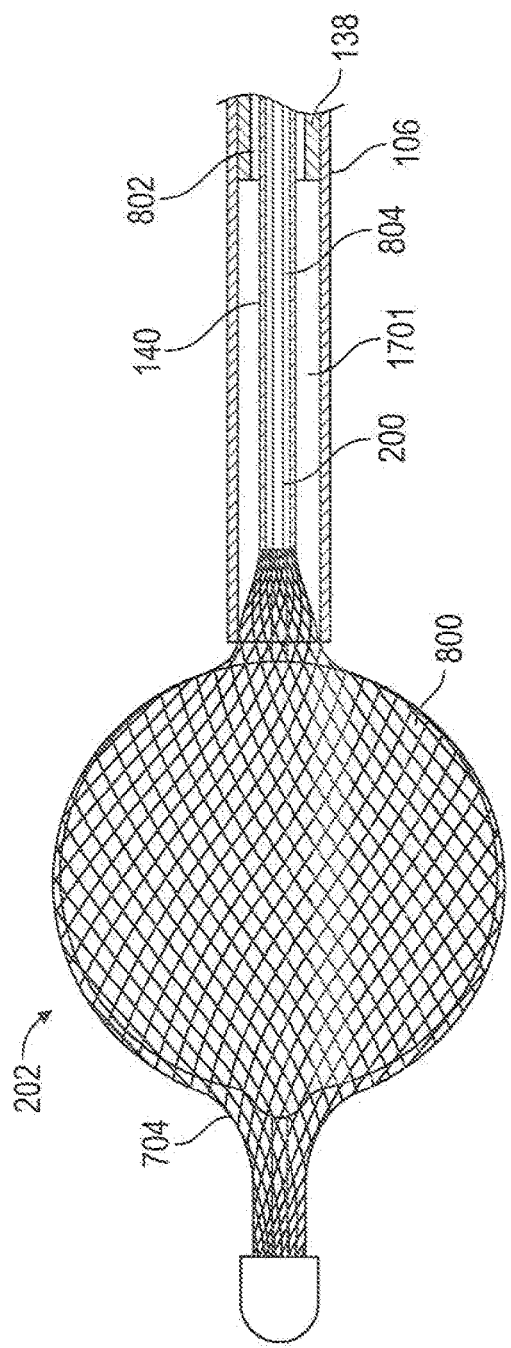
FIG. 8 is a view of one embodiment of a ball shaped thrombus captured in a thrombus extraction device.
Figure 9:
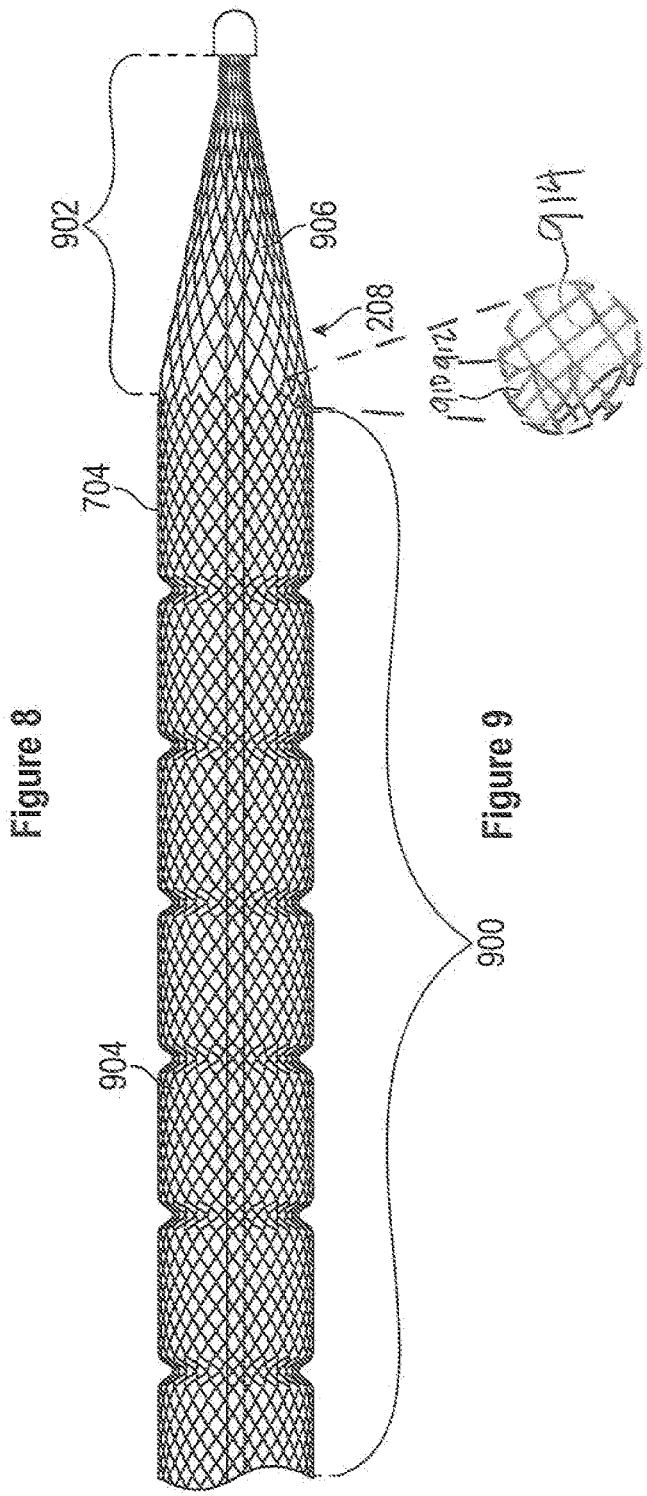
FIG. 9 is a side view of one embodiment of the braided filament mesh structure having multiple pore sizes.
Figure 10:
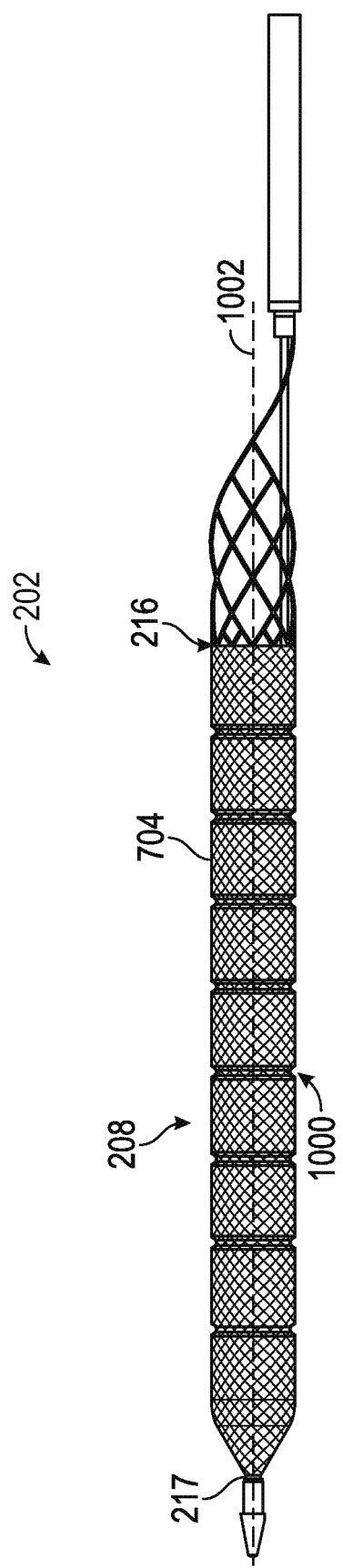
FIG. 10 is a side view of one embodiment of the thrombus extraction device including a plurality of circumferential grooves.

In some cases thrombus may form a shape that is difficult to retract into the introducer sheath 102 when thrombus is within the braided filament mesh structure 704. Such a case is depicted in FIG. 8 in which the thrombus extraction device 202, and specifically the braided filament mesh structure 704, is partially retracted into the introducer sheath 102. As depicted in FIG. 8, thrombus 800 has formed a ball that has a diameter larger than the diameter of the introducer sheath 102. Such behavior by the thrombus 800 can prevent the removal of the TED 200 and the thrombus 800 from the patient's body. FIGS. 9 and 10 address features to prevent such behavior by the thrombus.

FIG. 8 further shows a cross-section view of the elongate member 106 such that the lumen 1702 of the elongate member is visible, a cross-section of the outer shaft 138 such that the lumen 802 of the outer shaft 138 is visible, and a cross-section of the intermediate shaft 140 such that the lumen 804 of the intermediate shaft 140 is visible.

With reference now to FIG. 9, a side view of one embodiment of the braided filament mesh structure 704 comprising multiple pore sizes is shown. As seen, the braided filament mesh structure 704 comprises a first portion 900 comprising a first plurality of pores 904 and a second portion 902 comprising a second plurality of pores 906. In some embodiments, the first portion 900 can correspond to the elongated portion 706, and the second portion 902 can correspond to the distal tapered portion 708.

As shown in FIG. 9, the first portion 900 of the braided filament mesh structure 704 is relatively more proximal than the second portion 902. As further shown, the pores in the first plurality of pores 904 of the first portion 900 are smaller than the pores in the second plurality of pores 906 of the second portion 902. In some embodiments, the larger pores of the distal, second portion 902 can have an average size greater than or equal to 1.5 mm, and in some embodiments, between approximately 1.0 mm and 4.0 mm.

In such an embodiment, the larger size of the pores of the second plurality of pores 906 can allow and/or facilitate the extrusion of portions of the thrombus when the braided filament mesh structure 704 is moved to the unexpanded configuration and/or when the braided filament mesh structure 704 is retracted into the introducer sheath 102. In some embodiments, this extrusion of portions of the thrombus can prevent the case in which the thrombus cannot be retracted into the introducer sheath 102. Further, in some embodiments, relatively newer portions of thrombus can be extruded before relatively older portions of thrombus as relatively newer portions of thrombus can be softer and/or more malleable. These relatively newer portions of the thrombus can then be captured and/or broken down by features of the introducer sheath 102.

In some embodiments, and as seen in FIG. 9, the braided filament mesh structure 704 can transition from the first portion 900 to the second portion 902 by the longitudinal overlaying of one or several first wires 910 or first filaments 910 with one or several second wires 912 or second filaments 912. In some embodiments, for example, a first wire 910 can be longitudinally overlaid with a second wire 912 thereby forming a wire pair 914. In some embodiments, the first and second wires 910, 912 forming the wire pair 914 can then be woven as a single wire to thereby increase the pore size in portions of the braided filament mesh structure 704 woven with the wire pair 914. In some embodiments, for example, the first portion 900 can comprise a 48 wire mesh. In the second portion 902, one-half of the wires or filaments forming the 48-wire mesh can be first wires 910 and the other half of the wires or filaments forming the 48-wire mesh can be second wires 912. Each of the first wires 910 can be longitudinally overlaid by one of the second wires 912, thereby forming 24 wire pairs 914. These wire pairs 914 can then be woven to form a 24-wire mesh having a larger pore size than the 48-wire mesh.

With reference now to FIG. 10, a side view of one embodiment of the TED 200 comprising a plurality of circumferential depressions 1000, also referred to herein as circumferential grooves, radial ribs, and/or radial grooves, is shown. In some embodiments, some or all of this plurality of circumferential depressions 1000 can inwardly extend towards a central axis 1002 and/or midline 1002 of the thrombus extraction device 202. In some embodiments, the plurality of circumferential depressions 1000 can be longitudinally spaced and/or equally spaced along the length of the expandable cylindrical portion 208 and/or the braided filament mesh structure 704 between the proximal end 216 and the distal end 217 of the cylindrical portion 208 and/or the braided filament mesh structure 704. In some embodiments, these circumferential depressions 1000 can, when the thrombus extraction device 202 is moved from an expanded configuration to an unexpanded configuration, engage with portions of the thrombus contained within the cylindrical portion 208 and/or the braided filament mesh structure 704 to inhibit movement of the thrombus with respect to one or both of the proximal end 216 and the distal end 217 of the cylindrical portion 208 and/or the braided filament mesh structure 704. This inhibition of thrombus movement can decrease the likelihood of the creation of thrombus that cannot be retracted into the introducer sheath 102.

Although depicted in separate figures, some embodiments of the thrombus extraction device 202 can include both the plurality of circumferential depressions discussed with respect to FIG. 10 and multiple pore sizes as discussed with respect to FIG. 9.

Figure 11:
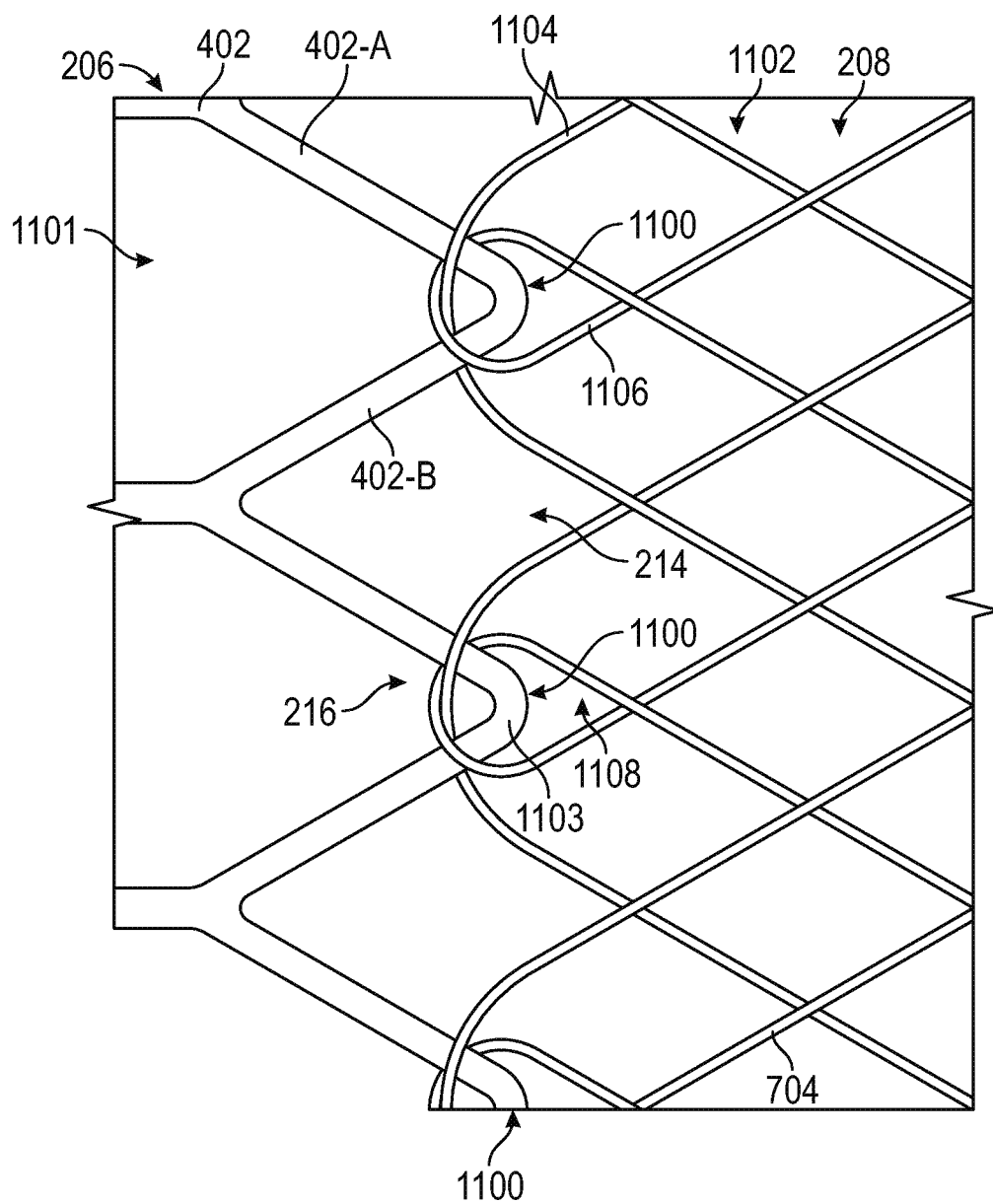
FIG. 11 is a schematic illustration of one embodiment of a braiding and/or weaving pattern for forming the cylindrical portion and/or the braided filament mesh structure onto the self-expanding coring element.

With reference now to FIG. 11, a schematic illustration of one embodiment of a weaving pattern for forming the cylindrical portion 208 and/or the braided filament mesh structure 704 onto the self-expanding coring element 206 at one or several formation points 1103 is shown. As seen, the self-expanding coring element 206 comprises a plurality of struts 402 that connect at formation points 1103 comprising peaks 1100, also referred to herein as peak struts 1100. As seen, each of the peaks 1100 is formed by the intersection of a first strut 402-A and a second strut 402-B, which intersecting struts 402-A, 402-B form a peak aperture 1101.

In some embodiments, the self-expanding coring element 206 can comprise a plurality of peaks 1100 extending around the distal end of the self-expanding coring element 206. The plurality of peaks 1100 can comprise 4 peaks 1100, 6 peaks 1100, 8 peaks 1100, 10 peaks 1100, 12 peaks 1100, 16 peaks 1100, 20 peaks 1100, 24 peaks 1100, between 4 and 50 peaks, between 8 and 20 peaks, and/or any other or intermediate number of peaks.

The cylindrical portion 208 and/or the braided filament mesh structure 704 can comprise a plurality of filaments 1102 woven and/or braided together to form the cylindrical portion 208 and/or the braided filament mesh structure 704. In some embodiments, the plurality of filaments can include, for each of the peaks 1100 of the self-expanding coring element 206, a first filament 1104 and the second filament 1106. The first and second filaments 1104, 1106 can be woven and/or braided onto their respective peak. In some embodiments, the first and second filaments 1104, 1106 can be woven and/or braided onto their respective peak such that one or both of the first and second filaments 1104, 1106 form a loop about their respective peak. Thus, in some embodiments, the only the first filament 1104 forms a look about its peak, only the second filament 1106 forms a loop about its peak, or both the first and second filaments 1104, 1106 form loops about their peak. With reference to the embodiment of FIG. 11, the first filament 1104 can be inserted straight through the peak aperture 1101 of its peak such that the first filament 1104 does not loop on itself directly adjacent to its peak, and more specifically, directly distal of its peak.

The first filament 1104 can be inserted through the peak aperture 1101 of its peak 1100 such that the first filament 1104 passes, when looking from the outside of the self-expanding coring element 206 towards the inside of the self-expanding coring element 206, on top of the first strut 402-A and under the second strut 402-B.

The second filament 1106 can be inserted through the peak aperture 1101 of its peak such that the portion of the second filament 1106 passing through the peak aperture 1101 is separated from the peak by the first filament 1104. Further, the second filament 1106 can be inserted through the peak aperture 1101 such that the second filament 1106 passes underneath the first strut 402-A and over the second strut 402-B. after insertion through the peak aperture 1101, the second filament 1106 can be looped on itself to form a loop 1108 directly distal to its peak 100.

In some embodiments, because each filament 1104, 1106 is inserted through a peak aperture 1101, each filament 1104, 1106 can be treated, for braiding or weaving purposes as comprising a first wire extending from its peak 1100 to a first end of the filament 1104, 1106 and a second wire extending from its peak to a second end of that filament 1104, 1106. Thus, in some embodiments in which the self-expanding coring portion 206 comprises 12 peaks, the cylindrical portion 208 and/or the braided filament mesh structure 704 can be formed from 24 filaments 1104, 1106 which can be woven and/or braided as 48 wires to form a 48 wire mesh and/or weave.

In some embodiments, the cylindrical portion 208 and/or the braided filament mesh structure 704 can be braided/woven by, identifying the plurality of formation points 1103 formed by some of the struts 402 of the self-expanding coring element 206. Unique pairs of wires can be threaded through each of the formation points 1103, and specifically through the peak aperture 1101 adjacent to each of the formation points 1103. In some embodiments, each unique pair of wires can comprise a first wire 1104 and a second wire 1106 overlaying the first wire 1104. The first and second wires can then be woven and/or braided into a net-like filament mesh structure of the cylindrical portion 208 and/or the braided filament mesh structure 704 from the unique pairs of wires such that the first wires 1104 do not form loops about the formation points 1103 through which the first wires 1104 are threaded and such that the second wires 1106 form loops 1108 about the formation points 1103 through which the second wires 1106 are threaded.

Figure 12:
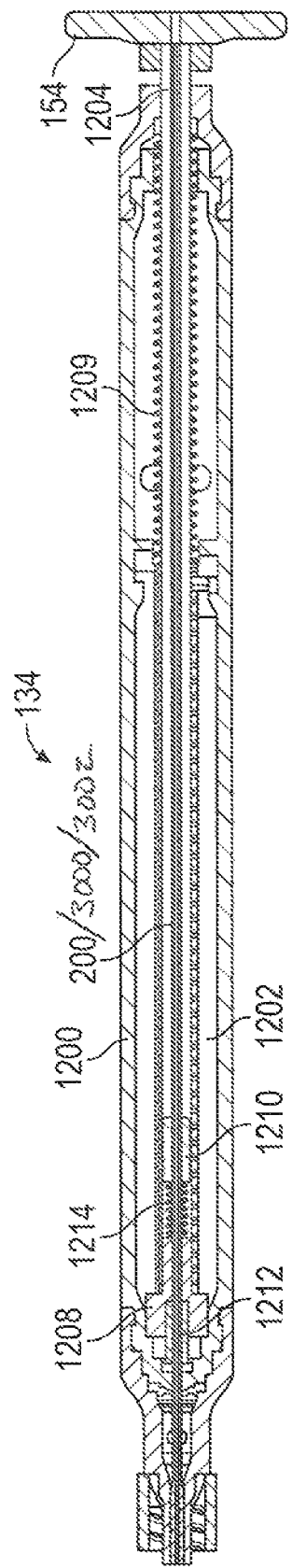
FIG. 12 is a section view of an embodiment of the handle with a plunger in a first position.
Figure 13:
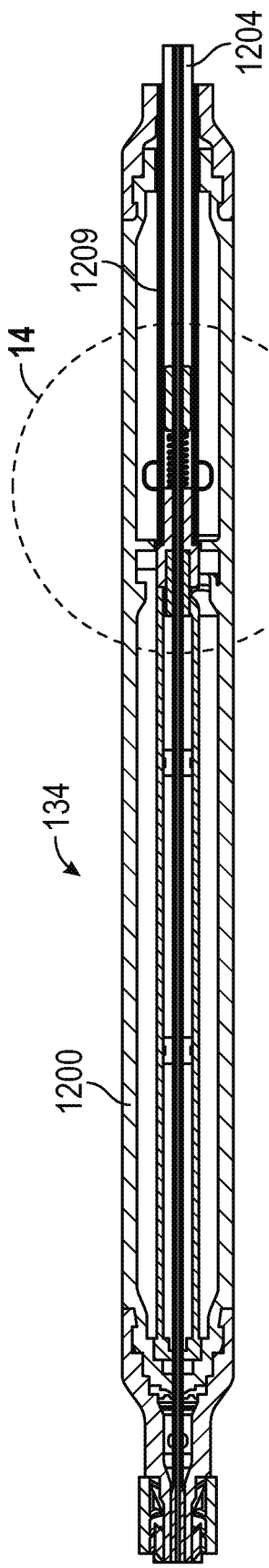
FIG. 13 is a section view of an embodiment of the handle with a plunger in a second position.

With reference now to FIG. 12, a section view of an embodiment of the handle 134 in which the plunger 154 is in the first position is shown, and with reference to FIG. 13 a section view of an embodiment of the handle 134 in which the plunger 154 is in the second position is shown. The handle 134 can include a housing 1200 that defines an internal volume 1202. A plunger shaft 1204 can extend through all or portions of the internal volume 1202 and can connect to the shaft connecting and/or coupled to some or all of the expansion features including portions of the expansion mechanism 701 such as, for example, the ring 700 or the stop 702. In some embodiments, this shaft can include, for example, the second intermediate shaft 3000, the third intermediate shaft 3002, or the inner shaft 200, which inner shaft 200 can define the previously referenced lumen 1400, also referred to herein as inner shaft lumen 1400. The plunger shaft 1204 can terminate at a plunger guide 1208 that is affixed to the plunger shaft 1204. In some embodiments, and as seen in FIGS. 12 and 13, the plunger 154 can be biased towards a first position by a plunger spring 1209 which can engage a portion of the handle 134 and the plunger guide 1208. Thus, the plunger spring 1209 is less compressed when the plunger 154 is in the first position as is shown in FIG. 12, and the plunger spring 1209 is more compressed when the plunger 154 is in the second position as is shown in FIG. 13. In some embodiments, this bias towards the first position can create a bias in the thrombus extraction device 202 towards the partial expansion configuration.

Figure 14:
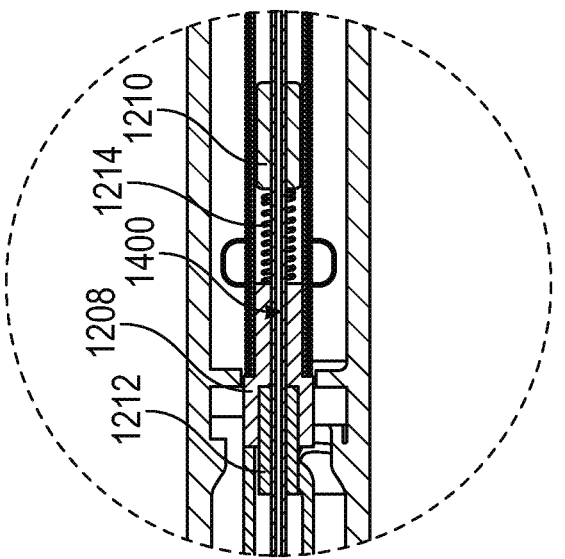
FIG. 14 is a close-up, section view of a portion of the handle with a plunger in a second position.

As seen in FIG. 14, a close-up view of the encircled portion "A" indicated in FIG. 13, the plunger guide 1208 can be positioned between a proximal stop 1210 and a distal stop 1212, which proximal stop 1210 and which distal stop 1212 can be each affixed to the shaft connecting and/or coupled to some or all of the expansion features, which shaft can include, for example, the second intermediate shaft 3000, the third intermediate shaft 3002, or the inner shaft 200 including the inner shaft lumen 1400. The plunger guide 1208 can be dynamically connected to the proximal stop 1210 via a stent compliance spring 1214, also referred to herein as a compliance spring 1214. In some embodiments, the use of the compliance spring 1214 to connect the plunger guide 1208 and the proximal stop 1210 can allow a change in the diameter of the self-expanding coring element 206 according to compressive forces applied to the self-expanding coring element 206.

In some embodiments, for example, via the interaction of the ring feature 700 and the stop 702, radial compressive forces applied to the self-expanding coring element 206 can be transferred from the self-expanding coring element 206 via the ring feature 700 and the stop 702 to the compliance spring 1214. In embodiments in which the compressive force is greater than the spring force, the compliance spring 1214 can be compressed and the shaft connecting and/or coupled to some or all of the expansion features, which shaft can include, for example, the second intermediate shaft 3000, the third intermediate shaft 3002, or inner shaft 200 can distally advance relative to the intermediate shaft 140 to thereby reduce the diameter of the self-expanding coring element 206 until the compressive force is equal to the spring force. This compliance achieved via the compliance spring 1214 enables use of the thrombus extraction catheter 104 in blood vessels that can be arteries or venous vessels of non-constant diameter while maintaining desired contact of the self-expanding coring element 206 on the walls of the blood vessels, veins, or venous vessels. In some embodiments, this compliance can result in a constant outward force applied to the vessel walls by the self-expanding coring element 206 when the vessel has a diameter between approximately 1 and 30 mm, 2 and 25 mm, 5 and 20 mm and/or any other or intermediate diameter. In some embodiments, this constant outward force can be constant in that this outward force is within a predetermined range. In some embodiments, for example, the outward force can be approximately 5 N when the diameter of the self-expanding coring element 206 is approximately 20 mm and the outward force can be approximately 20 N when the diameter of the self-expanding coring element 206 is approximately 5 mm. Thus, in some embodiments, a locking mechanism which can include the plunger 154 and the compliance spring 1214 can be configured to maintain a desired radial force on a vessel wall when the stent is compressed by that vessel wall. In some embodiments, this desired force can be a sufficient radial force on the vessel wall to core and/or separate all or portions of thrombus from the vessel wall when the self-expanding coring element 206 is at full expansion.

With reference now to FIGS. 15 and 16, side views of embodiments of the obturator 120 are shown. As seen, the obturator 120 includes the proximal end 122, the distal end 124, and the elongate shaft 126. As further seen, the obturator 120 can include a capture sheath 1500 proximally extending form the distal end 124 of the obturator 120.

The Obturator 120 can further comprise a tip such as an atraumatic tip 1502 located at the distal end 124 of the obturator 120. In some embodiments, the atraumatic tip 1502 can be radiopaque. The obturator 120 can further include a connection fitting 1504 that can be located at a proximal end 1506 of the capture sheath 1500. In some embodiments, the connection fitting 1504 can be configured to sealingly connect with the distal end 110 of the elongate sheath 106 of the introducer sheath 102.

The obturator 120 can further include a stop portion 1508 located at the proximal end 122 of the obturator 120. In some embodiments, the stop portion 1508 can have a diameter larger than the lumen 1701 of the elongate member 106 of the introducer sheath 102 and/or larger than the diameter of the sealed aperture 112 located at the proximal end 108 of the introducer sheath 102 so as to prevent the stop portion 1508 from entering into the lumen 1701 of the elongate member 106 and/or the sealed aperture 112.

In some embodiments, the elongate shaft 126 can comprise a constant size and/or diameter, and in some embodiments, the elongate shaft 126 can comprise multiple sizes and/or diameters. For example, the diameter 1510 of the elongate shaft 126 shown in FIG. 15 is constant along the length of the elongate shaft 126. In contrast, the elongate shaft 126 shown in FIG. 16 has at least a first diameter 1512 along one or several first portions 1513 of the elongate shaft 126 and a second diameter 1514 along one or several second portions 1515 of the elongate shaft 126.

In some embodiments, the one or several second portions 1515 of the elongate shaft can be located along the length of the elongate shaft 126 such, that when the obturator 120 is received within the elongate member 106 of the introducer sheath 102 and positioned so that the connection fitting 1504 seals with the distal end 110 of the elongate sheath 106, the one or several second portions 1515 extend through the sealed aperture 112. In such an embodiment, the second diameter 1514 can be selected such that the one or several second portions do not contact and/or dilate the sealed aperture 112 and/or a seal within the sealed aperture 112. Because such an embodiment of the obturator 120 does not dilate the seal of the sealed aperture 112 when the one or several second portions extend through the sealed aperture 112, the introducer sheath 102 can be stored, package, and/or sold with such an obturator 120 pre-positioned extending through the lumen 1701 of the elongate member 106.

With reference now to FIG. 17, a detailed section view of one embodiment of the capture sheath 1500 is shown. As seen, the capture sheath 1500 includes the atraumatic tip 1502 and is connected to the elongate shaft 126 of the obturator 120, which elongate shaft 126 extends through a lumen 1701 of the elongate member 106. As further seen, a lumen 1700 extends through the atraumatic tip 1502 and the elongate shaft 126, which lumen 1700 can be configured to receive a guidewire.

That capture sheath 1500 includes a capture shell 1702 that distally extends from the atraumatic tip 1502 to the proximal end 1506 of the capture sheath 1500. The capture shell 1702 terminates in the connection fitting 1504. The capture shell 1702 has an internal diameter 1704 that is greater than a diameter 1706 of the portion of the elongate shaft 126 extending through the capture shell 1702. Due to the larger internal diameter 1704 of the capture shell 1500, a receiving space is created between the capture shell 1702 and the portion of the elongate shaft 126 extending through the capture shell 1702. In some embodiments, this receiving space can be sized and shaped to receive and/or retain a self-expanding funnel 1708 in a constrained configuration. In some embodiments, the self-expanding funnel 1708 can have a diameter matching the internal diameter 1704 of the capture shell 1702 when the self-expanding funnel 1708 is in the constrained configuration. In some embodiments, this diameter of the self-expanding funnel can be less than or equal to a diameter 1716 of the elongate member 106.

The self-expanding funnel 1708 can comprise a variety of shapes and sizes and can be made from a variety of materials. In some embodiments, the self-expanding funnel 1708 can have a maximum diameter greater than and/or equal to the diameter of the self-expanded coring element 206 in full expansion, and in some embodiments, the self-expanding funnel 1708 can have a minimum diameter equal to the diameter 1716 of the elongate member 106 and/or to the diameter of the lumen 1701 of the elongate member 106. In some embodiments, the self-expanding funnel 1708 can have a length greater than and/or equal to the length of the self-expanding coring element 206 such that the self-expanding coring element 206 can be received and contained within the self-expanding funnel 1708.

In some embodiments, the self-expanding funnel 1708 can have a conically shaped portion, and specifically, a truncated-conically shaped portion. In some embodiments, the self-expanding funnel can be formed from at least one of a castellated nitinol braid, a nitinol braided stent, a laser cut nitinol, a laser cut polymer tube, an injection molded polymeric structure, or an inflatable balloon. In some embodiments, the self-expanding funnel 1708 can comprise a mesh having a pore size sufficiently small to prevent the passage of dangerous thrombus through the pores of the mesh. In some embodiments, the self-expanding funnel 1708 can be permeable to blood.

With reference now to FIGS. 18 through 20, side views of embodiments of the introducer sheath 102 in different configurations are shown. In FIG. 18 the introducer sheath 102 is shown in an undeployed configuration, in FIG. 19, the introducer sheath 102 is shown in a partially deployed configuration, and in FIG. 20, the introducer sheath 102 is shown in a fully deployed and/or deployed configuration.

Specifically, as seen in FIG. 18, the obturator 120 extends through the lumen 1701 of the elongate member 106 and the self-expanding funnel 1708 is contained in a constrained configuration within the capture sheath 1500. In FIG. 19, the obturator 120 has been distally advanced to thereby release the self-expanding funnel 1708 from the constrained configuration and/or to deploy the self-expanding funnel 1708. In some embodiments, the length of the obturator 120, and specifically the length of the elongate shaft between the proximal end of the capture sheath 1500 and the stop portion 1508 is sufficient to allow the deployment of the self-expanding funnel 1708 from the capture sheath 1500 before further distal movement of the obturator 120 is prevented by the collision of the stop portion 1508 with the sealed aperture 112.

After the self-expanding funnel 1708 has been deployed, the obturator 120 can be proximally retracted through the lumen 1701 of the elongate member 106 and the sealed aperture 112 and can be removed from the introducer sheath 102. After the obturator 120 has been removed from the introducer sheath 102, the introducer sheath is in the fully deployed configuration as shown in FIG. 20.

Figure 21:
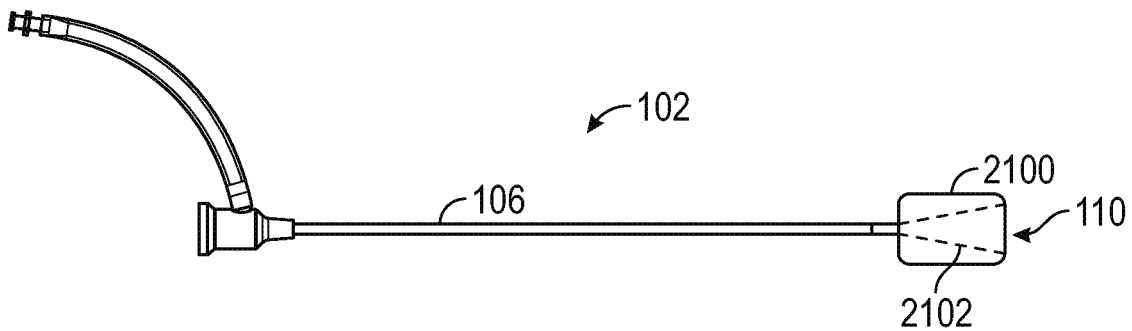
FIG. 21 is a side view of one embodiment of an introducer sheath comprising an inflatable balloon.

In some embodiments, and as seen in FIG. 21, the introducer sheath 102 can include an inflatable balloon 2100 located at, or proximate to the distal end 110 of the elongate member 106. In some embodiments, the balloon 2100 can comprise a conically shaped internal portion 2102 that can be sized and shaped to receive the thrombus extraction device 202, and specifically that can have a length greater than or equal to the length of the self-expanding coring element 206.

Figure 22:
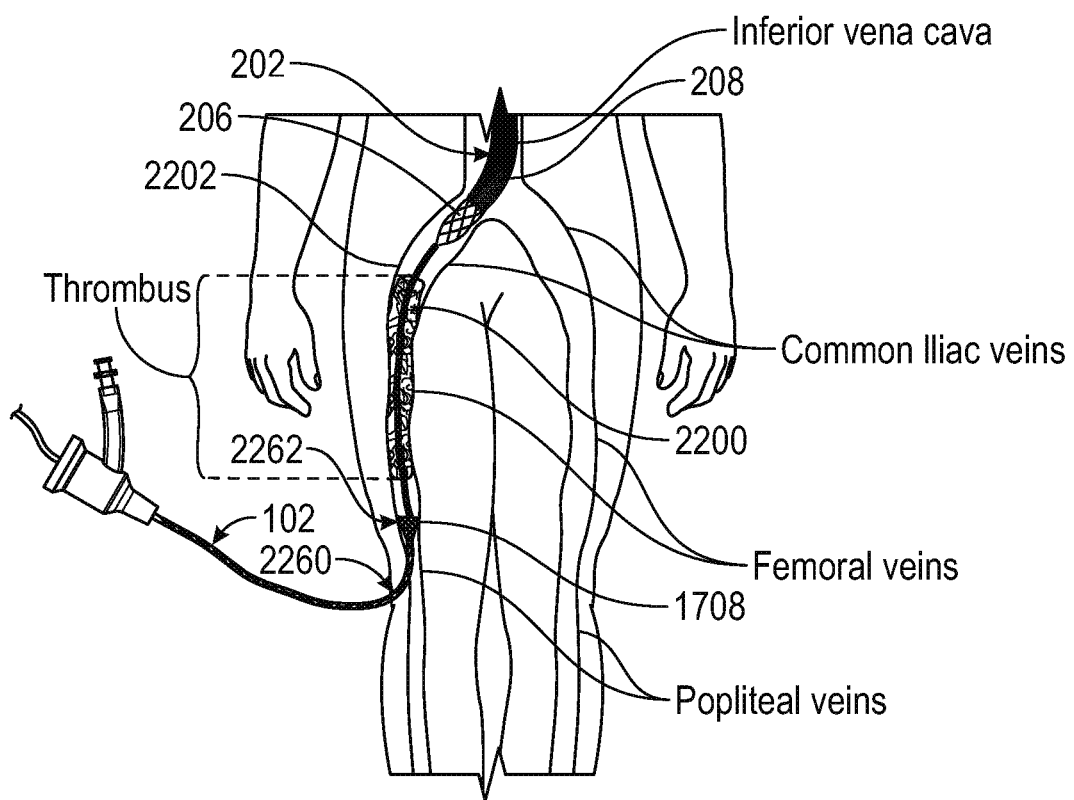
FIG. 22 is a schematic depiction of one embodiment of accessing the blood vessel via a popliteal access site.

With reference now to FIG. 22, an introduction technique for accessing the thrombus 2200 is shown. As depicted, the thrombus 2200 can be located in a blood vessel and accessed through an access site 2260 such as the popliteal access site or other venous or arterial access sites. The introducer sheath 102 can extend from the popliteal access site 2260, or other venous or arterial access sites, to the deployment position 2262 at which the self-expanding funnel 1708 can be deployed and which can be proximate to the thrombus 2200. The TED 202 can be passed through the clot 2200 in the direction of blood flow and the TED 202 can be retracted through the clot 2200 in a direction opposite blood flow. The retraction of the TED 202 through the clot 2200 can result in the coring of the clot with the self-expanding coring element 206 and the capturing of the clot in the expandable cylindrical 208.

In some such embodiments, all or portions of the TED 202 can extend into one of the iliac veins and/or the inferior vena cava as depicted in FIG. 23. Further, as the TED 202 is retracted from a proximal position with respect to the heart to a distal position with respect to the heart, the diameter of the blood vessel 2202 will decrease as the TED 202 is retracted towards the access site 2260. This can result in increased compressive forces on the TED 202, and specifically on the self-expanding coring element 206. These compressive forces can be transferred via the ring feature 700 and the stop 702 to the compliance spring 1214. Via the stretching or compressing of the compliance spring 1214, the diameter of the TED 202 and specifically of the coring element 206 can change to match the diameter of the blood vessel and a desired radial force, and/or force level can be maintained.

FIGS. 23-A to 23-H, FIGS. 24-A and 24-B, FIGS. 25-A to 25-H, FIGS. 34-A to 34-H, FIGS. 41-A to 41-F, and FIGS. 42-A and 42-B depict processes for using the thrombus extraction system 100 to remove thrombus from a patient's body, and specifically from a blood vessel, which can be a venous vessel, in the patient's body. This can includes: accessing the blood vessel via one or several percutaneous access sites that can provide direct access to the blood vessel or indirect access to the blood vessel via one or several other blood vessels; advancing the introducer sheath to a position proximate to the thrombus; deploying the self-expanding funnel of the introducer sheath; advancing the distal end 132 of the thrombus extraction catheter 104 to a position proximate to the thrombus; deploying the thrombus extraction device 202; capturing the thrombus in the thrombus extraction device 202 by retracting the thrombus extraction device 202 through the thrombus; collapsing the thrombus extraction device 202; and removing the thrombus extraction device 202 and the captured thrombus from the introducer sheath 102 and from the patient's body. In some embodiments, these one or several access sites can include, for example, a popliteal access site, a femoral access site, a mid-femoral access site, a tibial access site, a contralateral access site, an internal jugular access site, and/or other venous or arterial access sites. In some embodiments, a thrombolytic agent can be infused and/or aspirated into or from the blood vessel before, during, or after the removal or extraction of the thrombus. This thrombolytic agent can comprise, for example, a tissue plasminogen activator (TPA) or other clot dissolving medication.

In any of the herein disclosed embodiments, the device and/or delivery system may be adapted to deliver energy to the device and thrombus or tissue surrounding the device at the treatment site for the purpose of facilitating removal of thrombus or healing of tissue adjacent the device or both. In some embodiments, energy may be delivered through a delivery system to the device for treatment of a patient's vasculature such that the device is heated or actuated by the energy. Examples of energy that may be delivered include but are not limited to light energy, thermal energy, vibration energy, electromagnetic energy, radio frequency energy and ultrasonic energy. For some embodiments, energy delivered to the device may trigger the release of chemical or biologic agents to promote separation of thrombus from the vessel wall and/or to a patient's tissue for treatment of a patient's vasculature, healing of tissue disposed adjacent such a device or a combination thereof.

The process for using the thrombus extraction system 100 shown in FIGS. 22-A to 22-H, FIGS. 24-A and 24-B, FIGS. 25-A to 25-H, FIGS. 34-A to 34-D, FIGS. 41-A to 41-F, and FIGS. 42-A and 42-B can be performed with the direction of blood flow or against the direction of blood flow. Thus, in some embodiments, the direction of blood flow in FIGS. 22-A to 22-H, FIGS. 24-A and 24-B, FIGS. 25-A to 25-H, FIGS. 34-A to 34-D, FIGS. 41-A to 41-F, and FIGS. 42-A and 42-B, can be from left to right, or from right to left.

With reference now to FIGS. 23-A to 23-H, a process for expanding the thrombus extraction device 202 in a blood vessel such as a venous vessel is shown. The process for expanding the thrombus extraction device 202 in the vessel can be performed using all or portions of the thrombus extraction system 100. In some embodiments, the process for expanding the thrombus extraction device 202 in the vessel can be performed in connection with a monitoring technique, such as fluoroscopy, angiography, and/or ultrasonic monitoring. In some embodiments, the monitoring technique can be used to monitor the deployment of the TED 202 in the vessel via observation of the one or several radiopaque markers located on the introducer sheath 102 and/or the thrombus extraction catheter 104.

The process begins at FIG. 23-A, wherein a thrombus 2200 is identified in a blood vessel 2202 such as venous vessel. In some embodiments, the thrombus 2200 can be located in the peripheral vasculature of the patient's body. The thrombus 2200, also referred to herein as a clot 2200, can comprise a proximal end 2204 and the distal end 2206. In some embodiments, the identification of the blood vessel 2202 can further include the determination of whether the thrombus 2200 in the blood vessel 2202 is suitable for thrombus extraction. In some embodiments, the thrombus 2200 in the blood vessel 2202 can be suitable for extraction when the blood vessel 2202 has a diameter of at least 5 millimeters. In some embodiments, the thrombus 2200 in the blood vessel 2202 can be suitable for extraction when the blood vessel 2202 has a diameter of at least 5 millimeters and is at least one of a femoral vein, an iliac vein, a popliteal vein, a posterior tibial vein, an anterior tibial vein, or a peroneal vein.

After the thrombus has been identified, the process proceeds to the step shown in FIG. 23-B, wherein the introducer sheath 102 is advanced, either with or against the direction of blood flow in the blood vessel, such that the distal end 110 of the introducer sheath 102 and/or the obturator 120 is proximate to the thrombus 2200, and particularly is proximate to the thrombus 2200 at a position proximal of the thrombus 2200. In some embodiments, this can include providing the introducer sheath 102 and percutaneously accessing the circulatory system of the patient and specifically a blood vessel or venous vessel of the patient via an access site 2208 which can be one of the above referenced access sites.

After the introducer sheath 102 has been advanced to a desired position, the self-expanding funnel 1708 can be deployed and/or unsheathed from the constrained configuration to the expanded configuration as depicted in FIG. 23-C. In some embodiments, the self-expanding funnel 1708 can be deployed by the relative distal movement of the obturator 120 with respect to the elongate member 106 until the funnel 1708 is no longer constrained by the capture sheath 1500 and then the obturator 120 can be proximally retracted through the lumen 1701 of the elongate member 106 until the obturator 120 is removed from the introducer sheath 102.

In some embodiments, the relative distal movement of the obturator 120 with respect to the elongate member can comprise fixing the position of the obturator 120 relative to the blood vessel 2202 and proximally retracting the elongate member 106 over the obturator 120 to unsheathe the self-expanding funnel 1708 until the stop 1508 contacts the sealed aperture 112 and/or until monitoring, which can be fluoroscopic monitoring, of radiopaque markers located in, for example, the tip 1502 of the obturator 120 and the distal end 110 of the elongate member 106 indicate that the self-expanding funnel 1708 is deployed and/or is no longer constrained by the capture sheath 1500. Alternatively, in some embodiments, the relative distal movement of the obturator 120 with respect to the elongate member can comprise fixing the position of the elongate member 106 relative to the blood vessel 2202 and distally advancing the obturator 120 two unsheathe the self-expanding funnel 1708 until the stop 1508 contacts the sealed aperture 112 and/or until monitoring, which can be fluoroscopic monitoring, of radiopaque markers located in, for example, the tip 1502 of the obturator 120 and the distal end 110 of the elongate member 106 indicate that the self-expanding funnel 1708 is deployed and/or is no longer constrained by the capture sheath 1500.

After the self-expanding funnel 1708 has been deployed, a portion of the thrombus extraction catheter 104 such as the outer shaft 138 can be inserted into the lumen 1701 of the introducer sheath 102 via the sealed aperture 112 as depicted in FIG. 23-D. In some embodiments, this can include providing the thrombus extraction catheter 104 which comprises the thrombus extraction device 202. In some embodiments, the thrombus extraction device 202 can be constrained within the outer shaft 138 and can inserted, together with the outer shaft 138, into the lumen of the elongate member 106 via the sealed aperture 112. In some embodiments, the outer shaft 138 of the thrombus extraction catheter 104 can have a diameter so as to dilate the seal of the sealed aperture 112 such that the sealed aperture 112 seals around and seals to the outer shaft 138.

After the outer shaft 138 has been inserted into the lumen 1701 of the introducer sheath 102, a portion of the thrombus extraction catheter 104 can be inserted via the introducer sheath 102 into the blood vessel 2202 as depicted in FIG. 23-E. In some embodiments, the distal end 132 of the thrombus extraction catheter 104 can be advanced to a position proximate to the thrombus 2200 and/or to a position proximal to the thrombus 2200. In some embodiments, the insertion and/or advance of the thrombus extraction catheter 104 can be monitored and specifically can be fluoroscopically monitored. In some embodiments, the position of one or several radiopaque markers, including radiopaque marker 222 of the thrombus extraction catheter 104 can be monitored.

After the portion of the thrombus extraction catheter 104 has been inserted into the blood vessel 2202, a portion of the thrombus extraction catheter 104 can be distally advanced through the clot 2200 as depicted in FIG. 23-F. In some embodiments, this distal advance through the clot 2200 can be either with or against the direction of blood flow. In some embodiments, the portion of the thrombus extraction catheter 104 distally advanced through the clot 2000 can contain and/or constrain the thrombus extraction device 202. In some embodiments, distally advancing the portion of the thrombus extraction catheter 104 through the clot can include advancing the portion of the thrombus extraction catheter 104 until the radiopaque marker 222, that can be fluoroscopically monitored and that can be located at the distal end 218 of the inner shaft 200, is distally past the thrombus 2200 and/or a portion of the thrombus 2200.

After the portion of the thrombus extraction catheter 104 is distally advanced through the clot 2200, the thrombus extraction device 202 can be deployed as depicted in FIG. 23-G. In some embodiments, the thrombus extraction device 202 can be deployed by either advancing the thrombus extraction device 202 beyond the distal end 204 of the outer shaft 138 or by retracting the outer shaft 138 relative to the thrombus extraction device 202 until the thrombus extraction device 202 is beyond the distal end 204 of the outer shaft 138. In some embodiments, the thrombus extraction device can be deployed such that the thrombus extraction device 202 is distally past the thrombus 2200 and/or distally past a desired portion of the thrombus 2200.

In some embodiments, the thrombus extraction device is advanced beyond the distal end 204 of the outer shaft 138 by distally advancing the intermediate shaft 140 with respect to the outer shaft 138. In some embodiments, the intermediate shaft 140 can be distally advanced until the lock feature 146 contacts the mating feature 148, and the lock feature 146 can be mated and/or secured to the mating feature 148 to fix the relative position of the intermediate shaft 140 with respect to the outer shaft 138.

In some embodiments, the deployment of the thrombus extraction device 202 can be monitored, and specifically, the deployment of the thrombus extraction device 202 can be fluoroscopically monitored via, for example, the radiopaque marker 222 and the radiopaque marker located at one or both of the distal end 204 of the outer sheath 138 and the distal end 212 of the intermediate sheath 140. In some embodiments, the deployment of the thrombus extraction device 202, and specifically the advancing of the thrombus extraction device 202 beyond the distal end 204 of the outer shaft 138 or retracting the outer shaft 138 relative to the thrombus extraction device 202 can be ceased based on a position the distal end 204 of the outer sheath 138 comprising the radiopaque marker (first radiopaque marker) relative to the radiopaque marker 222 located on the thrombus extraction device 202 (second radiopaque marker).

After the thrombus extraction device 202 is deployed, the thrombus extraction device 202 can be fully expanded as shown in FIG. 23-H. In some embodiments, this can include allowing the full expansion of the thrombus extraction device 202 such that the thrombus extraction device 202 engages a wall 2220 of the blood vessel 2202. In some embodiments, the thrombus extraction device 202 can be fully expanded by moving the plunger 154 from the first position to the second position and securing the plunger 154 in the second position to thereby fix the relative position of the inner shaft 200 with respect to the intermediate shaft 140. In some embodiments, the movement of the plunger 154 from the first position to the second position proximally retracts the inner shaft 200 with respect to the intermediate shaft 140 to thereby fully expand the expandable cylindrical portion 208 of the thrombus extraction device 202. The proximal retraction of the inner shaft 200 with respect to the intermediate shaft 140 can further bring the stop 702 into engagement with the ring feature 700 to thereby fully expand the self-expanding coring element 206. In some embodiments, the securing of the plunger 154 in the second position can secure the self-expanding coring element 206 and the thrombus extraction device 202 in full expansion via the engagement of the stop 702 with the ring feature 700.

With reference now to FIGS. 24-A and 24-B, alternative embodiments of the steps shown in FIGS. 23-G and 23-H are shown. In some embodiments, these alternative embodiments can be performed when the diameter of the blood vessel 2202 containing the thrombus 2200 decreases below a desired level distally beyond the thrombus 2200. In some embodiments, for example, as the distance from the heart increases, the diameter of the blood vessel 2202 can decrease. In some embodiments, this diameter can decrease to a point that use of the thrombus extraction device 202 may no longer be possible.

In such an embodiment, an extension sheath 2300, also referred to herein as a popliteal sheath 2300, can be percutaneously inserted into the blood vessel 2202 through the wall 2220 of the blood vessel 2202 such that at least a portion of the extension sheath 2300 extends from the patient. In some embodiments, the extension sheath 2300 can be percutaneously inserted into the blood vessel 2202 at a position before the blood vessel diameter decreases below a desired value such as, for example, below 1 mm, 2 mm, 3 mm, 4 mm, 5 mm, 6 mm, 8 mm, 10 mm, or any other or intermediate value. In some embodiments the extension sheath 2300 can be inserted into the blood vessel 2202 via an access site such as, for example, the popliteal access site or other venous or arterial access sites.

The thrombus extraction device 202 can be deployed as depicted in FIG. 24-A. In some embodiments, the thrombus extraction device 202 can be deployed by either advancing the thrombus extraction device 202 beyond the distal end 204 of the outer shaft 138 and into the extension sheath 2300 or by advancing the outer shaft 138 containing the thrombus extraction device 202 into the extension sheath and then retracting the outer shaft 138 relative to the thrombus extraction device 202 until the thrombus extraction device 202 is beyond the distal end 204 of the outer shaft 138. In some embodiments, the thrombus extraction device can be deployed such that the thrombus extraction device 202 is distally past the thrombus 2200 and/or distally past a desired portion of the thrombus 2200. In some embodiments, all or portions of the thrombus extraction device can be contained within the extension sheath 2300.

In some embodiments, the outer shaft 138 of the thrombus extraction catheter 104 can be separable into a first piece and a second piece. In some embodiments, this separation can occur at a separation point that can comprise, for example, any feature configured to allow separation of the first and second pieces. These features can include a partial depth slit or score in the outer shaft 138, an overlapping friction fit in the outer shaft 138, or the like. In some embodiments, the separable outer shaft 138 can be used in the place of the extension sheath 2300. In such an embodiment, the outer shaft 138 can exit the blood vessel 2202 via the access site such that the separable portion extends from inside the blood vessel 2202 to outside of the patient's body at the access point. In such an embodiment, the separation portion of the outer sheath 138 can serve as the extension sheath 2300 and can remain in the access point when the thrombus extraction device 202 is retracted. Thus, the thrombus extraction device 202 can be deployed by securing the position of the separation portion of the outer sheath 138 and retracting the thrombus extraction device 202 from that separation portion of the outer sheath 138.

In some embodiments, the thrombus extraction device can be advanced beyond the distal end 204 of the outer shaft 138 by distally advancing the intermediate shaft 140 with respect to the outer shaft 138. In some embodiments, the intermediate shaft 140 can be distally advanced until the lock feature 146 contacts the mating feature 148. In some embodiments, the lock feature 146 can be mated and/or secured to the mating feature 148 to fix the relative position of the intermediate shaft 140 with respect to the outer shaft 138.

In some embodiments, the deployment of the thrombus extraction device 202 can be fluoroscopically monitored, and specifically, the deployment of the thrombus extraction device 202 can be fluoroscopically monitored via, for example, the radiopaque marker 222 and the radiopaque marker located at one or both of the distal end 204 of the outer sheath 138 and the distal end 212 of the intermediate sheath 140. In some embodiments, the deployment of the thrombus extraction device 202, and specifically the advancing of the thrombus extraction device 202 beyond the distal end 204 of the outer shaft 138 or retracting the outer shaft 138 relative to the thrombus extraction device 202 can be seized based on a position the distal end 204 of the outer sheath 138 comprising the radiopaque marker (first radiopaque marker) relative to the radiopaque marker 222 located on the thrombus extraction device 202 (second radiopaque marker).

After the thrombus extraction device 202 is deployed, the thrombus extraction device 202 can be fully expanded as shown in FIG. 24-B. in some embodiments, the thrombus extraction device 202 can be fully expanded while all or portions of the thrombus extraction device 202 are contained in the extension sheath 2300. In such an embodiment, the portions of the thrombus extraction device 202 contained in the extension sheath 2300 can be prevented from reaching full expansion by the extension sheath 2300. In such an embodiment, the thrombus extraction device 202 can reach full expansion as the thrombus extraction device is proximately retrieved from the extension sheath 2300.

In some embodiments, the full expansion of the thrombus extraction device 202 can include allowing the expansion of the thrombus extraction device 202 such that the thrombus extraction device 202 engages a wall 2220 of the blood vessel 2202. In some embodiments, the thrombus extraction device 202 can be fully expanded by moving the plunger 154 from the first position to the second position and securing the plunger 154 in the second position to thereby fix the relative position of the inner shaft 200 with respect to the intermediate shaft 140. The movement of the plunger 154 from the first position to the second position can proximally retract the inner shaft 200 with respect to the intermediate shaft 140 to thereby expand the expandable cylindrical portion 208 of the thrombus extraction device 202. In some embodiments, the proximal retraction of the inner shaft 200 with respect to the intermediate shaft 140 can further bring the stop 702 into engagement with the ring feature 700 to thereby fully expand the self-expanding coring element 206. In some embodiments, the securing of the plunger 154 in the second position can secure the self-expanding coring element 206 and the thrombus extraction device 202 in full expansion via the engagement of the stop 702 with the ring feature 700

In some such embodiments in which the TED 202 is all or wholly contained within the extension sheath 2300, the TED 202 can be retracted until the self-expanding coring element 206 is outside of the extension sheath 2300, and which point the inner shaft 200 can be decoupled from the distal end 217 of the expandable cylindrical portion 208 and the plunger 154 can be moved from the first position to the second position to bring the self-expanding coring element 206 to full expansion. The TED 202 can then be further retracted and the expandable cylindrical portion 208 can be expanded by progressively recoupling the distal end 217 of the expandable cylindrical portion 208 with the inner shaft 200 as the expandable cylindrical portion 208 exits the extension sheath 2300 until the expandable cylindrical portion 208 has completely exited the extension sheath 2300 and is at full expansion with the distal end 217 of the expandable cylindrical portion 208 recoupled to the inner shaft 140. Alternatively, in some embodiments, the distal end 217 of the expandable cylindrical portion 208 can remain uncoupled to the inner shaft 140 until the expandable cylindrical portion 208 has completely exited the extension sheath 2300. Once the expandable cylindrical portion 208 has completely exited the extension sheath 2300, the distal end 217 of the expandable cylindrical portion 208 can be recoupled to the inner shaft 200 and the expandable cylindrical portion 208 can be expanded to full expansion.

With reference now to FIGS. 25-A to 25-H a process for removal of thrombus 2200 with an expanded thrombus extraction device 202 is shown. In some embodiments, the thrombus 2200 can be removed via the capture of the thrombus in the thrombus extraction device 202 via the proximal retraction of the thrombus extraction device 202 through the thrombus 2200, which proximal retraction of the thrombus extraction device 202 can be, for example, in a direction of blood flow through the blood vessel 2202 or against the direction of blood flow through the vessel 2202. In some embodiments, the proximal retraction of the thrombus extraction device 202 through the thrombus 2200 can result in the capture of the distal end 2206 of the thrombus 2200 before the capture of the proximal end 2204 of the thrombus 2200.

In some embodiments, the proximal retraction of the thrombus extraction device 202 can result in the separation and/or coring of at least a portion of the thrombus 2200 from the wall 2220 of the blood vessel 2202 by, for example, the self-expanding coring element 206 and/or the stent portion, and the capture of that separated portion of the thrombus 2200 within the expandable cylindrical portion 208. In some embodiments, the expandable cylindrical portion 208 can be formed of the braided filament mesh structure that can be, for example, a net-like filament mesh structure. In some embodiments, a portion of the thrombus can be captured within the expandable cylindrical portion 208 by entering the expandable cylindrical portion 208 via the mouth 414 of the self-expanding coring element 206 and/or via one or several of the interstices 404 of the self-expanding coring element 206.

As seen in FIG. 25-A, the distal end 2206 of the thrombus 2200 is separated and/or cored from the walls 2220 of the blood vessel 2202 by the self-expanding coring element 206 via the proximal retraction of the thrombus extraction device 202. As seen in FIG. 25-B, the distal end 2206 of the thrombus 2200 is captured in the expandable cylindrical portion 208 of the thrombus extraction device by the continued proximal retraction of the thrombus extraction device through the thrombus 2200. The separation and capture and/or coring and capture of further portions of the thrombus 2200 by the continued proximal retraction of the thrombus extraction device 202 is shown in FIGS. 25-C, 25-D, and 25-E. As seen in FIG. 25-E, the proximal end 2204 of the thrombus 2200 is cored and captured as the thrombus extraction device 202 is proximally retracted towards the self-expanding funnel 1708.

In some embodiments, the thrombus extraction device 202 can be proximally retracted until a portion of the self-expanding coring element 206 is contained within the self-expanding funnel 1708 as seen in FIG. 25-F, and specifically until the mouth 414 of the self-expanding coring element 206 is contained within the self-expanding funnel 1708. In some embodiments, the containment of the mouth 414 within the self-expanding funnel 1708 can be fluoroscopically verified. In some embodiments, the mouth 414 can be determined as wholly contained within the self-expanding funnel 1708 via fluoroscopic monitoring based on the alignment/relative positioning of the distal end 212 of the intermediate shaft 140 comprising a radiopaque marker 2450 and/or the radiopaque marker 222 with respect to the distal end 110 comprising a radiopaque marker 2452 of the elongate member 106 of the introducer sheath 102.

When the portion of the self-expanding coring element 206 is contained within the self-expanding funnel 1708, or specifically when the mouth 414 of the self-expanding coring element 206 is wholly contained within the self-expanding funnel 1708, the plunger 154 can be unlocked from the second position and can be moved from the second position to the first position to thereby move the thrombus extraction device 202 from and expanded configuration to an unexpanded configuration. In some embodiments, the unlocking of the plunger 154 from the second position can unlock and/or decouple the inner shaft 200 with respect to the intermediate shaft 140, and the moving of the plunger 154 from the second position to the first position can cause the distal advancing of the inner shaft 200 relative to the intermediate shaft 140.

In some embodiments, the thrombus extraction device 202 can be collapsed by moving the thrombus extraction device 202 from the expanded configuration to the unexpanded configuration prior to withdrawing the thrombus extraction device 202 from the patient's body so as to compress the thrombus 2200 captured by the thrombus extraction device 202. In some embodiments, the compression of the thrombus 2200 by the thrombus extraction device 202 can secure the position of the thrombus within the thrombus extraction device 202 via, in some embodiments, the engagement of one or several of the plurality of circumferential depressions 1000 with the thrombus 2200.

After the thrombus extraction device 202 has been collapsed, the thrombus extraction device 202 can be proximally retracted through the self-expanding funnel 1708 and into the elongate member 106 as depicted in FIG. 25-G. In some embodiments, the collapse of the thrombus extraction device 202 and/or the retraction of the thrombus extraction device 202 into the self-expanding funnel 1708 and/or the elongate member can result in the extrusion of all or portions of the thrombus 2200 through pores of the expandable cylindrical portion 208 of the thrombus extraction device 202 including, for example, some or all of the first plurality of pores 904 and/or the second plurality of pores 906. In some embodiments, the all or portions of the thrombus 2200 can be extruded through some or all of the second plurality of pores 906 which can be larger than the first plurality of pores 904. In some embodiments, the pores in the second plurality of pores 906 can be sized to be sufficiently small such that any thrombus portions of the thrombus 2200 extruded through the pores is sufficiently small to have little or no clinical significance. In some embodiments, these extruded all or portions of the thrombus 2200 can be captured by the self-expanding funnel 1708.

The thrombus extraction device 202 can continue to be proximally retracted as depicted in FIG. 25-H until the thrombus extraction device 202 and the captured thrombus 2200 is fully contained within the elongate member 106. In some embodiments, the seal dilator 170 can be inserted into the sealed aperture 112 and the thrombus extraction device 202 and the captured thrombus 2200 can then be withdrawn or removed from the patient's body and from the elongate member 106 via the sealed aperture 112 in the seal dilator 170. In some embodiments, thrombus captured by the self-expanding funnel 1708 can then either be guided into the elongate member 106 and specifically into the lumen 1701 of the elongate member 106 or further compressed and/or broken up by the self-expanding funnel 1708 and then allowed to pass through the self-expanding funnel 1708, and particularly through the mesh of the self-expanding funnel 1708. In some embodiments, this thrombus can be aspirated through the lumen 1701 of the elongate member 106 and the aspiration port 114. In some embodiments, the aspiration of the thrombus via the aspiration port 114 can include the opening of the aspiration valve 118. After the thrombus is captured by the self-expanding funnel 1708 has been aspirated, the introducer sheath 102 can be removed from the patient's body.

Figure 26:
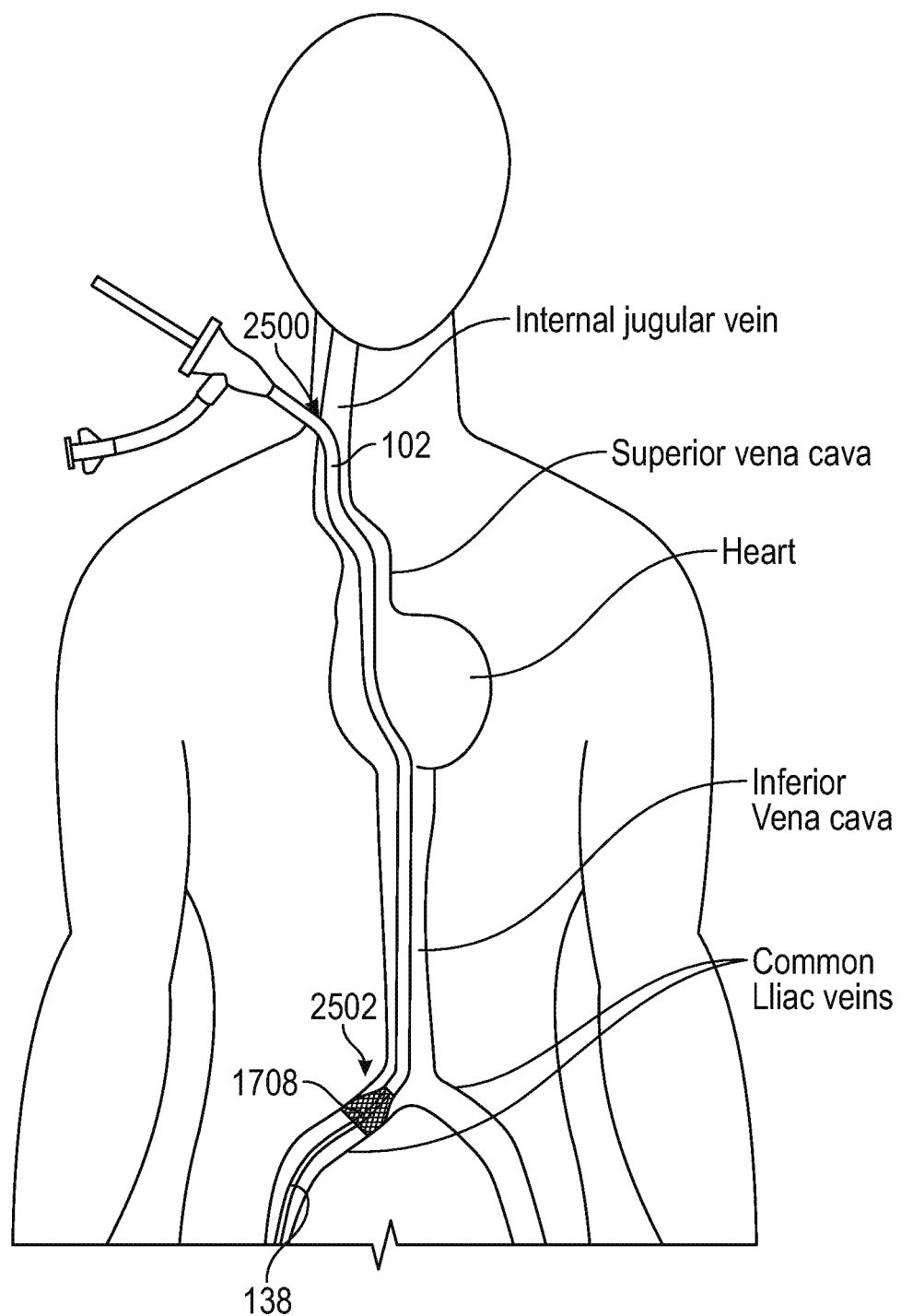
FIG. 26 is a schematic depiction of one embodiment of accessing the blood vessel via an internal jugular access site.
Figure 27:
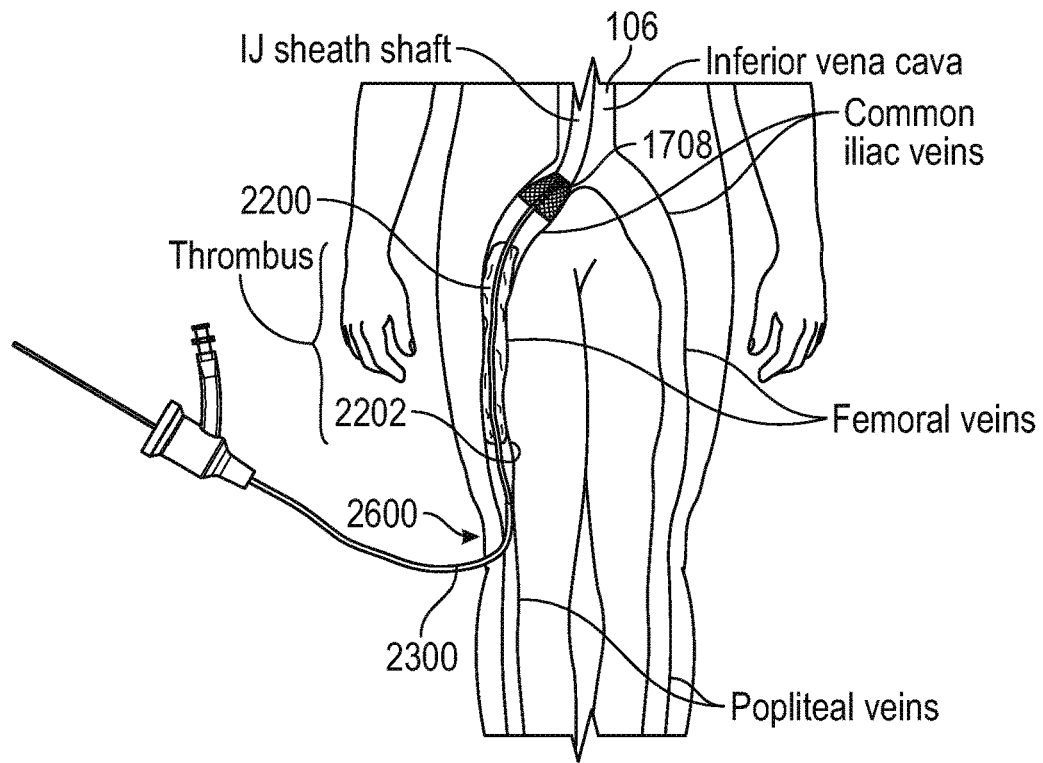
FIG. 27 is a schematic depiction of one embodiment of accessing the blood vessel via a popliteal access site with an extension sheath 2300.
Figure 28:
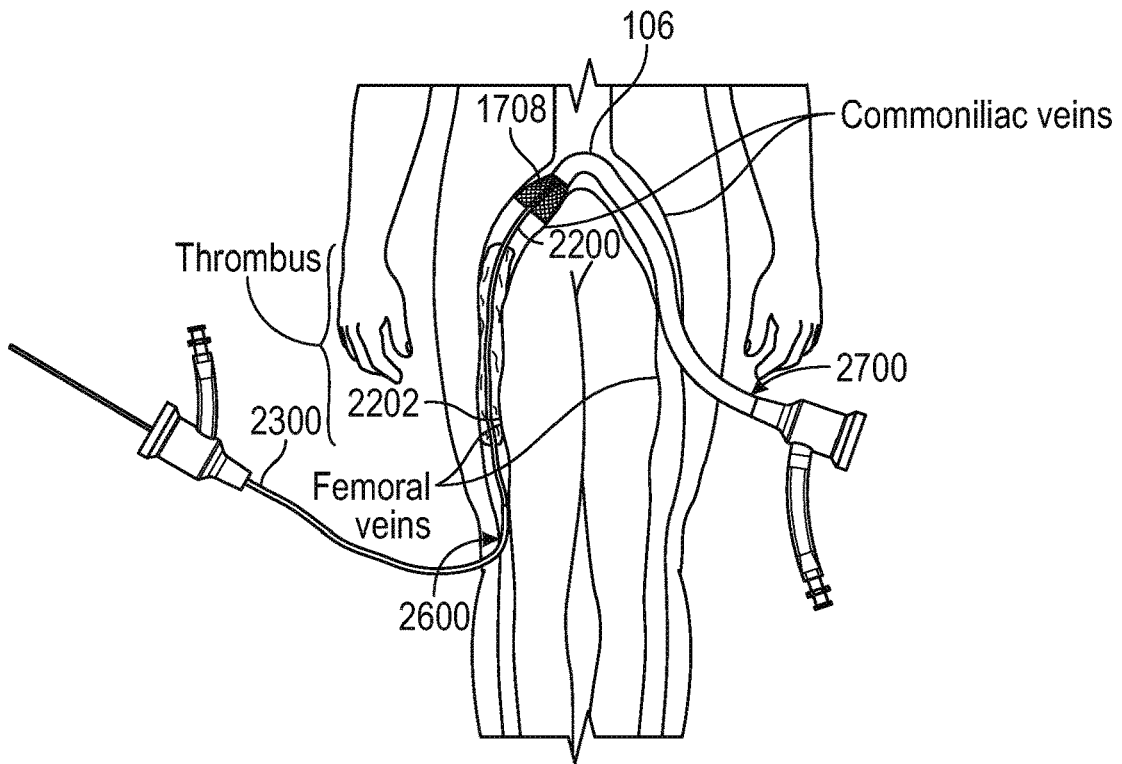
FIG. 28 is a schematic depiction of one embodiment of accessing the blood vessel via a popliteal access site and a femoral access site.

With reference now to FIGS. 26-28, introduction techniques for accessing the thrombus 2200 are shown. In some embodiments, these introduction techniques can allow the use of a larger sized introducer sheath 102 due to the larger size of the vessels in the path to the thrombus. In some embodiments, this larger size of the introducer sheath 102 can ease the removal of thrombus through the introducer sheath 102 as, in some embodiments, the size of the lumen 1701 of the introducer sheath 102 can increase as the size of the introducer sheath 102 increases. Further, in some embodiments, the user of a larger sized introducer sheath 102 can allow the removal of larger thrombus. In some embodiments, the lengths of the components of the thrombus extraction system 100, and particularly the lengths of the introducer sheath 102 and the thrombus extraction catheter 104 can vary based on the selected technique for accessing the thrombus and/or based on the location of the thrombus.

As seen in FIG. 26, the introducer sheath 102 can be inserted into the patient's body via an internal jugular access site 2500. The introducer sheath 102 can extend from the internal jugular access site 2500 to the deployment position 2502 which can be proximal to the thrombus 2200. In embodiments in which the introducer sheath 102 comprises the self-expanding funnel 1708, the self-expanding funnel 1708 can be deployed at the deployment position 2502. In the embodiment shown in FIG. 26, the introducer sheath can extend from the internal jugular access site 2500 through the superior vena cava and the inferior vena cava to the deployment position 2502 in one of the common iliac veins. In some embodiments, the deployment position 2502 can be located in, for example, the inferior vena cava, one of the iliac veins, the femoral vein, the popliteal vein, before or beyond the iliac arch, or any other location proximate to and/or proximal to the thrombus 2200. In some embodiments, the use of the internal jugular access site 2500 can allow for a larger diameter of the elongate member 106.

As seen in FIG. 27, in some embodiments, use of the internal jugular access site 2500 can be combined with use of the extension sheath 2300 that can be inserted into the blood vessel 2202 at a popliteal access site 2600. In some such embodiments, the thrombus extraction device can wholly or partially exit the patient's body while contained in the extension sheath 2300 before being retracted through the thrombus 2200.

As seen in FIG. 28, the introducer sheath can, in some embodiments, be inserted into the patient's body into an access site connected to the blood vessel 2202 containing the thrombus via the common iliac veins. In the specific embodiment shown in FIG. 28, this can be achieved via insertion into the patient's body via a femoral access site 2700. In some embodiments, use of an access site connected to the blood vessel 2202 via the common iliac veins, and specifically user of the femoral access site 2700 can be combined with user of the extension sheath 2300 that can be inserted into the blood vessel 2202 at a popliteal access site 2600. In some such embodiments, the thrombus extraction device can wholly or partially exit the patient's body while contained in the extension sheath 2300 before being retracted through the thrombus 2200.

Figure 29:
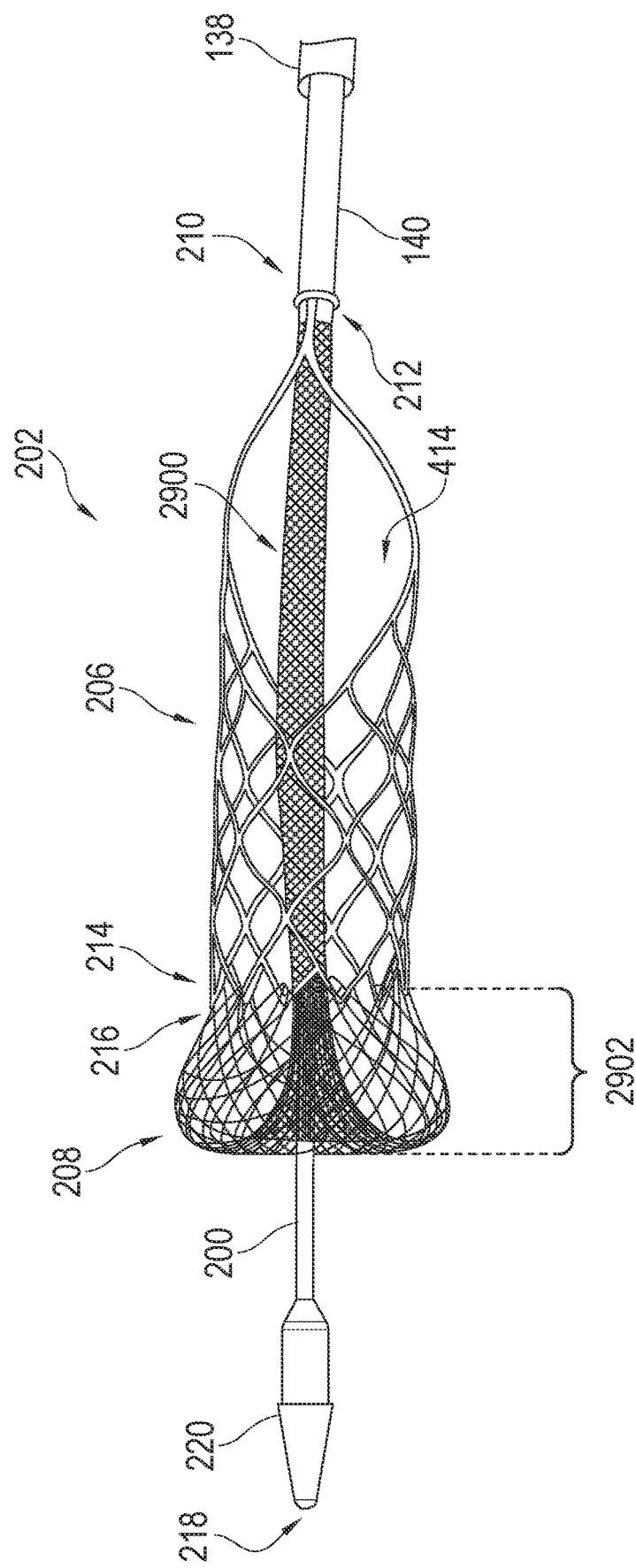
FIG. 29 is a side view of an embodiment of the thrombus extraction device with an everted portion.

With reference now To FIG. 29, a side view of another embodiment of the thrombus extraction device 202 is shown. The TED 202 shown in FIG. 29 can be used with other components of the thrombectomy system 100 shown and discussed above. The thrombus extraction device 202 can include the self-expanding coring element 206, and the expandable cylindrical portion 208 that can be the braided filament mesh structure 704. The self-expanding coring element 206, which can include the mouth 414, also referred to herein as the opening 414, can be relatively more proximally located on the thrombus extraction catheter 104 than the expandable cylindrical portion 208. The self-expanding coring element 206 can include a proximal end 210 connecting to a distal end 212 of the intermediate shaft 140 and a distal end 214 connecting to a proximal end 216 of the expandable cylindrical portion 208.

The distal end 217 of the expandable cylindrical portion 208 can connect to one of: the second intermediate shaft 3000, the third intermediate shaft 3002; and the inner shaft 200. In some embodiments, this connection can be to a distal end 218 of the one of: the second intermediate shaft 3000, the third intermediate shaft 3002; and the inner shaft 200, and in some embodiments, this connection can be at a location intermediate between the proximal end and the distal end 218 of the one of: the second intermediate shaft 3000, the third intermediate shaft 3002; and the inner shaft 200. In some embodiments, this connection can be a fixed connection and in some embodiments, this connection can be a slidable connection.

The expandable cylindrical portion 208 can include an everted portion 2900 and a non-everted portion 2902. In some embodiments, the non-everted portion can be proximate to the proximal end 216 of the expandable cylindrical portion 208 and can connect to the self-expanding coring element 206. The everted portion 2900 can, in some embodiments, extend proximally through the non-everted portion 2902 and/or through the self-expanding coring element 206, and particularly through the mouth 414 of the self-expanding coring element 206. The distal end 217 of the expandable cylindrical portion 208 can be moveable with respect to the self-expanding coring element 206 such that the relative size and/or length of the everted portion 2900 changes with respect to the size and/or length of the non-everted portion 2902. In embodiments in which the distal end 217 of the expandable cylindrical portion 208 is fixed to one of: the second intermediate shaft 3000, the third intermediate shaft 3002; and the inner shaft 200, the length of the everted portion 2900 relative to the non-everted portion 2902 varies based on the position of the first intermediate shaft 140 relative to the position of the one of: the second intermediate shaft 3000, the third intermediate shaft 3002; and the inner shaft 200 to which the self-expanding coring element 206 is connected.

The distal end 218 of the inner shaft 200 can further include a tip 220 such as an atraumatic tip and/or a radiopaque marker 222. In some embodiments, the tip 220 can include the radiopaque marker 222. Further radiopaque markers can be located on, for example, the outer shaft 138 and specifically the distal end 204 of the outer shaft 138 and/or the distal end 212 of the intermediate shaft 140. In some embodiments, one or both of the distal end 204 of the outer shaft 138 and the distal end 212 of the intermediate shaft 140 can each comprise a radiopaque marker. In some embodiments, the atraumatic tip 220 can define a channel configured to allow the guidewire to pass through the atraumatic tip 220.

Figure 30:
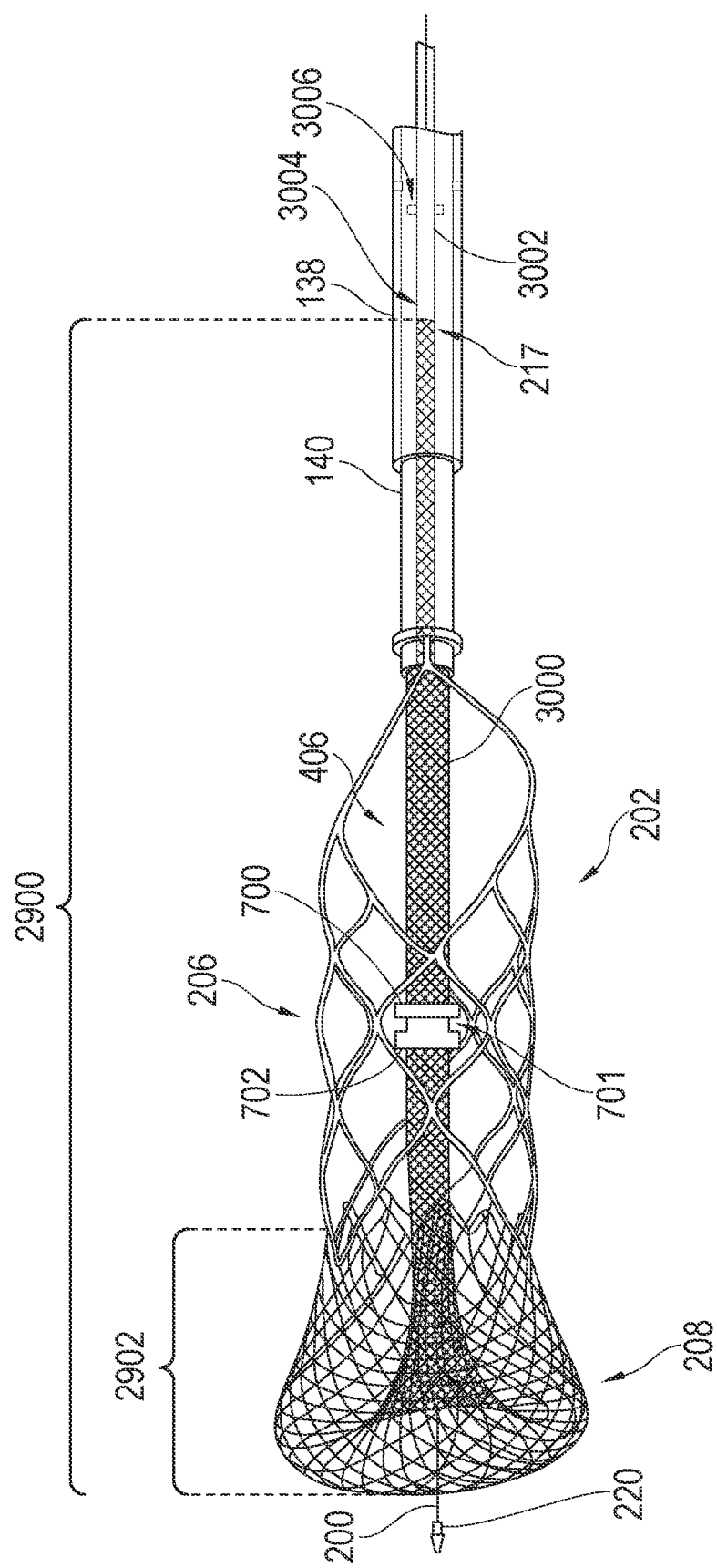
FIG. 30 is a side, section view of an embodiment of the thrombus extraction device with an everted portion and an expansion mechanism.
Figure 31:
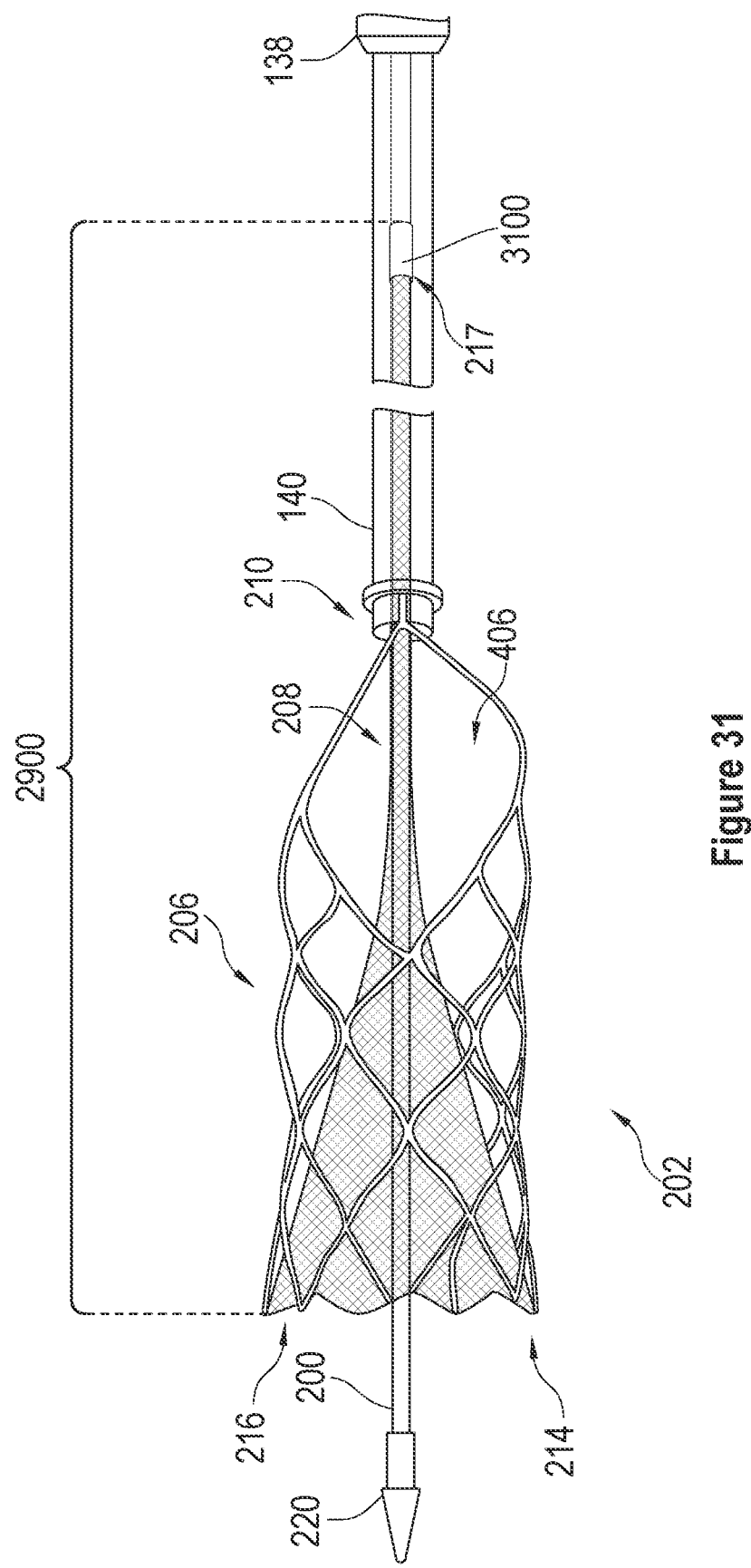
FIG. 31 is a side, section view of an embodiment of the thrombus extraction device with an everted portion and a coupling.

With reference now to FIGS. 30 and 31, side, section views of other embodiments of the thrombus extraction device 202 and portions of the thrombus extraction catheter 104 are shown. Specifically, FIG. 30 depicts an embodiment of the thrombus extraction device 202 in which the expandable cylindrical portion 208 everts on itself. As depicted, the everted portion 2900 of the expandable cylindrical portion 208 is everted such that the everted portion 2900 of the expandable cylindrical portion 208 extends through the non-everted portion 2902 and through the self-expanding coring element 206, and specifically, the everted portion 2900 is everted such that the everted portion 2900 extends proximally through the non-everted portion 2902 and proximally through the self-expanding coring element 206.

In FIG. 30, the thrombus extraction device 202 includes the self-expanding coring element 206, and the expandable cylindrical portion 208. The self-expanding coring element 206 includes the mouth 414. Further, the distal end 217 of the expandable cylindrical portion 208 connects to a distal end 3004 of the third intermediate shaft 3002 that coaxially extends through a lumen of the second intermediate shaft 3000, which likewise coaxially extends through the first intermediate shaft 140. As further seen, the thrombus extraction device 202 includes the inner shaft 200 including the atraumatic tip 220. In one embodiment the inner shaft 200 is not coupled with the expandable cylindrical portion 208, but rather is independently movable with respect to the expandable cylindrical portion 208. In another embodiment, the inner shaft 200 is fixed to the proximal end of the expandable cylindrical portion 208 and can be manipulated to purposefully expand or retract the cylindrical portion 208.

The second intermediate shaft 3000 includes a stop 702 that, with the ring 700 of the self-expanding coring element 206, is part of the expansion mechanism 701. In some embodiments, this stop 702 can be a tab, a protrusion, a flange, a ridge or the like. The expansion mechanism 701 can, with components discussed above with respect to FIGS. 12-14, be configured to maintain a desired radial force on a vessel wall with the unitary fenestrated structure and/or to hold the thrombus extraction device 202 and/or the self-expanding coring element 206 at full expansion and/or in full expansion.

In some embodiments, the stop 702 can directly engage with the ring 700 and in some embodiments, the stop 702 can be coupled with the ring 700 via, for example, a force transfer features such as spring which can be a compression spring or a tension spring. In some embodiments, for example, the stop 702 can be proximally located with respect to the ring 700 can the stop and the ring can be coupled by a tension spring such that a force is applied to the ring 700 via the spring when the stop 702 is in position for full expansion.

In some embodiments, the expandable cylindrical portion 208 can be coupled and/or connected to a distal end 218 of the one of: the second intermediate shaft 3000, the third intermediate shaft 3002; and the inner shaft 200, and in some embodiments, the expandable cylindrical portion 208 can be coupled and/or connected to a distal end 218 of the one of: the second intermediate shaft 3000, the third intermediate shaft 3002; and the inner shaft 200 at a location intermediate between the proximal end and the distal end 218 of the one of: the second intermediate shaft 3000, the third intermediate shaft 3002; and the inner shaft 200. In some embodiments, this connection can be a fixed connection and in some embodiments, this connection can be a slidable connection.

The expandable cylindrical portion 208 can include an everted portion 2900 and a non-everted portion 2902. In some embodiments, the non-everted portion 2902 can be proximate to the proximal end 216 of the expandable cylindrical portion 208 and can connect to the self-expanding coring element 206. The everted portion 2900 can, in some embodiments, extend proximally through the non-everted portion 2902 and/or through the self-expanding coring element 206, and particularly through the mouth 414 of the self-expanding coring element 206. The distal end 217 of the expandable cylindrical portion 208 can be moveable with respect to the self-expanding coring element 206 such that the relative size and/or length of the everted portion 2900 changes with respect to the size and/or length of the non-everted portion 2902. In embodiments in which the distal end 217 of the expandable cylindrical portion 208 is fixed to one of: the second intermediate shaft 3000, the third intermediate shaft 3002; and the inner shaft 200, the length of the everted portion 2900 relative to the non-everted portion 2902 varies based on the position of the first intermediate shaft 140 relative to the position of the one of: the second intermediate shaft 3000, the third intermediate shaft 3002; and the inner shaft 200 to which the self-expanding coring element 206 is connected.

The distal end 218 of the inner shaft 200 can further include a tip 220 such as an atraumatic tip and/or a radiopaque marker 222. In some embodiments, the tip 220 can include the radiopaque marker 222. Further radiopaque markers can be located on, for example, the outer shaft 138 and specifically the distal end 204 of the outer shaft 138 and/or the distal end 212 of the intermediate shaft 140. In some embodiments, one or both of the distal end 204 of the outer shaft 138 and the distal end 212 of the intermediate shaft 140 can each comprise a radiopaque marker. In some embodiments, the atraumatic tip 220 can define a channel configured to allow the guidewire to pass through the atraumatic tip 220.

In some embodiments, the thrombus extraction catheter 104 can include an eversion stop 3006. The eversion stop 3006 can include one or several features that limit the proximal displacement of the distal end 217 of the expandable cylindrical portion 208 to prevent over-eversion of the TED 202. In some embodiments, the eversion stop 3006 can be configured to limit proximal movement of the one of: the second intermediate shaft 3000, the third intermediate shaft 3002; and the inner shaft 200 to which the distal end 217 of the expandable cylindrical portion 208 is coupled. In some embodiments, this can prevent full eversion of the expandable cylindrical portion 208.

The eversion stop 3006 can increase the effectiveness of the thrombus extraction device 202. In some embodiments, for example, the eversion of the expandable cylindrical portion 208 on the self-expanding coring element 206 can result in the inability to distally advance the distal end 217 of the expandable cylindrical portion 208 to fully deploy the expandable cylindrical portion 208.

FIG. 31 depicts and embodiment of the thrombus extraction device 202 in which the expandable cylindrical portion 208 everts on the self-expanding coring element 206. As depicted in FIG. 31, the everted portion 2900 of the expandable cylindrical portion 208 connects directly to the distal end 214 of the self-expanding coring element 206 and is everted such that the everted portion 2900 of the expandable cylindrical portion 208 extends through the self-expanding coring element 206, and specifically, the everted portion 2900 is everted such that the everted portion 2900 extends proximally through the self-expanding coring element 206. As further seen, the thrombus extraction device 202 includes the inner shaft 200 including the atraumatic tip 220. The inner shaft 200 is coupled with the expandable cylindrical portion 208 via a coupling 3100, which coupling 3100 can fixedly couple the distal end 217 of the expandable cylindrical portion 208 to the inner shaft 200 and/or which coupling 3100 can slidably couple the distal end 217 of the expandable cylindrical portion 208 to the inner shaft 200. In some embodiments, the distal end 217 of the expandable cylindrical portion 208 can be similarly coupled to either the second intermediate shaft 3000 or the third intermediate shaft 3002. In some embodiments in which the coupling 3100 fixedly couples the distal end 217 of the expandable cylindrical portion 208 to the inner shaft 200, the relative length of the everted portion 2900 and the non-everted portion 2902 can be changed via the relative displacement of the inner shaft 200 with respect to the first intermediate shaft 140. In embodiments in which the coupling 3100 slidably couples the distal end 217 of the expandable cylindrical portion 208 to the inner shaft 200, the relative length of the everted portion 2900 and the non-everted portion 2902 can be changed via the application of a force to the expandable cylindrical portion 208 such as, for example, the force applied to the expandable cylindrical portion 208 by the portion of the thrombus when the thrombus extraction device 202 is retracted through the thrombus.

Although the embodiment of FIG. 31 depicts the expandable cylindrical portion 208 connected to the inner shaft 200, the expandable cylindrical portion 208 can be coupled and/or connected to a distal end 218 of the one of: the second intermediate shaft 3000, the third intermediate shaft 3002; and the inner shaft 200, and in some embodiments, the expandable cylindrical portion 208 can be coupled and/or connected to a distal end 218 of the one of: the second intermediate shaft 3000, the third intermediate shaft 3002; and the inner shaft 200 at a location intermediate between the proximal end and the distal end 218 of the one of: the second intermediate shaft 3000, the third intermediate shaft 3002; and the inner shaft 200.

Figure 32:
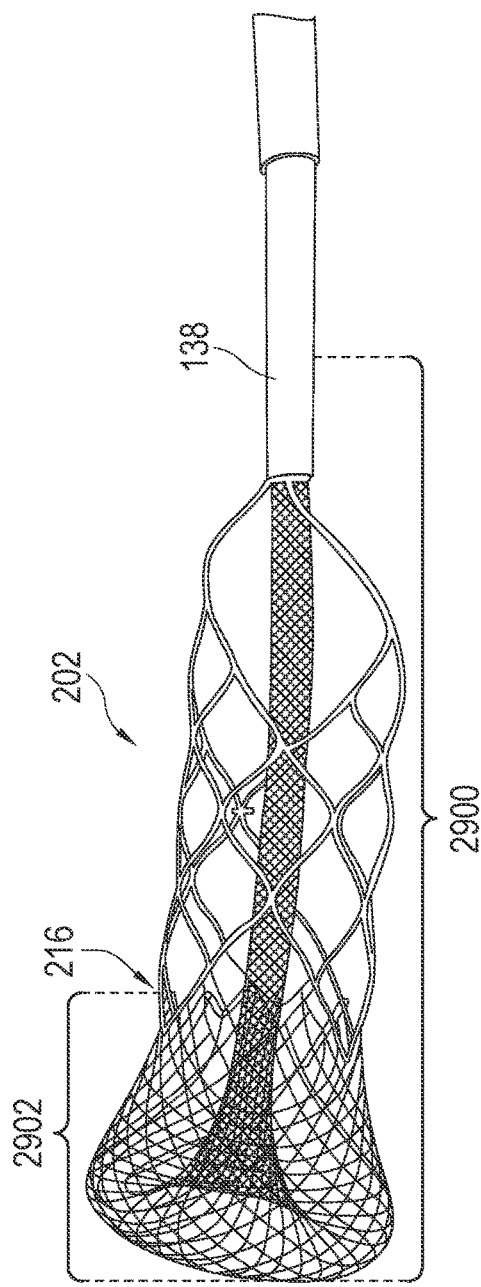
FIG. 32 is a side view of one embodiment of the thrombus extraction device with an everted portion having a first length.
Figure 33:
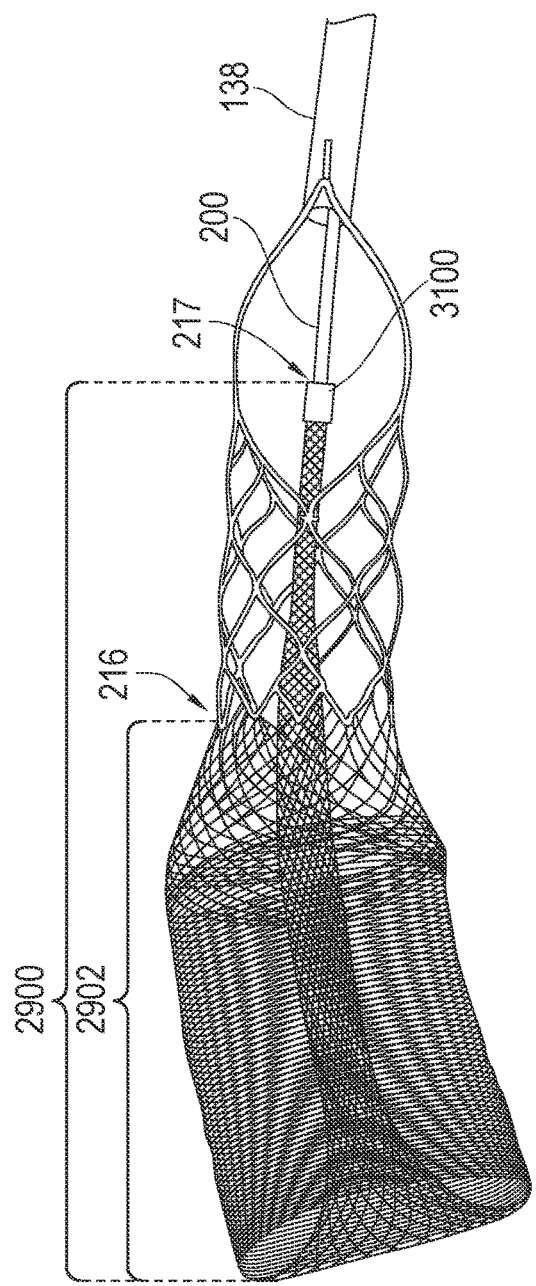
FIG. 33 is a side view of one embodiment of the thrombus extraction device with an everted portion having a second length.

With reference now to FIGS. 32 and 33, an embodiment of the TED 202 is shown in which the relative sizes and/or lengths of the everted portion 2900 and the non-everted portion 2902 differ. Thus, relative length of the everted portion 2900 with respect to the non-everted portion 2902 is greater in FIG. 32 than in FIG. 33. As depicted in FIGS. 32 and 33, the relative length and/or size of the everted portion 2900 with respect to the non-everted portion 2902 is changed via the relative position of the inner shaft 200 with respect to the first intermediate shaft 140 as the inner shaft 200 is distally advanced with respect to the first intermediate shaft 140 in FIG. 33 as compared to FIG. 32 such that the inner shaft 200 distally extends from the first intermediate shaft 140 in FIG. 33.

As further seen in FIG. 33, the length of the everted portion 2900 extends from the most distal inflection point between the everted portion 2900 and the non-everted portion 2902 until the most distal end 217 of the expandable cylindrical portion 208, which can include, for example, the coupling 3100. In the embodiment of FIG. 32, while the distal end 217 is within the first intermediate shaft 140, and thus not visible, the everted portion 2900 nevertheless extends to this distal end 217 of the expandable cylindrical portion 208. As further seen the everted portion 2900 extends from the most distal inflection point between the everted portion 2900 and the non-everted portion 2902 until the proximal end 216 of the expandable cylindrical portion 208.

With reference now to FIGS. 34-A to 34-D views depicting one embodiment of a process for affecting the relative lengths of the everted portion 2900 and the non-everted portion 2902 of a thrombus extraction device in a blood vessel 2202 are shown. In some embodiments, the process of FIGS. 34-A to 34-D can be performed as a part of, or in the place of the process shown in FIGS. 23-A to 23-H, and particularly in the place of steps 23-G and 23-H. In some embodiments, the process of FIGS. 34-A to 34-D can be performed as a part of or in the place of the process of FIGS. 24-A and 24-B, or of FIGS. 25-A to 25-H. In some embodiments, for example, the process of FIGS. 34-A to 34-D can advantageously eliminate the necessity of performing the process of FIGS. 24-A and 24-B as the expandable cylindrical portion 208 of the thrombus extraction device 202 can be controlled to limit the extension of the thrombus extraction device 202 beyond the thrombus 2200. This benefit of the process of FIGS. 34-A to 34-D is particularly advantageous when the thrombus 2200 forms proximate to a feature 3400 such as the valve 3400.

The process for affecting the relative lengths of the everted portion 2900 and the non-everted portion 2902 in a blood vessel 2202 can be performed using all or portions of the thrombus extraction system 100. In some embodiments, the process for affecting the relative lengths of the everted portion 2900 and the non-everted portion 2902 in a blood vessel 2202 can be performed in connection with a monitoring technique, such as fluoroscopy, angiography, and/or ultrasonic monitoring. In some embodiments, the monitoring technique can be used to monitor the deployment of the thrombus extraction device 202 in the vessel via observation of the one or several radiopaque markers located on the introducer sheath 102 and/or the thrombus extraction catheter 104.

The process begins at FIG. 34-A, wherein the thrombus 2200 is identified in the blood vessel 2202 such as venous vessel. In some embodiments, the thrombus 2200 can be located in the peripheral vasculature of the patient's body. The thrombus 2200 can comprise the proximal end 2204 and the distal end 2206. In some embodiments, the identification of the blood vessel 2202 can further include the determination of whether the thrombus 2200 in the blood vessel 2202 is suitable for thrombus extraction. In some embodiments, the thrombus 2200 in the blood vessel 2202 can be suitable for extraction when the blood vessel 2202 has a diameter of at least 3 millimeters. In some embodiments, the thrombus 2200 in the blood vessel 2202 can be suitable for extraction when the blood vessel 2202 has a diameter of at least 3 millimeters and is at least one of a femoral vein, an iliac vein, a popliteal vein, a posterior tibial vein, an anterior tibial vein, or a peroneal vein. In some embodiments, and as part of identifying the thrombus 2200, a feature 3400 can be identified, which feature 3400 can be located distal of the distal end 2206 of the thrombus 2200.

After the thrombus 2200 has been identified, a guidewire 3402 can be inserted through the blood vessel 2202, through the thrombus 2200, and in some embodiments, through the feature 3400. In some embodiments, the guidewire 3402 can be inserted into the blood vessel via an access site such as, for example, the internal jugular (IJ) access site, the femoral access site, the popliteal access site, or other venous or arterial access sites. In some embodiments, the guidewire 3402 can be inserted using one or several imaging and/or monitoring techniques including, for example, fluoroscopy, angiography, and/or ultrasonic monitoring.

After the thrombus 2200 has been identified, a portion of the thrombus extraction catheter 104 such as the outer shaft 138 can be inserted into the blood vessel 2202 as shown in FIG. 34-B. In some embodiments, the thrombus extraction catheter 104 including the thrombus extraction device can be inserted into the blood vessel via an access site such as, for example, the internal jugular (IJ) access site, the femoral access site, the popliteal access site, or other venous or arterial access sites. In some embodiments, the thrombus extraction catheter 104 including the thrombus extraction device can be inserted into the popliteal access site and distally advanced, towards the feet of the patient. In some embodiments, the thrombus extraction device contained within the thrombus extraction catheter 104 can include the everted portion and the non-everted portion.

In some embodiments, the insertion of the thrombus extraction catheter 104 such as the outer shaft 138 can be inserted into the blood vessel 2202 can include performing the steps discussed above with respect to FIGS. 23-B to 23-D. In some embodiments, inserting a portion of the thrombus extraction catheter 104 into the blood vessel 2202 can include providing the thrombus extraction catheter 104 which comprises the thrombus extraction device 202. In some embodiments, the thrombus extraction device 202 can be constrained within the outer shaft 138 and can inserted, together with the outer shaft 138, into the blood vessel 2202 via, for example insertion into lumen of the elongate member 106 via the sealed aperture 112. In some such embodiments, the outer shaft 138 of the thrombus extraction catheter 104 can have a diameter so as to dilate the seal of the sealed aperture 112 such that the sealed aperture 112 seals around and seals to the outer shaft 138.

After the portion of the thrombus extraction catheter 104 has been inserted into the blood vessel 2202, a portion of the thrombus extraction catheter 104 can be distally advanced through the clot 2200 as depicted in FIG. 34-B. In some embodiments, this distal advance through the clot 2200 can be either with or against the direction of blood flow. In some embodiments, the portion of the thrombus extraction catheter 104 distally advanced through the clot 2000 can contain and/or constrain the thrombus extraction device 202. In some embodiments, distally advancing the portion of the thrombus extraction catheter 104 through the clot can include advancing the portion of the thrombus extraction catheter 104 until the tip 220 reaches a desired location proximate and/or proximal to the feature 3400. In some embodiments, distally advancing the portion of the thrombus extraction catheter 104 through the clot can include advancing the portion of the thrombus extraction catheter 104 until the tip 220 reaches a desired location distal to the feature 3400.

In some embodiments, this desired location can be intermediate between with the feature 3400 and the distal end 2206 of the thrombus 2200. In some embodiments, the desired location can be sufficiently distal from the distal end 2206 of the thrombus to allow the deployment of the thrombus extraction device 202, and particularly of the self-expanding coring element 206 between the distal end 2206 of the thrombus 2200 and the feature 3400. In some embodiments, the desired location can be sufficiently distal from the distal end 2206 of the thrombus to allow the deployment of the thrombus extraction device 202, and particularly of the self-expanding coring element 206 between the distal end 2206 of the thrombus 2200 and the feature 3400 without having all or a portion of the tip 220 or all or a portion of the thrombus extraction device 202 extend through the feature 3400. In some embodiments such positioning that does not extend through the feature 3400 can protect the valve from potential damage arising from the insertion or retraction of the all or a portion of the tip 220 or all or a portion of the thrombus extraction device 202 through the feature 3400.

In some embodiments, the insertion of the portion of the thrombus extraction catheter 104 into the blood vessel 2202 can be fluoroscopically monitored based on, for example, one or several radiopaque markers located in portions of the thrombus extraction catheter 104 including, for example, the radiopaque marker 222 and the radiopaque marker located at one or both of the distal end 204 of the outer sheath 138 and the distal end 212 of the intermediate sheath 140 such as radiopaque marker 2450.

After the portion of the thrombus extraction catheter 104 is distally advanced to the desired location, the thrombus extraction device 202 can be deployed as depicted in FIG. 34-C. In some embodiments, the thrombus extraction device 202 can be deployed by either advancing the thrombus extraction device 202 beyond the distal end 204 of the outer shaft 138 or by retracting the outer shaft 138 relative to the thrombus extraction device 202 until the thrombus extraction device 202 is beyond the distal end 204 of the outer shaft 138. In some particular embodiments, the position of the tip 220 can be fixed and/or pinned at the desired location and the thrombus extraction device 202 can be deployed by the proximal retraction of the outer shaft 138 relative to the thrombus extraction device 202 until the self-expanding coring element 206 and any portion of the expandable cylindrical portion 208 extending distally from the self-expanding coring element 206 is beyond the distal end 204 of the outer shaft 138. In some embodiments, the thrombus extraction device can be deployed such that the self-expanding coring element 206 is distally past the thrombus 2200 and/or distally past a desired portion of the thrombus 2200.

In some embodiments, the thrombus extraction device 202 deployed when the lock feature 146 contacts the mating feature 148. In such embodiments, the lock feature 146 can be mated and/or secured to the mating feature 148 to fix the relative position of the intermediate shaft 140 with respect to the outer shaft 138.

In some embodiments, the deployment of the thrombus extraction device 202 can be monitored, and specifically, the deployment of the thrombus extraction device 202 can be fluoroscopically monitored via, for example, the radiopaque marker 222 and the radiopaque marker located at one or both of the distal end 204 of the outer sheath 138 and the distal end 212 of the intermediate sheath 140. In some embodiments, the deployment of the thrombus extraction device 202, and specifically the advancing of the thrombus extraction device 202 beyond the distal end 204 of the outer shaft 138 or retracting the outer shaft 138 relative to the thrombus extraction device 202 can be ceased based on a position the distal end 204 of the outer sheath 138 comprising the radiopaque marker (first radiopaque marker) relative to the radiopaque marker 222 located on the thrombus extraction device 202 (second radiopaque marker).

After the thrombus extraction device 202 is deployed, or as a part of that deployment, the thrombus extraction device 202 can be fully expanded. In some embodiments, this can include allowing the full expansion of the self-expanding coring element 206 such that the self-expanding coring element 206 engages a wall 2220 of the blood vessel 2202. In some embodiments, the thrombus extraction device 202, and specifically the self-expanding coring element 206 can be fully expanded by engaging the locking mechanism 701, and in some embodiments by moving the plunger 154 from the first position to the second position and securing the plunger 154 in the second position to thereby fix the relative position of the stop 702 with respect to the ring feature 700. In some embodiments, the movement of the plunger 154 from the first position to the second position proximally retracts the stop 702 with respect to the ring feature 700 to thereby fully expand the self-expanding coring element 206 of the thrombus extraction device 202. The proximal retraction of the plunger 154 with respect to the intermediate shaft 140 can further bring the stop 702 into engagement with the ring feature 700 to thereby fully expand the self-expanding coring element 206. In some embodiments, the securing of the plunger 154 in the second position can secure the self-expanding coring element 206 and the thrombus extraction device 202 in full expansion via the engagement of the stop 702 with the ring feature 700.

After the thrombus extraction device 202 is deployed, the thrombus extraction device 202 can be fully expanded as shown in FIG. 23-H. In some embodiments, this can include allowing the full expansion of the thrombus extraction device 202 such that the thrombus extraction device 202 engages a wall 2220 of the blood vessel 2202. In some embodiments, the thrombus extraction device 202 can be fully expanded by moving the plunger 154 from the first position to the second position and securing the plunger 154 in the second position to thereby fix the relative position of the inner shaft 200 with respect to the intermediate shaft 140. In some embodiments, the movement of the plunger 154 from the first position to the second position proximally retracts the inner shaft 200 with respect to the intermediate shaft 140 to thereby fully expand the expandable cylindrical portion 208 of the thrombus extraction device 202. The proximal retraction of the inner shaft 200 with respect to the intermediate shaft 140 can further bring the stop 702 into engagement with the ring feature 700 to thereby fully expand the self-expanding coring element 206. In some embodiments, the securing of the plunger 154 in the second position can secure the self-expanding coring element 206 and the thrombus extraction device 202 in full expansion via the engagement of the stop 702 with the ring feature 700.

After the thrombus extraction device 202 has been deployed, the thrombus 2200 can be removed via the capture of the thrombus in the thrombus extraction device 202 via the proximal retraction of the thrombus extraction device 202 through the thrombus 2200 as shown in FIG. 34-D, which proximal retraction of the thrombus extraction device 202 can be, for example, in a direction of blood flow through the blood vessel 2202 or against the direction of blood flow through the vessel 2202. In some embodiments, the proximal retraction of the thrombus extraction device 202 through the thrombus 2200 can result in the capture of the distal end 2206 of the thrombus 2200 before the capture of the proximal end 2204 of the thrombus 2200.

In some embodiments, the proximal retraction of the thrombus extraction device 202 can result in the separation and/or coring of at least a portion of the thrombus 2200 from the wall 2220 of the blood vessel 2202 by, for example, the self-expanding coring element 206 and/or the stent portion, and the capture of that separated portion of the thrombus 2200 within the expandable cylindrical portion 208. In some embodiments, the expandable cylindrical portion 208 can be formed of the braided filament mesh structure that can be, for example, a net-like filament mesh structure. In some embodiments, a portion of the thrombus can be captured within the expandable cylindrical portion 208 by entering the expandable cylindrical portion 208 via the mouth 414 of the self-expanding coring element 206 and/or via one or several of the interstices 404 of the self-expanding coring element 206.

The distal end 2206 of the thrombus 2200 is separated and/or cored from the walls 2220 of the blood vessel 2202 by the self-expanding coring element 206 via the proximal retraction of the thrombus extraction device 202, and the thrombus 2200 is captured in the expandable cylindrical portion 208 of the thrombus extraction device 202 by the continued proximal retraction of the thrombus extraction device through the thrombus 2200. In some embodiments, the everted portion 2900 of the expandable cylindrical portion 208 can be distally advanced relative to and through the self-expanding coring element 206 and/or through the non-everted portion 2902 of the expandable cylindrical portion 208 in connection with the proximal retraction of the thrombus extraction device 202 to elongate the non-everted portion 2902 to allow capture of the thrombus 2200 in the expandable cylindrical portion 208 and particularly within the non-everted portion 2902 of the expandable cylindrical portion 208. In embodiments in which the distal end 217 of the expandable cylindrical portion 208 is slidably coupled to one of: the second intermediate shaft 3000, the third intermediate shaft 3002; and the inner shaft 200, the relative distal advance of the everted portion 2900 of the expandable cylindrical portion 208 can be achieved via forces applied to the expandable cylindrical portion 208 as the thrombus extraction device 202 is proximally retracted. In some embodiments, these forces can overcome frictional forces and can thus cause the coupling 3100 to displace distally relative to the one of: the second intermediate shaft 3000, the third intermediate shaft 3002; and the inner shaft 200 with which the coupling 3100 is coupled.

In some embodiments, this distal advance of the everted portion 2900 of the expandable cylindrical portion 208 relative to the self-expanding coring element 206 can be accomplished via the relative distal advance of the one of: the second intermediate shaft 3000, the third intermediate shaft 3002; and the inner shaft 200 with respect to the first intermediate shaft 140. In some embodiments in which the distal end 217 of the expandable cylindrical portion 208 is fixedly coupled the one of: the second intermediate shaft 3000, the third intermediate shaft 3002; and the inner shaft 200, the relative distal advance can be achieved by the fixing and/or pining of the position of that one of: the second intermediate shaft 3000, the third intermediate shaft 3002; and the inner shaft 200 and the proximal retraction of the first intermediate shaft 140. In the embodiment of FIG. 34-D in which the distal end 217 of the expandable cylindrical portion 208 is coupled to the second intermediate shaft 3000, the position of the second intermediate shaft 3000 can be pinned relative to the blood vessel 2202, the thrombus 2200 and/or the feature 3400, and the first intermediate shaft 140 can be proximally retracted with respect to the second intermediate shaft 3000 to increase the length of the non-everted portion 2902.

In some embodiments, the length of the non-everted portion 2902 of the expandable cylindrical portion 208 can be increased until the thrombus 2202 and/or portion of the thrombus 2202 is entirely captured with the thrombus extraction device 202 and specifically within the expandable cylindrical portion 208, or until the length of the non-everted portion 2902 can no longer be increased. In some embodiments, the thrombus 2202 can then be removed from the patient's body as depicted in FIGS. 25-E through 25-H.

With reference now to FIG. 35 a schematic illustration of one embodiment of a funnel catheter 3500 is shown. The funnel catheter 3500 can be part of thrombus extraction system 100. The funnel catheter 3500 comprises an elongate funnel member 3502, also referred to herein as an elongate funnel sheath 3502 or the elongate sheath 3502, having a proximal end 3504 and a distal end 3506. The elongate funnel member 3502 can be elastic and/or flexible. The elongate funnel member 3502 can comprise any desired length and any desired diameter. In some embodiments, the elongate funnel member 3502 can have an outer diameter of at least 10 French, at least 12 French, at least 14 French, at least 18 French, at least 20 French, at least 22 French, between 14 French and 24 French, between 15 French and 21 French, between 16 French and 22 French, and/or any other or intermediate size.

The elongate funnel member 3502 can comprise a radiopaque marker that can be, for example, part of the distal end 110 of the elongate funnel member 3502. The elongate funnel member 3502 defines a lumen extending between the proximal end 3504 and the distal end 3506. The lumen of the elongate funnel member 3502 can be sized to slidably receive the thrombus extraction catheter 104. In some embodiments, the lumen of the elongate member 106 can have an internal diameter of at least 2 French, at least 10 French, at least 14 French, at least 18 French, at least 20 French, at least 22 French, between 11 French and 12 French, between 10 French and 22 French, between 14 French and 21 French, between 16 French and 20 French, and/or any other or intermediate size. The lumen can terminate at a sealed aperture 3508, also referred to herein as a sealed hub 3508, located at the proximal end 3504 of the elongate funnel member 3502. In some embodiments, the sealed aperture 3508 can be self-sealing and/or can comprise a self-sealing seal.

The elongate funnel member 3502 can further include an aspiration port 3510 that can be at the proximal end 3504 of the elongate funnel member 3502 and/or connected to the proximal end 3504 of the elongate funnel member 3502 via, for example, a connecting tube 3512. In some embodiments, the aspiration port 3510 can be a part of, and/or connected to the sealed hub 3508. In some embodiments, the aspiration port 3510 can be selectively fluidly connected to the lumen via, for example, a valve 3514, also referred to herein as an aspiration valve 3514, which valve 3514 can be a tubing clamp that can be located at a position along the connecting tube 3512 between the lumen and the aspiration port 3510.

The elongate funnel member 3502 can further hold a dilator assembly 3516. The dilator assembly 3516 can be configured to hold the self-expanding funnel 1708 that can be attached to the distal end 3506 of the elongate funnel member 3502 in a constrained configuration, and to release the self-expanding funnel 1708 from that constrained configuration. The dilator assembly 3516, as shown in FIG. 36, can comprise a proximal end 3518, and a distal end 3520. The dilator assembly 3516 can further include an obturator 3522 having a proximal end 3524, a distal end 3526, and an elongate shaft 3528 extending therebetween. In some embodiments, the dilator assembly 3526 can have a length that is greater than a length of the elongate funnel member 3502, and in some embodiments, the elongate shaft 3528 can have a length that is greater than a length of the elongate member 3502 of the funnel catheter 3500. The obturator 3522 can further define a lumen extending through the obturator 3522, which lumen can receive a guidewire. In some embodiments, the guidewire can comprise any desired dimensions and can, in some embodiments, have a diameter of approximately 0.035 inches, a diameter of approximately 0.018 inches, a diameter of less than approximately 0.1 inches, and/or a diameter of less than approximately 0.05 inches. The dilator assembly 3516 can be sized and shaped so as to be able to slidably move through the lumen of the elongate member 3502.

The obturator 3522 can include the capture sheath 1500 that can proximally extend from the distal end 3526 of the obturator 3522, and the tip such as the atraumatic tip 1502 located at the distal end 3526 of the obturator 3522. The atraumatic tip 1502 can be radiopaque. The obturator 120 can further include the connection fitting 1504 that can be located at the proximal end 1506 of the capture sheath 1500. In some embodiments, the connection fitting 1504 can be configured to sealingly connect with the distal end 3506 of the elongate funnel member 3502 of the funnel catheter 3500.

The obturator 3522 can further include a stop portion 1508 located at the proximal end 3524 of the obturator 3522. In some embodiments, the stop portion 1508 can have a diameter larger than the lumen of the elongate funnel member 3502 of the funnel catheter 3500 and/or larger than the diameter of the sealed aperture 3508 so as to prevent the stop portion 1508 from entering into the lumen of the elongate funnel member 3502 and/or the sealed aperture 3508.

The dilator assembly 3516 can further include an advancing sheath 3530, also referred to herein as the moveable sheath 3530, that can, in some embodiments, extend, coaxially along a portion of the elongate shaft 3528 of the obturator 3522 between, for example, the proximal end 3524 and the distal end 3526 of the obturator 3522, and specifically between the stop portion 1508 and the proximal end 1506 of the capture sheath 1500. The advancing sheath 3530 can include a proximal end 3532, a distal end 3534, and a tubular shaft 3536 extending between the proximal end 3532 and the distal end 3534 of the advancing sheath 3530. The tubular shaft 3536 can define a lumen that can be sized to receive the obturator 3522 such that the advancing shaft 3530 is axially displaceable along the obturator 3533 from a loading position, as shown in FIG. 36, to a retracting position, as shown in FIG. 37. In some embodiments, the advancing sheath 3530 in the loading position is relatively more proximal with respect to the obturator 3522 than the advancing sheath 3530 in the retracting position.

The advancing sheath 3530 further comprises a stop 3538 located at the proximal end 3532 of the advancing sheath 3530. The stop 3538 can interact with one or several features of the obturator 3522 to secure the advancing sheath 3530 to the obturator 3522 and secure the relative position of the advancing sheath 3530 with respect to the obturator 3522. In some embodiments, for example, the stop 3538 can engage with a lock 3540 that can be, for example, connected to the stop portion 1508 of the obturator 3522.

The advancing sheath 3530 can further comprise mating features 3542 that can be, for example, located on the distal end 3534 of the advancing sheath 3530. The mating features 3542 can be sized, shaped, and configured to engage with the proximal end 1506 of the capture sheath 1500, and specifically with the connection fitting 1504 of the capture sheath 1500. In some embodiments, the mating features 3542 can be configured to sealingly connect with the connection fitting 1504 of the capture sheath. In some embodiments, the advancing sheath 3530 can have an outside diameter that is equal or approximately equal to an outside diameter of the capture sheath 1500.

With reference to FIGS. 38-A to 38-D, a process for deploying the self-expanding funnel 1708 is shown. The process can include providing the dilator assembly 3516 and the funnel catheter 3500 with the funnel 1708 affixed to the distal end 3506 of the funnel catheter 3500. In FIG. 38-A, the funnel catheter 3500 including the elongate funnel member 3502 is shown. The dilator assembly 3516 including the obturator 3522 and the advancing sheath 3530 in the loading position such that the stop 3538 of the advancing sheath 3530 engages with and/or is engaged with the lock 3540 of the obturator 3522. As seen in FIG. 38-A, the funnel 1708 is contained in a constrained configuration within the capture sheath 1500. When performed in a patient, the funnel catheter 3500 can be used to percutaneously access a venous vessel of a patient through, for example an access site that can be, for example, the popliteal access site, the femoral access site, or the internal jugular access site. In some embodiments, the funnel catheter can percutaneously access the venous vessel via an introducer sheath 102 inserted into the venous vessel at the access site. In some embodiments, percutaneously accessing the venous vessel via the introducer sheath can include inserting the funnel catheter 3500 into the venous vessel through the introducer sheath. The distal end 3506 of the funnel catheter 3500 can be advanced within the venous vessel to a position proximate to a thrombus, and in some embodiments, the distal end 3506 of the funnel catheter 3500 can be advanced within the venous vessel to a position proximal to a thrombus.

In FIG. 38-B, the self-expanding funnel 1708 is deployed from the constrained configuration with the capture sheath 1500 to an expanded configuration free of the capture sheath 1500. This can include distally advancing the capture sheath 1500 relative to the funnel catheter 3500 to unsheathe the self-expanding funnel 1708 from the constrained configuration to the unconstrained configuration. In some embodiments, distally advancing the capture sheath 1500 can include distally advancing the dilator assembly 3516 relative to the funnel catheter 3500. In some embodiments, the deployment of the self-expanding funnel 1708 can include proximally retracting the elongate sheath 3502 over the obturator 3522 and/or the dilator assembly 3516 to unsheathe the self-expanding funnel 1708 from the constrained configuration to the expanded configuration.

After the self-expanding funnel 1708 has been deployed, and as depicted in FIG. 38-C, the advancing shaft 3530 can be displaced from the loading position to the retracting position. In some embodiments, this displacement of the advancing shaft 3530 can occur via the proximal retraction of the obturator 3522 relative to the advancing shaft 3530, and in some embodiments, this displacement of the advancing shaft 3530 can occur via the distal advance of the advancing shaft 3530 relative to the obturator 3522. In some embodiments, the advancing shaft can be displaced from the loading position to the retracting position such that the mating features 3542 engage with the proximal end 1506 of the capture sheath 1500, and specifically with the connection fitting 1504 of the capture sheath 1500. In some embodiments, the positioning of the advancing sheath 3530 in the retracting position can prevent damage caused by the capture sheath 1500 or other components of the obturator 3522 during retraction of the obturator 3522 from the funnel catheter 3500. Specifically, the positioning of the advancing sheath 3530 in the retracting position provides a constant diameter of portions of the dilator assembly 3516 that retract through the sealed hub 3508.

After moving the advancing shaft 3530 to the retracting position, and as shown in FIG. 38-D, the dilator assembly 3516 can be retracted from the funnel catheter 3500. In some embodiments, the dilator assembly 3516 can be proximally retracted through the lumen of the funnel catheter 3500, and out the sealed hub 3508 of the funnel catheter 3500. In some embodiments in which the funnel catheter 3500 is used to access the venous vessel, the thrombus extraction catheter 104 constraining the TED 202 can be inserted into the venous vessel through the lumen of the elongate sheath 3502 of the funnel catheter 3500. In some embodiments, the thrombus extraction catheter 104 can be inserted into the venous vessel and advanced through the venous vessel until a distal tip 132 of the thrombus extraction catheter 104 is proximate to the thrombus, and in some embodiments, until the distal tip 132 of the thrombus extraction catheter 104 is distally past the thrombus or a portion of the thrombus. The TED 202 can then be deployed and proximally retracted relative to the funnel catheter 3500 to separate thrombus from the walls of the venous vessel and to capture thrombus within the TED 202. The TED 202 can be proximally retracted relative to the funnel catheter 3500 until an opening 414 of the thrombus extraction device 202 is within the self-expanding funnel 1708. The thrombus extraction device 202 can then be retracted through the funnel catheter 3500, or in some embodiments, the thrombus extraction device 202 can be maintained such that the opening 414 of the TED 202 remains in the funnel 1708 while the TED 202 and the funnel catheter 3500 are simultaneously withdrawn from the patient through the inserter sheath. In some embodiments, thrombus can be captured within the self-expanding funnel 1708, and the thrombus can be aspirated out of the patient via the funnel catheter 3500, and specifically via the lumen of the funnel catheter 3500, the connecting tube 3512, and the aspiration port 3510.

Figure 39:
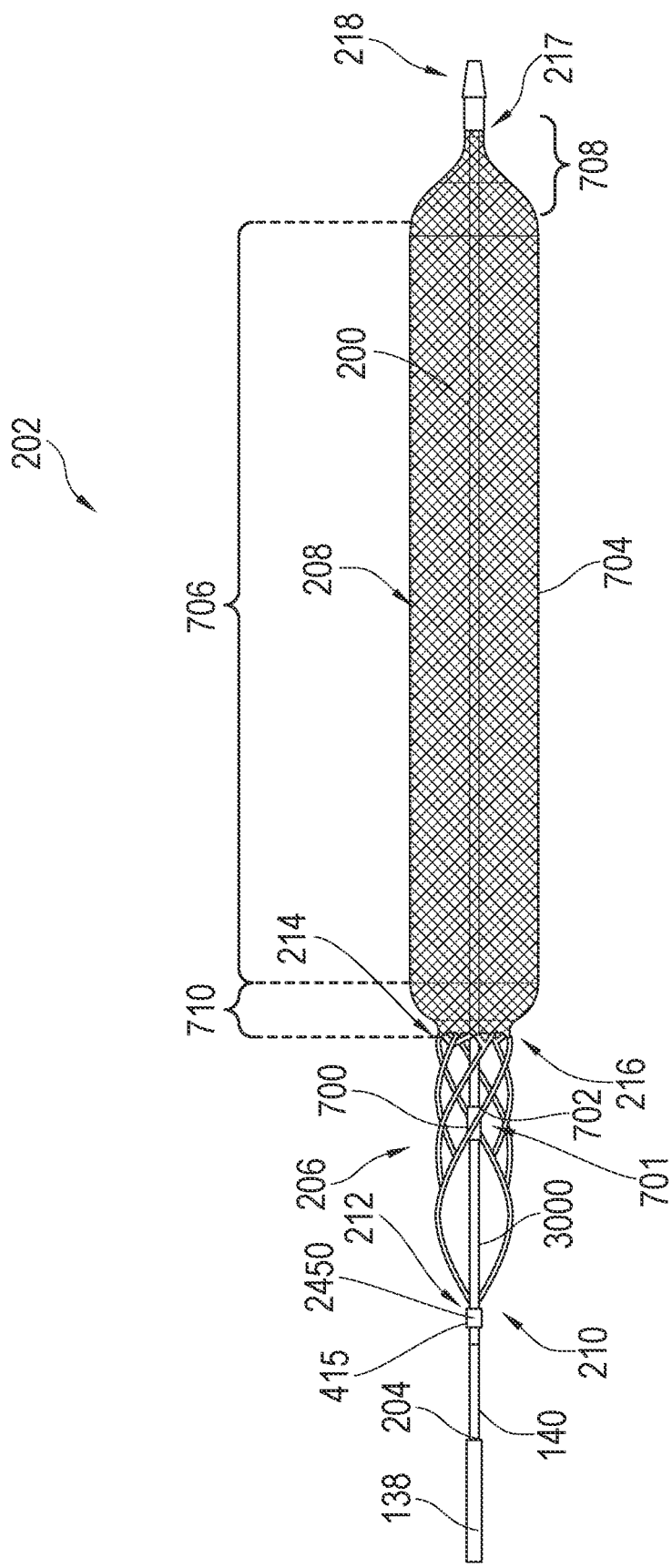
FIG. 39 is a top view of one embodiment of a stackable thrombus extraction device.

With reference now to FIG. 39, a top view of one embodiment of the thrombus extraction device 202 is shown. Specifically, FIG. 39 is a top view of one embodiment of the thrombus extraction device 202 with the expandable cylindrical portion 208 in an at least partially stacked configuration. The self-expanding coring element 206 is connected via the connection member 415 at the proximal end 210 of the self-expanding coring element 206 to the distal end 212 of the coring element shaft 140. As seen in FIG. 39, the coring element shaft 140, which can include radiopaque marker 2450, extends from the distal end 204 of the outer shaft 138.

The proximal end 216 of the expandable cylindrical portion 208 connects to the distal end 214 of the self-expanding coring element 206. In some embodiments, the expandable cylindrical portion 208 and specifically the proximal end 216 of the expandable cylindrical portion 208 is formed and/or woven on the distal end 214 of the self-expanding coring element 206 to thereby form a unitary thrombus extraction device 202, also referred to herein as an interwoven thrombus extraction device 202. The distal end 217 of the expanding cylindrical portion 208 connects to the distal end 218 of the tip shaft 200.

In some embodiments, and as seen in FIG. 39, the self-expanding coring element 206 can engage with all or portions of the stop shaft 3000 to affect the expansion of the self-expanding coring element 206. Specifically, in some embodiments, the self-expanding coring element 206 can include one or several features that can together form the expansion mechanism. 701, which expansion mechanism can include the ring 700 and the stop 702. The ring 700 can, in some embodiments, be the same material as the self-expanding coring element 206 or can be a different material than the self-expanding coring element 206. The ring 700 can be integrally formed with the self-expanding coring element 206 and/or can be attached to the self-expanding coring element via, for example, one or several welds, adhesive, one or several mechanical fasteners, or the like. The ring 700 can have a diameter larger than the diameter of the stop shaft 3000 such that the ring 700 is slidable along the stop shaft 3000, or in some embodiments, the ring 700 can have a diameter less than the diameter of the stop shaft 3000 such that the ring 700 is connected to the stop shaft 3000 via an interference fit that secures and/or partially secures the position of the ring 700 with respect to the stop shaft 3000.

The stop 702 can comprise a variety of shapes and sizes and can be made from a variety of materials. In some embodiments, the stop 702 can comprise a polymeric member and/or metallic member that is affixed to a portion of the stop shaft 3000. The stop 702 can, in some embodiments, have the form of a tab, a protrusion, a flange, a ridge or the like. In some embodiments, the stop 702 can be sized and shaped to engage with the ring 700 to thereby apply proximally directed force to the self-expanding coring element 206 when stop shaft 3000 is proximally displaced relative to the self-expanding coring element 206. In some embodiments, the stop shaft 3000 can be displaced via, for example movement of the plunger 154 to the second position and/or displacement of the shuttle to a second position. In some embodiments, the shuttle can be attached to a spring, such as a constant force spring, which can cause this displacement of the shuttle. In some embodiments, at least the portion of the self-expanding coring element 206 located between the ring 700 and the connection member 415 can be forcibly expanded by the application of this proximally directed force to ring 700, thereby moving the self-expanding coring member 206 to full expansion. In other embodiments, the engagement of the ring 700 and the stop 702 can connect the thrombus extraction device 202 to the spring, thereby bringing the TED 202 to full expansion. In another embodiment, the expansion mechanism 701 does not include the ring 700 and the stop 702 is not attached the stop shaft 3000, rather, the expansion mechanism 701 comprises a wire or filament that can be, for example, a metallic or polymeric material. The wire or filament wraps through the self-expanding coring element 206 and can be attached such as fixedly attached to the stop shaft 3000. In some embodiments, for example, the terminating end of the filament can be fixed to the stop shaft 3000 via a compression or tension spring, which spring allows the self-expanding coring element 206 to reduce in diameter slightly without disengaging the stop 702. In some embodiments, the wire or filament is comprised of an elastic material to include the functionality of the compression or tension spring.

The expandable cylindrical portion 208 can comprise the braided filament mesh structure 704 that can be configured to capture thrombus. In some embodiments, the braided filament mesh structure can be coextensive with the expandable cylindrical portion 208 and thus can share a proximal end 216 and/or a distal end 217. In the embodiment shown in FIG. 7, the braided filament mesh structure 704 can be a braid of elastic filaments having a generally tubular, elongated portion 706 and a distal tapered portion 708. In embodiments in which the expandable cylindrical portion 208 is at least partially stacked, the expandable cylindrical portion 208 can further include a proximal tapered portion 710. In other embodiments, the braided filament mesh structure 704 can be any porous structure and/or can have other suitable shapes, sizes, and configurations (e.g., the distal portion 708 can be generally cylindrical, etc.).

In some embodiments, the tip shaft 200 is moveable relative to the coring element shaft 140 to thereby allow the changing of the length of the expandable cylindrical portion 208. In some embodiments, and as discussed above, the change in the length of the expandable cylindrical portion 208 can result in the movement of the expandable cylindrical portion 208 between two or more of: a stacked configuration; an expanded configuration; and a collapsed configuration. In some embodiments, the change in the configuration of the expandable cylindrical portion 208 can result in a change of diameter of the expandable cylindrical portion 208. Specifically, in some embodiments, the expandable cylindrical portion 208 can have a diameter in the stacked configuration that is greater than a diameter of the self-expanding coring element 206. In some embodiments, the diameter of the expandable cylindrical portion 208 can be between 1 mm and 20 mm larger than the diameter of the self-expanding coring element 206, can be between 2 mm and 10 mm larger than the diameter of the self-expanding coring element 206, and/or can be between 2 mm and 6 mm larger than the diameter of the self-expanding coring element 206.

With reference now to FIG. 40, a section view of one embodiment of the handle 134 is shown. The handle 134 includes a distal end 142 and a proximal end 144. The coring element shaft 140 connects to the distal end 142 of the handle 134 and distally extends away from the handle 134. A lock feature 146 is located at the distal end 142 of the handle 134. The lock feature 146 can be configured to engage with a component and/or portion of the outer shaft 138 to secure the outer shaft 138 to the handle 134. In some embodiments, the outer shaft 138 can be proximally slid over the coring element shaft 140 and secured to the handle via the locking feature to deploy and/or partially deploy the thrombus extraction device 202. The handle can further include the second flush port 156. The second flush port 156 can be fluidly connected to an internal portion of the handle 134 and thereby connect to the lumen of the coring element shaft 140 so as to allow the flushing of the lumen of the coring element shaft 140.

The handle 134 can include a housing 1200 that defines an internal volume 1202. As seen in FIG. 40, the stop shaft 3000 extends through the lumen of the coring element shaft 140 into the internal volume 1202 of the handle 134 and connects to, and/or is coupled to a shuttle 4000 that slides along a track 4002 within the housing 1200 of the handle 134. The shuttle 4000 is moveable between a first position relatively more proximate to the distal end 142 of the handle 134 and a second position relatively more proximate to the proximal end 144 of the handle 134. In some embodiments, the shuttle 4000 can be located in the first position when the self-expanding coring element 206 is in an undeployed configuration, and the shuttle 4000 can be located in the second position when the self-expanding coring element 206 is at full expansion. In some embodiments, the movement of the shuttle 4000 from the first position to the second position can move the thrombus extraction device 202, and specifically the self-expanding coring element 206 to an expanded state, which expanded state can be full expansion.

The shuttle 4000 can be connected to and/or coupled to a force generation component such as, for example, a spring 4004. The spring 4004 can comprise, for example, a compression spring, a tension spring, a torsion spring, or a constant force spring such as a watch spring. In some embodiments, the spring 4004 can apply a force to the shuttle 400 to bias the thrombus extraction device 202, and specifically the self-expanding coring element 206 to the expanded state and more specifically to hold the thrombus extraction device 202, and specifically the self-expanding coring element 206 in full expansion.

As seen in FIG. 40, the tip shaft 200 can extend into and/or through the handle 134. In some embodiments, for example, the tip shaft 200, and/or a feature connected to the tip shaft 200 such as a plunger, can extend through the handle 134. In some embodiments, the extension of the tip shaft 200 and/or feature connected to the tip shaft 200 through the handle 134 can allow the control of the position of the tip shaft 200 with respect to one or more of the other shafts 138, 140, 3000, 3002 and/or with respect to the handle 134 or the self-expanding coring element 206. In some embodiments, this control of the relative position of the tip shaft 200 likewise controls the expandable cylindrical portion 208, and specifically controls the braided filament mesh structure 704. In some embodiments, this control can enable movement of the expandable cylindrical portion 208, and specifically controls the braided filament mesh structure 704 between collapsed, expanded, and stacked configurations.

Due to the connection of the braided filament mesh structure 704 to the distal end 218 of the tip shaft 200, axial movement of the tip shaft 200 radially expands/shortens or collapses/lengthens the braided filament mesh structure 704 of the TED 200. For example, so long as the coring element shaft 140 is fixed and/or limited to axial movement at a rate less than that of the tip shaft 200: (1) distal movement of the tip shaft 200 stretches the braided filament mesh structure 704 along its longitudinal axis such that the radius of the braided filament mesh structure 704 decreases and the length of the braided filament mesh structure 704 increases; and (2) proximal movement of the tip shaft 200 compresses the braided filament mesh structure 704 along its longitudinal axis such that the radius of the braided filament mesh structure 704 increases and the length of the braided filament mesh structure 704 decreases. The filament mesh structure 704 can be positioned in a plurality of configurations including, for example, a stacked configuration, a collapsed configuration, and an expanded configuration. The filament mesh structure 704 in the stacked configuration can have a shorter length than the filament mesh structure 704 in the expanded configuration, and the filament mesh structure 704 in the expanded configuration can have a shorter length the filament mesh structure 704 in the collapsed configuration. In certain embodiments, the braided filament mesh structure 704 can have any desired length in the collapsed configuration, including, for example, a length in the collapsed configuration between approximately 1 and 80 inches, between 2 and 60 inches, between 3 and 50 inches, between approximately 5 and 30 inches, between approximately 10 and 20 inches, and/or of approximately 16 inches, and in some embodiments, the braided filament mesh structure 704 can have a length in the expanded configuration of between approximately 1 and 25 inches, between approximately 10 and 20 inches, and/or of approximately 11 inches. In some embodiments, the filament mesh structure 704 can have any desired length in the stacked configuration including, for example, a length between 1 and 50 inches, a length between 1 and 30 inches, a length between 1 and 20 inches, a length of between 1 and 15 inches, between 2 and 10 inches, and/or of approximately 5 inches in the stacked configuration.

In some embodiments, the braid angles of the filament mesh structure 704 can change between configurations. As the length of the filament mesh structure 704 increases, the braid angle θ can decrease, and as the length of the filament mesh structure 704 decreases, the braid angle θ can increase. In some embodiments, the braid angle θ of the filament mesh structure 704 can be less than approximately 10°, less than approximate 20°, less than approximately 30°, less than approximately 40°, and/or less than approximately 50° when the filament mesh structure 704 is in the collapsed configuration. In some embodiments, the braid angle of the filament mesh structure 704 can be between 20° and 85°, between 30° and 70°, between 35° and 60°, between 40° and 50°, and/or approximately 45° when the filament mesh structure 704 is in the expanded configuration. In some embodiments, the braid angle of the filament mesh structure 704 can be greater than approximately 45°, greater than approximately 60°, greater than approximately 70°, and/or greater than approximately 80° when the filament mesh structure 704 is in the stacked configuration.

With reference now to FIGS. 41-A to 41-F, views depicting one embodiment of a process for expanding a stackable thrombus extraction device 202 in a blood vessel 2200 is shown. In some embodiments, the process of FIGS. 41-A to 41-F, can be performed as a part of, or in the place of the process shown in FIGS. 23-A to 23-H. In some embodiments, the portion of the process shown in FIGS. 41-E and 41-F can be performed in the place of steps 23, and particularly in the place of steps 23-G and 23-H. In some embodiments, the process of FIGS. 41-A to 41-F can be performed as a part of or in the place of the process of FIGS. 24-A and 24-B, or of FIGS. 25-A to 25-H. In some embodiments, for example, the process of FIGS. 41-A to 41-F can advantageously eliminate the necessity of performing the process of FIGS. 24-A and 24-B as the expandable cylindrical portion 208 of the thrombus extraction device 202 can be controlled to limit the extension of the thrombus extraction device 202 beyond the thrombus 2200. This benefit of the process of FIGS. 41-A to 41-F is particularly advantageous when the thrombus 2200 forms proximate to a feature 3400.

The process for expanding a stackable thrombus extraction device 202 in a blood vessel 2200 can be performed using all or portions of the thrombus extraction system 100. In some embodiments, the process expanding a stackable thrombus extraction device 202 in a blood vessel 2200 can be performed in connection with a monitoring technique, such as fluoroscopy, angiography, and/or ultrasonic monitoring. In some embodiments, the monitoring technique can be used to monitor the deployment of the thrombus extraction device 202 in the vessel via observation of the one or several radiopaque markers located on the introducer sheath 102 and/or the thrombus extraction catheter 104.

The process begins at FIG. 41-A, wherein the thrombus 2200 is identified in the blood vessel 2202 such as venous vessel. In some embodiments, the thrombus 2200 can be located in the peripheral vasculature of the patient's body. The thrombus 2200 can comprise the proximal end 2204 and the distal end 2206. In some embodiments, the identification of the blood vessel 2202 can further include the determination of whether the thrombus 2200 in the blood vessel 2202 is suitable for thrombus extraction. In some embodiments, the thrombus 2200 in the blood vessel 2202 can be suitable for extraction when the blood vessel 2202 has a diameter of at least 3 millimeters. In some embodiments, the thrombus 2200 in the blood vessel 2202 can be suitable for extraction when the blood vessel 2202 has a diameter of at least 3 millimeters and is at least one of a femoral vein, an iliac vein, a popliteal vein, a posterior tibial vein, an anterior tibial vein, or a peroneal vein. In some embodiments, and as part of identifying the thrombus 2200, a feature 3400 can be identified, which feature 3400 can be located distal of the distal end 2206 of the thrombus 2200.

After the thrombus 2200 has been identified, a guidewire 3402 can be inserted through the blood vessel 2202, through the thrombus 2200, and in some embodiments, through the feature 3400. In some embodiments, the guidewire 3402 can be inserted into the blood vessel, as shown in FIG. 34-A, via an access site such as, for example, the internal jugular (IJ) access site, the femoral access site, the popliteal access site, or other venous or arterial access sites. In some embodiments, the guidewire 3402 can be inserted using one or several imaging and/or monitoring techniques including, for example, fluoroscopy, angiography, and/or ultrasonic monitoring.

After the thrombus has been identified, and as shown in FIG. 41-A, the introducer sheath 102 is advanced, either with or against the direction of blood flow in the blood vessel, such that the distal end 110 of the introducer sheath 102 and/or the obturator 120 is proximate to the thrombus 2200, and particularly is proximate to the thrombus 2200 at a position proximal of the thrombus 2200. In some embodiments, this can include providing the introducer sheath 102 which can include a dilator shaft 4100 extending through the lumen of the elongate member 106 of the introducer sheath 102. In some embodiments, the dilator shaft 4100 can seal, or partially seal the lumen of the elongate member 106 at the distal end 110 of the introducer sheath 102. In some embodiments, the introducer sheath 102 inserted in FIG. 41-A can be used in connection with the funnel catheter 3500. In some embodiments, such an introducer sheath 102 used with the funnel catheter 3500 can include a funnel 1708, and in some embodiments, the introducer sheath 102 used with the funnel catheter 3500 does not include a funnel 1708. The introducer sheath can percutaneously access the circulatory system of the patient and specifically the peripheral vasculature including, for example, an artery, and a blood vessel or venous vessel of the patient via an access site 2208 which can be one of the above referenced access sites.

After the introducer sheath 102 has been advanced to a desired position, the self-expanding funnel 1708 can be deployed and/or unsheathed from the constrained configuration to the expanded configuration as depicted in FIG. 41-B. In some embodiments, this can include percutaneously accessing the venous vessel of the patient by inserting the funnel catheter 3500 into the venous vessel via the access site. In the embodiment of FIG. 41-B, percutaneously accessing the venous vessel of the patient with the funnel catheter 3500 can include inserting the funnel catheter 3500 into the venous vessel through the introducer sheath. The distal end 3506 of the funnel catheter 3500 can be advanced within the venous vessel to a position proximate to a thrombus, and in some embodiments, the distal end 3506 of the funnel catheter 3500 can be advanced within the venous vessel to a position proximal to a thrombus. After the funnel catheter 3500 has reached the desired position, the funnel 1708 can be deployed as described with respect to FIGS. 38-A to 38-D.

After the self-expanding funnel 1708 has been deployed, a portion of the thrombus extraction catheter 104 such as the outer shaft 138 can be inserted into the lumen 1701 of the introducer sheath 102 via the sealed aperture 112. In some embodiments, this can include providing the thrombus extraction catheter 104 which comprises the thrombus extraction device 202. In some embodiments, the thrombus extraction device 202 can be constrained within the outer shaft 138 and can inserted, together with the outer shaft 138, into the lumen of the elongate member 106 via the sealed aperture 112. In some embodiments, the outer shaft 138 of the thrombus extraction catheter 104 can have a diameter so as to dilate the seal of the sealed aperture 112 such that the sealed aperture 112 seals around and seals to the outer shaft 138.

After the outer shaft 138 has been inserted into the lumen 1701 of the introducer sheath 102, a portion of the thrombus extraction catheter 104 can be inserted via the introducer sheath 102 into the blood vessel 2202. In some embodiments, the distal end 132 of the thrombus extraction catheter 104 can be advanced to a position proximate to the thrombus 2200 and/or to a position proximal to the thrombus 2200. In some embodiments, the insertion and/or advance of the thrombus extraction catheter 104 can be monitored and specifically can be fluoroscopically monitored. In some embodiments, the position of one or several radiopaque markers, including radiopaque marker 222 of the thrombus extraction catheter 104 can be monitored.

After the portion of the thrombus extraction catheter 104 has been inserted into the blood vessel 2202, a portion of the thrombus extraction catheter 104 can be distally advanced through the clot 2200 as depicted in FIG. 41-C. In some embodiments, this distal advance through the clot 2200 can be either with or against the direction of blood flow. In some embodiments, the portion of the thrombus extraction catheter 104 distally advanced through the clot 2000 can contain and/or constrain the thrombus extraction device 202. In some embodiments, distally advancing the portion of the thrombus extraction catheter 104 through the clot can include advancing the portion of the thrombus extraction catheter 104 until the radiopaque marker 222, that can be fluoroscopically monitored and that can be located at the distal end 218 of the tip shaft 200, is distally past the thrombus 2200 and/or a portion of the thrombus 2200.

After the portion of the thrombus extraction catheter 104 is distally advanced through the clot 2200, the thrombus extraction device 202 can be partially deployed as depicted in FIG. 41-D. In some embodiments, the thrombus extraction device 202 can be partially deployed by either advancing a portion of the thrombus extraction device 202 beyond the distal end 204 of the outer shaft 138 or by retracting the outer shaft 138 relative to the thrombus extraction device 202 until a portion of the thrombus extraction device 202 is beyond the distal end 204 of the outer shaft 138. In some embodiments, the thrombus extraction device can be partially deployed such that a portion of the thrombus extraction device 202 is distally past the thrombus 2200 and/or distally past a desired portion of the thrombus 2200.

In some embodiments, the portion of the thrombus extraction device 202 is advanced beyond the distal end 204 of the outer shaft 138 by distally advancing the coring element shaft 140 with respect to the outer shaft 138. In some embodiments, the coring element shaft 140 can be distally advanced until the lock feature 146 contacts the mating feature 148, and the lock feature 146 can be mated and/or secured to the mating feature 148 to fix the relative position of the coring element shaft 140 with respect to the outer shaft 138.

In some embodiments, the partial deployment of the thrombus extraction device 202 can be monitored, and specifically, the deployment of the thrombus extraction device 202 can be fluoroscopically monitored via, for example, the radiopaque marker 222 and the radiopaque marker located at one or both of the distal end 204 of the outer sheath 138 and the distal end 212 of the coring element sheath 140 such as, for example radiopaque marker 2450. In some embodiments, the partial deployment of the thrombus extraction device 202, and specifically the advancing of the thrombus extraction device 202 beyond the distal end 204 of the outer shaft 138 or retracting the outer shaft 138 relative to the thrombus extraction device 202 can be ceased based on a position the distal end 204 of the outer sheath 138 comprising the radiopaque marker (first radiopaque marker) relative to the radiopaque marker 222 located on the thrombus extraction device 202 (second radiopaque marker).

In some embodiments, the coring element shaft 140 and/or the tip shaft 200 can be manipulated so that a desired portion of the thrombus extraction device 202, and specifically of the expandable cylindrical portion 208 of the thrombus extraction device 202 extends beyond the outer shaft 138. In some embodiments, this can comprise any desired extension of the thrombus extraction device 202 beyond the outer shaft 138 including, for example, the extension of less than approximately 20 inches of the thrombus extraction device 202 beyond the outer shaft 138, the extension of less than approximately 16 inches of the thrombus extraction device 202 beyond the outer shaft 138, the extension of less than approximately 10 inches of the thrombus extraction device 202 beyond the outer shaft 138, the extension of less than approximately 5 inches of the thrombus extraction device 202 beyond the outer shaft 138, the extension of less than approximately 2 inches of the thrombus extraction device 202 beyond the outer shaft 138, or the extension of less than approximately 2 inches of the thrombus extraction device 202 beyond the outer shaft 138.

In some embodiments, the thrombus extraction device 202 can be partially deployed until the thrombus extraction device 202, and specifically until the distal end 217 of the cylindrical portion 208 of the thrombus extraction device 202 reaches a desired position, such as, for example, a desired position with respect to a feature 3400 of the blood vessel 2202 or with respect to an anatomical structure such as, for example, valve. In some embodiments, this feature 3400 of the blood vessel can comprise a transition, such as a branch point, from one blood vessel to another, a desired diameter of the blood vessel, or the like. In some embodiments, the thrombus extraction device 202 can be deployed until the distal end 217 of the cylindrical portion 208 of the thrombus extraction device 202 reaches a desired point beyond a branch point of a vessel such that the cylindrical portion 208 is wholly or partially contained in a different blood vessel, or a blood vessel having a larger diameter than the remaining portions of the thrombus extraction device 202. In some embodiments, when the distal end 217 of the cylindrical portion 208 of the thrombus extraction device 202 reaches this desired position, the tip shaft 200 can be pinned and the position of the distal end 217 of the cylindrical portion 208 of the thrombus extraction device 202 can be maintained.

After the thrombus extraction device 202 is partially deployed, a portion of the thrombus extraction device 202 can be stacked. Specifically, in some embodiments, the deployed portion of the thrombus extraction device can include all or portions of the cylindrical portion 208 of the thrombus extraction device 202, and specifically of the filament mesh structure 704. In some embodiments, the deployed portions of the cylindrical portion 208 of the thrombus extraction device 202, and specifically of the filament mesh structure 704 can be stacked, or partially stacked as depicted in FIG. 41-E. In some embodiments, this stacking can be achieved by relatively distally advancing the coring element shaft 140 with respect to the tip shaft 200, which can change the braid angle θ, decrease the length of the cylindrical portion 208 of the thrombus extraction device 202, and specifically of the filament mesh structure 704, and increase the diameter of the cylindrical portion 208 of the thrombus extraction device 202, and specifically of the filament mesh structure 704. In some embodiments, this stacking can occur while the tip shaft 200 is pinned and/or while the position of the distal end 217 of the cylindrical portion 208 of the thrombus extraction device 202 is maintained at a desired location.

The deployment of the thrombus extraction device 202 can be continued until the thrombus extraction device 202 is deployed from the outer shaft 138 as shown in FIG. 41-F. In some embodiments, this can be achieved vie the continued distal advancement of the coring element shaft 140 which can be, in some embodiments, a relative distal advancement with respect to the tip shaft 200 and/or the outer shaft 138. In some embodiments, this continued deployment of the thrombus extraction device 202 can cause the continued stacking of portions of the cylindrical portion 208 of the thrombus extraction device 202, and specifically of the filament mesh structure 704.

With reference now to FIGS. 42-A and 42-B, views depicting one embodiment of a process for retracting stackable thrombus extraction device 202 through thrombus in a blood vessel 2200 is shown. The process of FIGS. 42-A and 42-B, can be performed as a part of, or in the place of the process shown in FIGS. 25-A to 25-H.

After the thrombus extraction device 202 is deployed, or as part of the deployment of the thrombus extraction device 202, the thrombus extraction device 202 can be fully expanded. In some embodiments, this can include allowing the full expansion of the thrombus extraction device 202 such that the thrombus extraction device 202 engages a wall 2220 of the blood vessel 2202. In some embodiments, the thrombus extraction device 202 can be fully expanded by moving the plunger 154 from the first position to the second position and securing the plunger 154 in the second position to thereby fix the relative position of the stop shaft 3000 with respect to the coring element shaft 140. In some embodiments, the movement of the plunger 154 from the first position to the second position proximally retracts the stop shaft 3000 with respect to the coring element shaft 140 to thereby fully expand the expandable cylindrical portion 208 of the thrombus extraction device 202. The proximal retraction of the stop shaft 3000 with respect to the coring element shaft 140 can further bring the stop 702 into engagement with the ring feature 700 to thereby fully expand the self-expanding coring element 206. In some embodiments, the securing of the plunger 154 in the second position can secure the self-expanding coring element 206 and the thrombus extraction device 202 in full expansion via the engagement of the stop 702 with the ring feature 700.

In some embodiments, the thrombus extraction device can be fully expanded by the movement of the shuttle 4000 from the first position to the second position. In some embodiments, the shuttle 4000 can be moved along the track 4002 by the spring 4004 to thereby move the stop shaft 3000 with respect to the self-expanding coring element 206. In some embodiments, this movement of the stop shaft 3000 can bring the stop 702 into engagement with the ring feature 700 to thereby fully expand the self-expanding coring element 206. In some embodiments, the spring 4004 can secure the self-expanding coring element 206 and the thrombus extraction device 202 in full expansion via the engagement of the stop 702 with the ring feature 700. In some embodiments, the shuttle 4000 moves from the first position to the second position until compressive forces applied to the self-expanding coring element 206 equal the expansive forces of the self-expanding coring element 206 and of the spring 4004. In some embodiments, these compressive forces equal the expansive forces when the self-expanding coring element 206 engages the wall 2220 of the blood vessel 2202.

After the thrombus extraction device 202 is at full expansion, the thrombus extraction device 202 can be proximally retracted through the thrombus 2200 as shown in FIG. 42-B. In some embodiments, the proximal retraction of the thrombus extraction device 202 can be, for example, in a direction of blood flow through the blood vessel 2202 or against the direction of blood flow through the vessel 2202. In some embodiments, the proximal retraction of the thrombus extraction device 202 through the thrombus 2200 can result in the capture of the distal end 2206 of the thrombus 2200 before the capture of the proximal end 2204 of the thrombus 2200.

In some embodiments, the proximal retraction of the thrombus extraction device 202 can result in the separation and/or coring of at least a portion of the thrombus 2200 from the wall 2220 of the blood vessel 2202 by, for example, the self-expanding coring element 206 and/or the stent portion, and the capture of that separated portion of the thrombus 2200 within the expandable cylindrical portion 208. In some embodiments, the expandable cylindrical portion 208 can be formed of the braided filament mesh structure that can be, for example, a net-like filament mesh structure. In some embodiments, a portion of the thrombus can be captured within the expandable cylindrical portion 208 by entering the expandable cylindrical portion 208 via the mouth 414 of the self-expanding coring element 206 and/or via one or several of the interstices 404 of the self-expanding coring element 206.

The distal end 2206 of the thrombus 2200 is separated and/or cored from the walls 2220 of the blood vessel 2202 by the self-expanding coring element 206 via the proximal retraction of the thrombus extraction device 202, and the thrombus 2200 is captured in the expandable cylindrical portion 208 of the thrombus extraction device 202 by the continued proximal retraction of the thrombus extraction device through the thrombus 2200. In some embodiments, the expandable cylindrical portion 208 can unstack during the proximal retraction of the thrombus extraction device 202. In some embodiments, this unstacking can be accomplished by proximally retracting the coring element shaft 140 with respect to the tip shaft 200. In some embodiments, this can be achieved by merely retracting the coring element shaft 140 and allowing drag caused by the thrombus entering the expandable cylindrical portion 208 to prevent the tip shaft 200 to moving simultaneous with and/or to the same degree as the coring element shaft 140. In some embodiments, this unstacking can be achieved by maintaining the pinning of the tip shaft 200 while retracting the coring element shaft with respect to the tip shaft 200.

The thrombus extraction device 202 can be unstacked until the entire thrombus extraction device 202 is unstacked or until a desired level of unstacking is achieved. The thrombus extraction device 202 can then be retracted via the proximal retraction of the thrombus extraction catheter 104, the outer shaft 138, and/or the coring element shaft 140. In some embodiments, the thrombus extraction device 202 can be retracted until all or a portion of the thrombus extraction device 202 is within the funnel catheter 3500, and specifically within the funnel 1708. In some embodiments, for example, the thrombus extraction device can be retracted until the self-expanding coring element 206 is within the funnel 1708 and/or until the mouth 414 is within the funnel. In some embodiments, the containment of the mouth 414 within the self-expanding funnel 1708 can be fluoroscopically verified. In some embodiments, the mouth 414 can be determined as wholly contained within the self-expanding funnel 1708 via fluoroscopic monitoring based on the alignment/relative positioning of the distal end 212 of the intermediate shaft 140 comprising a radiopaque marker 2450 and/or the radiopaque marker 222 with respect to the distal end 110 comprising a radiopaque marker 2452 of the elongate member 106 of the introducer sheath 102.

After the mouth 414 of the thrombus extraction device 202 is within the funnel 1708, the position of the thrombus extraction device 202 can be maintained such that the mouth 414 of the thrombus extraction device 202 remains in the funnel 1708 while the thrombus extraction device 202 and the funnel catheter 3500 are simultaneously withdrawn from the patient through the inserter sheath 102. In some embodiments, thrombus can be captured within the self-expanding funnel 1708, and the thrombus can be aspirated out of the patient via the funnel catheter 3500, and specifically via the lumen of the funnel catheter 3500, the connecting tube 3512, and the aspiration port 3510.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

In the previous description, various embodiments of the present invention are described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method for removal of a vascular thrombus from a blood vessel of a patient, the method comprising:
   positioning a thrombus extraction device entirely distal to the thrombus in the blood vessel, wherein the thrombus extraction device includes an expandable coring element and an expandable cylindrical braided mesh, and wherein a proximal portion of the cylindrical braided mesh is coupled to a distal portion of the coring element;
   expanding the coring element by proximally retracting a first shaft of the thrombus extraction device relative to a second shaft of the thrombus extraction device, wherein a proximal portion of the coring element is coupled to the second shaft, and wherein the first shaft is slidably positioned within the second shaft; and
   retracting the thrombus extraction device at least partially through the thrombus such that (a) the coring element separates a portion of the thrombus within the blood vessel and (b) the cylindrical braided mesh captures the portion of the thrombus.

2. The method of claim 1 wherein the coring element and the cylindrical braided mesh are formed from different materials.

3. The method of claim 1 wherein the coring element and the cylindrical braided mesh have different porosities.

4. The method of claim 1 wherein the coring element is a stent-like structure.

5. The method of claim 1 wherein the coring element is a unitary structure.

6. The method of claim 5 wherein cylindrical braided mesh comprises a plurality of filaments interwoven on the distal portion of the coring element.

7. The method of claim 1 wherein expanding the coring element includes proximally retracting the first shaft such that a feature on the first shaft engages a portion of the coring element.

8. The method of claim 1 wherein expanding the coring element includes retracting the first shaft to physically engage a feature on the first shaft with a portion of the coring element.

9. The method of claim 1 wherein positioning the thrombus extraction device includes moving the coring element relative to the cylindrical braided mesh, and wherein the method further comprises fixing a position of the cylindrical braided mesh relative to the coring element.

10. The method of claim 1 wherein retracting the thrombus extraction device at least partially through the thrombus includes at least partially receiving the portion of the thrombus through a mouth of the coring element, wherein the mouth is angled relative to a longitudinal axis of the coring element.

11. A method for removal of a vascular thrombus from a blood vessel of a patient, the method comprising:
 deploying a thrombus extraction device from a delivery catheter such that the thrombus extraction device is positioned at least partially distal to the thrombus in the blood vessel, wherein the thrombus extraction device includes an expandable coring element and an expandable cylindrical braided mesh, and wherein a proximal portion of the cylindrical braided mesh is coupled to a distal portion of the coring element;
 retracting the coring element proximally through the blood vessel distal of the delivery catheter relative to the cylindrical braided mesh and at least partially through the thrombus to (a) increase a length of the cylindrical braided mesh and (b) separate a portion of the thrombus from a wall of the blood vessel; and
 capturing the portion of the thrombus within the cylindrical braided mesh.

12. The method of claim 11 wherein the coring element and the cylindrical braided mesh are formed from different materials.

13. The method of claim 11 wherein the coring element and the cylindrical braided mesh have different porosities.

14. The method of claim 11 wherein the coring element is a unitary structure.

15. The method of claim 14 wherein the cylindrical braided mesh comprises a plurality of filaments interwoven on the distal portion of the coring element.

16. A method for removal of a vascular thrombus from a blood vessel of a patient, the method comprising:
 positioning a thrombus extraction device at least partially distal to the thrombus in the blood vessel, wherein the thrombus extraction device includes an expandable coring element and an expandable cylindrical structure;
 expanding the coring element by proximally retracting a shaft of the thrombus extraction device such that a feature on the first shaft engages a portion of the coring element; and
 retracting the thrombus extraction device at least partially through the thrombus such that (a) the coring element separates a portion of the thrombus within the blood vessel and (b) the cylindrical structure captures the portion of the thrombus.

17. The method of claim 16 wherein expanding the coring element includes fixing a position of the coring element while retracting the shaft of the thrombus extraction device.

18. The method of claim 16 wherein the portion of the coring element is a proximal portion of the coring element.

19. The method of claim 16 wherein the coring element is a unitary structure, and wherein the cylindrical structure is a mesh of filaments.

20. The method of claim 16 wherein the portion of the coring element includes a ring member, and wherein the feature on the first shaft is sized and shaped to engage the ring member.

* * * * *